United States Patent
Huang et al.

(10) Patent No.: US 10,238,696 B2
(45) Date of Patent: Mar. 26, 2019

(54) LACTIC ACID BACTERIA AND USE THEREOF

(71) Applicant: New Bellus Enterprises Co., Ltd., Tainan (TW)

(72) Inventors: Chun-Chih Huang, Tainan (TW); Wen-Ying Huang, Tainan (TW); Hsueh Fang Wang, Taichung (TW); Paik Seong Lim, Taichung (TW); Pin Hsiu Liu, Taichung (TW)

(73) Assignee: NEW BELLUS ENTERPRISES CO., LTD., Tainan (TW)

( * ) Notice: Subject to any disclaimer, the term of this patent is extended or adjusted under 35 U.S.C. 154(b) by 74 days.

(21) Appl. No.: 15/369,441

(22) Filed: Dec. 5, 2016

(65) Prior Publication Data

US 2017/0157183 A1    Jun. 8, 2017

(30) Foreign Application Priority Data

Dec. 7, 2015 (TW) .............................. 104140983 A

(51) Int. Cl.
| | |
|---|---|
| *A61K 35/744* | (2015.01) |
| *A61K 35/747* | (2015.01) |
| *A23L 33/135* | (2016.01) |
| *C12N 1/20* | (2006.01) |
| *C12R 1/46* | (2006.01) |
| *C12R 1/225* | (2006.01) |

(52) U.S. Cl.
CPC .......... *A61K 35/744* (2013.01); *A23L 33/135* (2016.08); *A61K 35/747* (2013.01); *C12N 1/20* (2013.01); *C12R 1/225* (2013.01); *C12R 1/46* (2013.01); *A23V 2002/00* (2013.01)

(58) Field of Classification Search
CPC .... A61K 2300/00; A61K 38/00; A61K 35/74; A61K 35/745; A61K 35/747; A61K 31/375; A61K 36/064; A61K 35/744; A61K 2035/115; A61K 2039/505; A61K 31/00; A61K 31/7004; A61K 31/7012; A61K 35/742; A61K 36/28; A61K 35/741; A61K 9/0053; A61K 9/145; A61K 38/17; A61K 38/13; A61K 45/06; A61K 35/37; A61K 9/48; A61K 9/4816; A61K 9/4891; A01N 63/02; A01N 2300/00; A01N 63/00; A23V 2002/00; A23L 33/135; A23L 3/3571; A23L 33/127; A23Y 2220/79; A23Y 2220/05; A23Y 2220/07; A23Y 2280/15; A23B 4/22; A61P 17/00; A61P 17/02; C07K 14/50; C07K 14/503; C07K 14/53; C07K 14/5406; C07K 2319/02; C07K 2319/50; C12N 15/746; C12N 1/20; C12R 1/225; C12R 1/46; Y02A 50/402; Y02A 50/475; Y02A 50/478; Y02A 50/48; Y02A 50/481; Y02A 50/469; Y02A 50/473; A23P 10/30

See application file for complete search history.

(56) References Cited

U.S. PATENT DOCUMENTS 8,541,223 B2 * 9/2013 Tsuboi ................. A23C 9/1234
424/93.45

FOREIGN PATENT DOCUMENTS

| EP | 2112217 A1 | 10/2009 |
| WO | WO2011078781 A1 | 6/2011 |

OTHER PUBLICATIONS

GenBank: CP010050.1, Dec. 23, 2014.
GenBank: KF879109.1, Nov. 30, 2014.
GenBank: AB911506.1, Feb. 26, 2014.
GenBank: AB911465.1, Feb. 26, 2014.
http://newbellus.en.taiwantrade.com/product/probio-o-complex-powder-828315.html, Mar. 17, 2015.

* cited by examiner

*Primary Examiner* — Deborah K Ware
(74) *Attorney, Agent, or Firm* — Ming Chow; Sinorica, LLC

(57) ABSTRACT

Lactic acid bacteria, which are isolated *Lactococcus lactis* subsp. *lactis* LL358 and isolated *Lactobacillus salivarius* LS159 respectively. By administering a composition comprising the lactic acid bacteria of the invention, renal injury, metabolic syndrome, hyperuricemia, hypocalcemia, and other disorders can be effectively ameliorated or treated.

7 Claims, 4 Drawing Sheets

Specification includes a Sequence Listing.

```
GACGAACGCTGGCGGCGTGCCTAATACATGCAAGTTGAGCGCTGAAGGT
TGGTACTTGTACCGACTGGATGAGCAGCGAACGGGTGAGTAACGCGTGG
GGAATCTGCCTTTGAGCGGGGGACAACATTTGGAAACGAATGCTAATAC
CGCATAAAAACTTTAAACACAAGTTTTAAGTTTGAAAGATGCAATTGCAT
CACTCAAAGATGATCCCGCGTTGTATTAGCTAGTTGGTGAGGTAAAGGCT
CACCAAGGCGATGATACATAGCCGACCTGAGAGGGTGATCGGCCACATT
GGGACTGAGACACGGCCCAAACTCCTACGGGAGGCAGCAGTAGGGAAT
CTTCGGCAATGGACGAAAGTCTGACCGAGCAACGCCGCGTGAGTGAAG
AAGGTTTTCGGATCGTAAAACTCTGTTGGTAGAGAAGAACGTTGGTGAG
AGTGGAAAGCTCATCAAGTGACGGTAACTACCCAGAAAGGGACGGCTA
ACTACGTGCCAGCAGCCGCGGTAATACGTAGGTCCCGAGCGTTGTCCGG
ATTTATTGGGCGTAAAGCGAGCGCAGGTGGTTTATTAAGTCTGGTGTAAA
AGGCAGTGGCTCAACCATTGTATGCATTGGAAACTGGTAGACTTGAGTG
CAGGAGAGGAGAGTGGAATTCCATGTGTAGCGGTGAAATGCGTAGATAT
ATGGAGGAACACCGGTGGCGAAAGCGGCTCTCTGGCCTGTAACTGACAC
TGAGGCTCGAAAGCGTGGGGAGCAAACAGGATTAGATACCCTGGTAGTC
CACGCCGTAAACGATGAGTGCTAGATGTAGGGAGCTATAAGTTCTCTGTA
TCGCAGCTAACGCAATAAGCACTCCGCCTGGGGAGTACGACCGCAAGGT
TGAAACTCAAAGGAATTGACGGGGGCCCGCACAAGCGGTGGAGCATGT
GGTTTAATTCGAAGCAACGCGAAGAACCTTACCAGGTCTTGACATACTC
GTGCTATTCCTAGAGATAGGAAGTTCCTTCGGGACACGGGATACAGGTG
GTGCATGGTTGTCGTCAGCTCGTGTCGTGAGATGTTGGGTTAAGTCCCGC
AACGAGCGCAACCCCTATTGTTAGTTGCCATCATTAAGTTGGGCACTCTA
ACGAGACTGCCGGTGATAAACCGGAGGAAGGTGGGGATGACGTCAAAT
CATCATGCCCCTTATGACTTGGGCTACACACGTGCTACAATGGATGGTAC
AACGAGTCGCGAGACAGTGATGTTTAGCTAATCTCTTAAAACCATTCTCA
GTTCGGATTGTAGGCTGCAACTCGCCTACATGAAGTCGGAATCGCTAGTA
ATCGCGGATCAGCACGCCGCGGTGAATACGTTCCCGGGCCTTGTACACA
CCGCCCGTCACACCACGGGAGTTGGGAGTACCCGAAGTAGGTTGCCTAA
CCGCAAGGAGGGCGCTTCCTAAGGTAAGACCGATGACTGGGGTGAAGT
CGTAACAAGGTAGCCGTATCGGAAGGTGC
```

Fig. 3

```
GACGAACGCTGGCGGCGTGCCTAATACATGCAAGTCGAACGAAACTTTCTTACACCG
AATGAAAAGAATTCACCGTAAGAAGTTGAGTGGCGGACGGGTGAGTAACACGTGGGT
AACCTGCCTAAAAGAAGGGGATAACACTTGGAAACAGGTGCTAATACCGTATATCTCT
AAGGATCGCATGATCCTTAGATGAAAGATGGTTCTGCTATCGCTTTTAGATGGACCCGC
GGCGTATTAACTAGTTGGTGGGGTAACGGCCTACCAAGGTGATGATACGTAGCCGAAC
TGAGAGGTTGATCGGCCACATTGGGACTGAGACACGGCCCAAACTCCTACGGGAGGC
AGCAGTAGGGAATCTTCCACAATGGACGCAAGTCTGATGGAGCAACGCCGCGTGAGT
GAAGAAGGTCTTCGGATCGTAAAACTCTGTTGTTAGAGAAGAAACACGAGTGAGAGT
AACTGTTCATTCGATGACGGTATCTAACCAGCAAGTCACGGCTAACTAGGTGCCAGCA
GCCGCGGTAATACGTAGGTGGCAAGCGTTGTCCGGATTTATTGGGCGTAAAGGGAACG
CAGGCGGTCTTTTAAGTCTGATGTGAAAGCCTTCGGCTTAACCGGAGTAGTGCATTGG
AAACTGGAAGACTTGAGTGCAGAAGAGGAGAGTGGAACTCCATGTGTAGCGGTGAA
ATGCGTAGATATATGGAAGAACACCAGTGGCGAAAGCGGCTCTCTGGTCTGTAACTGA
CGCTGAGGTTCGAAAGCGTGGGTAGCAAACAGGATTAGATACCCCTGGTAGTCCACG
CCGTAAACGATGAATGCTAGGTGTTGGAGGGTTTCCGCCCTTCAGTGCCGCAGCTAAC
GCAATAAGCATTCCGCCTGGGGAGTACGACCGCAAGGTTGAAACTCAAAGGAATTGA
CGGGGGCCCGCACAAGCGGTGGAGCATGTGGTTTAATTCGAAGCAACGCGAAGAAC
CTTACCAGGTCTTGACATCCTTTGACCACCTAAGAGATTAGGCTTTCCCTTCGGGGAC
AAAGTGACAGGTGGTGCATGGCTGTCGTCAGCTCGTGTCGTGAGATGTTGGGTTAAG
TCCCGCAACGAGCGCAACCCTTGTTGTCAGTTGCCAGCATTAAGTTGGGCACTCTGGC
GAGACTGCCGGTGACAAACCGGAGGAAGGTGGGGACGACGTCAAGTCATCATGCCC
CTTATGACCTGGGCTACACACGTGCTACAATGGACGGTACAACGAGTCGCGAGACCG
CGAGGTTTAGCTAATCTCTTAAAGCCGTTCTCAGTTCGGATTGTAGGCTGCAACTCGC
CTACATGAAGTCGGAATCGCTAGTAATCGCGAATCAGCATGTCGCGGTGAATACGTTC
CCGGGCCTTGTTCACACCGCCCGTCACACCATGAGAGTTTGTAACACCCAAARCCGG
TGGGGTAACCGCAAGGAGCCAGCCGTCTAAGGTGGGACAGATGATTGGGGTG
```

Fig. 4

SEQUENCE LISTING

<160> NUMBER OF SEQ ID NOS: 2

<210> SEQ ID NO 1
<211> LENGTH: 1502
<212> TYPE: DNA
<213> ORGANISM: Lactococcus lactis subsp. lactis

<400> SEQUENCE: 1

| | | | | | |
|---|---|---|---|---|---|
| gacgaacgct | ggcggcgtgc | ctaatacatg | caagttgagc | gctgaaggtt | ggtacttgta | 60 |
| ccgactggat | gagcagcgaa | cgggtgagta | acgcgtgggg | aatctgcctt | tgagcggggg | 120 |
| acaacatttg | gaaacgaatg | ctaataccgc | ataaaaactt | taaacacaag | ttttaagttt | 180 |
| gaaagatgca | attgcatcac | tcaaagatga | tcccgcgttg | tattagctag | ttggtgaggt | 240 |
| aaaggctcac | caaggcgatg | atacatagcc | gacctgagag | ggtgatcggc | cacattggga | 300 |
| ctgagacacg | gcccaaactc | ctacgggagg | cagcagtagg | gaatcttcgg | caatggacga | 360 |
| aagtctgacc | gagcaacgcc | gcgtgagtga | agaaggtttt | cggatcgtaa | aactctgttg | 420 |
| gtagagaaga | acgttggtga | gagtggaaag | ctcatcaagt | gacggtaact | acccagaaag | 480 |
| ggacggctaa | ctacgtgcca | gcagccgcgg | taatacgtag | gtcccgagcg | ttgtccggat | 540 |
| ttattgggcg | taaagcgagc | gcaggtggtt | tattaagtct | ggtgtaaaag | gcagtggctc | 600 |
| aaccattgta | tgcattggaa | actggtagtc | ttgagtgcag | gagaggagag | tggaattcca | 660 |
| tgtgtagcgg | tgaaatgcgt | agatatatgg | aggaacaccg | gtggcgaaag | cggctctctg | 720 |
| gcctgtaact | gacactgagg | ctcgaaagcg | tggggagcaa | acaggattag | ataccctggt | 780 |
| agtccacgcc | gtaaacgatg | agtgctagat | gtagggagct | ataagttctc | tgtatcgcag | 840 |
| ctaacgcaat | aagcactccg | cctggggagt | acgaccgcaa | ggttgaaact | caaaggaatt | 900 |
| gacggggggcc | cgcacaagcg | gtggagcatg | tggtttaatt | cgaagcaacg | cgaagaacct | 960 |
| taccaggtct | tgacatactc | gtgctattcc | tagagatagg | aagttccttc | gggacacggg | 1020 |
| atacaggtgg | tgcatggttg | tcgtcagctc | gtgtcgtgag | atgttgggtt | aagtcccgca | 1080 |
| acgagcgcaa | cccctattgt | tagttgccat | cattaagttg | ggcactctaa | cgagactgcc | 1140 |
| ggtgataaac | cggaggaagg | tggggatgac | gtcaaatcat | catgccccctt | atgacctggg | 1200 |
| ctacacacgt | gctacaatgg | atggtacaac | gagtcgcgag | acagtgatgt | ttagctaatc | 1260 |
| tcttaaaacc | attctcagtt | cggattgtag | gctgcaactc | gcctacatga | agtcggaatc | 1320 |
| gctagtaatc | gcggatcagc | acgccgcggt | gaatacgttc | ccgggccttg | tacacaccgc | 1380 |
| ccgtcacacc | acgggagttg | ggagtacccg | aagtaggttg | cctaaccgca | aggagggcgc | 1440 |
| ttcctaaggt | aagaccgatg | actggggtga | agtcgtaaca | aggtagccgt | atcggaaggt | 1500 |
| gc | | | | | | 1502 |

<210> SEQ ID NO 2
<211> LENGTH: 1487
<212> TYPE: DNA
<213> ORGANISM: Lactobacillus salivarius

<400> SEQUENCE: 2

| | | | | | |
|---|---|---|---|---|---|
| gacgaacgct | ggcggcgtgc | ctaatacatg | caagtcgaac | gaaactttct | tacaccgaat | 60 |
| gaaaagaatt | caccgtaaga | agttgagtgg | cggacgggtg | agtaacacgt | gggtaacctg | 120 |
| cctaaaagaa | ggggataaca | cttggaaaca | ggtgctaata | ccgtatatct | ctaaggatcg | 180 |
| catgatcctt | agatgaaaga | tggttctgct | atcgcttttta | gatggacccg | cggcgtatta | 240 |
| actagttggt | ggggtaacgg | cctaccaagg | tgatgatacg | tagccgaact | gagaggttga | 300 |

```
tcggccacat tgggactgag acacggccca aactcctacg ggaggcagca gtagggaatc      360
ttccacaatg gacgcaagtc tgatggagca acgccgcgtg agtgaagaag gtcttcggat      420
cgtaaaactc tgttgttaga gaagaaacac gagtgagagt aactgttcat tcgatgacgg      480
tatctaacca gcaagtcacg gctaactagg tgccagcagc cgcggtaata ggtaggtggc      540
aagcgttgtc cggatttatt gggcgtaaag ggaacgcagg cggtcttta agtctgatgt      600 gaaagccttc ggcttaaccg gagtagtgca ttggaaactg gaagacttga gtgcagaaga      660
ggagagtgga actccatgtg tagcggtgaa atgcgtagat atatggaaga acaccagtgg      720
cgaaagcggc tctctggtct gtaactgacg ctgaggttcg aaagcgtggg tagcaaacag      780
gattagatac ccctggtagt ccacgccgta aacgatgaat gctaggtgtt ggagggtttc      840
cgcccttcag tgccgcagct aacgcaataa gcattccgcc tggggagtac gaccgcaagg      900
ttgaaactca aaggaattga cgggggcccg cacaagcggt ggagcatgtg gtttaattcg      960
aagcaacgcg aagaacctta ccaggtcttg acatcctttg accacctaag agattaggct     1020
ttcccttcgg ggacaaagtg acaggtggtg catggctgtc gtcagctcgt gtcgtgagat     1080
gttgggttaa gtcccgcaac gagcgcaacc cttgttgtca gttgccagga ttaagttggg     1140
cactctggcg agactgccgg tgacaaaccg gaggaaggtg gggacgacgt caagtcatca     1200
tgccccttat gacctgggct acacacgtgc tacaatggac ggtacaacga gtcgcgagac     1260
cgcgaggttt agcataatct cttaaagccg ttctcagttc ggattgtagg ctgcaactcg     1320
cctacatgaa gtcggaatcg ctagtaatcg cgaatcagca tgtcgcggtg aatacgttcc     1380
cgggccttgt tcacaccgcc cgtcacacca tgagatttgt aacacccaaa rccggtgggg     1440
taaccgcaag gagccagccg tctaaggtgg gacagatgat tggggtg                   1487
```

LACTIC ACID BACTERIA AND USE THEREOF

TECHNICAL FIELD

The present invention relates to probiotics, and particularly to novel lactic acid bacteria and use thereof.

PRIOR ART

The chronic kidney disease is classified into 5 stages according to the estimated Glomerular Filtration Rate (eGFR) and the injury to the kidney, where in stages 1-2 (eGFR>60 mL/min/1.73 $m^2$), no obvious symptoms are present; in stages 3-4 (eGFR 15-60 mL/min/1.73 $m^2$), mild or moderate anaemia, fatigue, edema, and itchy skin occur, so that the chronic kidney disease has generally been progressed to stages 3-4 when the symptoms are manifested; and in stage 5 (eGFR<15 mL/min/1.73 $m^2$), moderate or severe anaemia, edema, and inappetence take place. Generally, the patients in stage 3 or higher need to be treated with drugs actively, and dialysis treatment is necessitated in case of persistent deterioration.

It can be known from the statistical data above that the chronic kidney disease causes a threat to personal health, and also the high expense for treating chronic kidney disease becomes a family, social and national issue.

Although treatment with drugs can greatly control and slow down the progression of chronic kidney disease, the side effects of the drugs makes the patients incompliant. The problem generally encountered during the treatment of chronic kidney disease is that most of the patients with stages 3-4 chronic kidney disease do not receive any or consecutive treatment with drugs, such that the chronic kidney disease is deteriorated rapidly into end-stage renal disease, which can only be treated by dialysis. This not only has a great impact on the quality of life and health condition of the patients, but also causes a heavy burden to the family and society.

Lactic acid bacteria are microorganisms able to produce lactic acid through fermentation of hydrocarbons. It is confirmed in literatures that lactic acid bacteria have a variety of healthcare effects for human, including maintaining the intestinal microflora, increasing the immune function, improving the metabolism, and others. Therefore, lactic acid bacteria are considered to be vital probiotics in the intestinal microflora. Wastes are failed to be cleared from the patients with chronic kidney disease frequently due to the loss of normal kidney function, such that toxins such as uremic substances enter the body through the gastrointestinal tract, thereby affecting the health of patients. Therefore, recent studies are focused on exploration of the use of lactic acid bacteria in improvement of the renal functions, and it is expected to obtain a method for effectively delay or treat chronic kidney disease.

SUMMARY OF THE INVENTION

The present invention mainly aims at providing a novel lactic acid bacterium, which is isolated Accession Number, deposited in Institute of Microbiology Chinese Academy of Science (China) under Accession Number CGMCC 13317, on 2016/11/18. *Lactococcus lactis* subsp. *lactis* LL358 is also deposited in Food Industry Research and Development Institute (Taiwan) under Accession Number BCRC910699, on 2015/9/4.

The present invention further aims at providing a novel lactic acid bacterium, which is isolated *Lactobacillus salivarius* L5159, deposited in Institute of Microbiology Chinese Academy of Science (China) under Accession Number CGMCC 13316, on 2016 Nov. 18. *Lactobacillus salivarius* L5159 is also deposited in Food Industry Research and Development Institute (Taiwan) under Accession Number BCRC910700, on 2015 Sep. 4.

The novel lactic acid bacteria are isolated from pickles, and are a Gram positive bacterium which have no catalyst, but have an oxidase and mobility, produce no endospores, and are able to grow in aerobic and anaerobic environments and allowed to be cultured in a *Lactobacillus* MRS medium at a temperature of 37° C.

The present invention further aims at providing a composition, which comprises at least the novel lactic acid bacteria, and can modify the occurrence or delay the progression of a diseases when administered in an effective amount to a subject.

In an embodiment of the present invention, the composition disclosed in the present invention comprises at least one of *Lactococcus lactis* subsp. *Lactis* LL358 CGMCC 13317, *Lactobacillus salivarius* LS159 CGMCC 13316, and *Lactobacillus pentosus*. Preferably, the composition comprises *Lactococcus lactis* subsp. *lactis* LL358, *Lactobacillus salivarius* LS159, and *Lactobacillus pentosus*.

In an embodiment of the present invention, the composition is a pharmaceutical composition.

In an embodiment of the present invention, the composition is a dietary supplement.

The composition is provided for treating or preventing chronic kidney disease in a subject suffering from the chronic kidney disease. That is, the use in maintaining the renal function of the impaired kidney, treating and/or preventing metabolic syndrome and its signs, preventing hyperuricemia, and ameliorating and/or preventing hypocalcemia, as well as in slowing down or avoiding symptoms elicited by chronic kidney disease, reducing the mortality, maintaining a good quality of life, and delaying the deterioration of the kidney disease can be achieved, by administering effective amount of the composition to the subject.

Preferably, the composition can be prepared into various forms as desired by the consumer, for example, a solid state, a liquid state, a powder, tablets, or a gel; or be processed into various products, for example, food, food additives, and beverages.

BRIEF DESCRIPTION OF THE DRAWINGS

FIG. 3 shows a 16S rDNA sequence of *Lactococcus lactis* subsp. *lactis* LL358.

FIG. 4 shows a 16S rDNA sequence of *Lactobacillus salivarius* LS159.

DETAILED DESCRIPTION

Unless otherwise defined, the technical and scientific terms used in the specification and claims have the same meanings as those generally understood by persons of ordinary skill in the art to which the present invention pertains. In case of contradiction, the present invention shall prevail.

The term "pharmaceutical composition" as used herein comprises an effective amount of a desired compound or active ingredient intended for producing a particular effect, and/or at least a pharmaceutically acceptable carrier. It can be appreciated by those ordinarily skilled in the art to which the present invention pertains that the form of the pharmaceutical composition varies with the route of administration intended for producing a particular effect, including, for example, tablets, powders and injections; and the carrier can be in a solid state, a semi-solid state or a liquid state, depending on the form of the pharmaceutical composition. For example, the carrier includes, but is not limited to, gelatin, an emulsifier, a hydrocarbon mixture, water, glycerin, saline, buffered saline, lanolin, paraffin, beeswax, dimethylsilicone, and ethanol.

The term "effective amount" as used herein refers to an amount of the desired compound or active ingredient intended for producing a particular effect, and expressed in percentages by weight present in the composition. It can be appreciated by those ordinarily skilled in the art to which the present invention pertains that the effective amount varies with the route of administration intended for eliciting a particular effect. Generally, the amount of the active ingredient or compound in the composition may account for about 1% to about 100%, and preferably about 30% to about 100% by weight of the composition.

The term "pharmaceutically acceptable carrier" as used herein is one which is compatible with the active ingredient in the pharmaceutical composition and preferably enhances the stability of the pharmaceutical composition, and is non-hazardous to the subject. The pharmaceutically acceptable carrier varies with the dosage form, including, but not limited to, corn starch, lactose, cellulose, magnesium stearate, colloidal silica, maltodextrin, water, and so on.

Hereinafter, for the purpose of further explaining the efficacy of the present invention, the present invention is described in detail by way of examples. However, the examples are illustrative and any language used therein is not intended to limit the specification and the scope and meaning of the claims of the present invention.

Example 1: Strain Isolation and Identification

Figure 1:
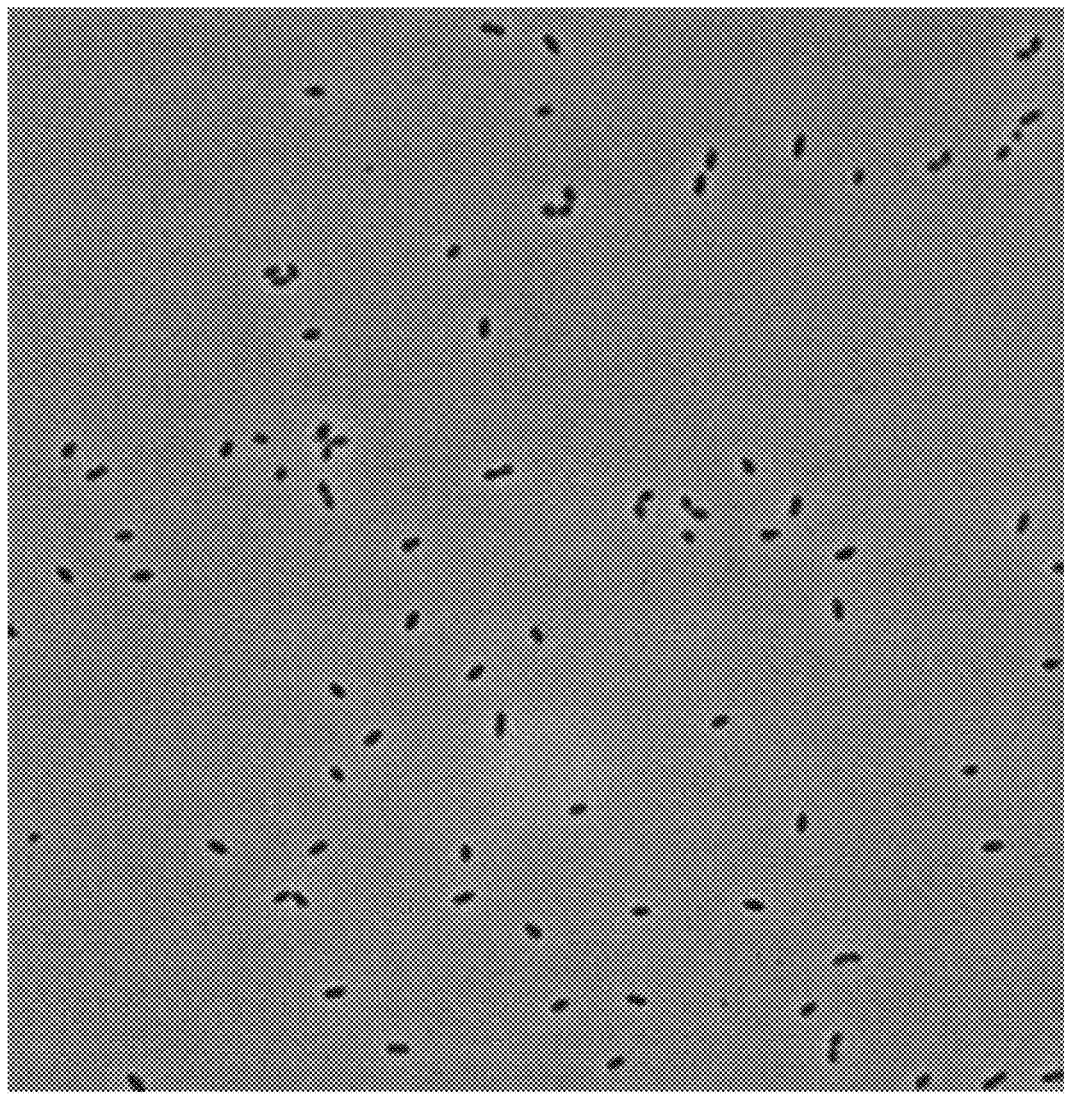
FIG. 1 shows *Lactococcus lactis* subsp. *lactis* LL358 observed under a microscope.
Figure 2:
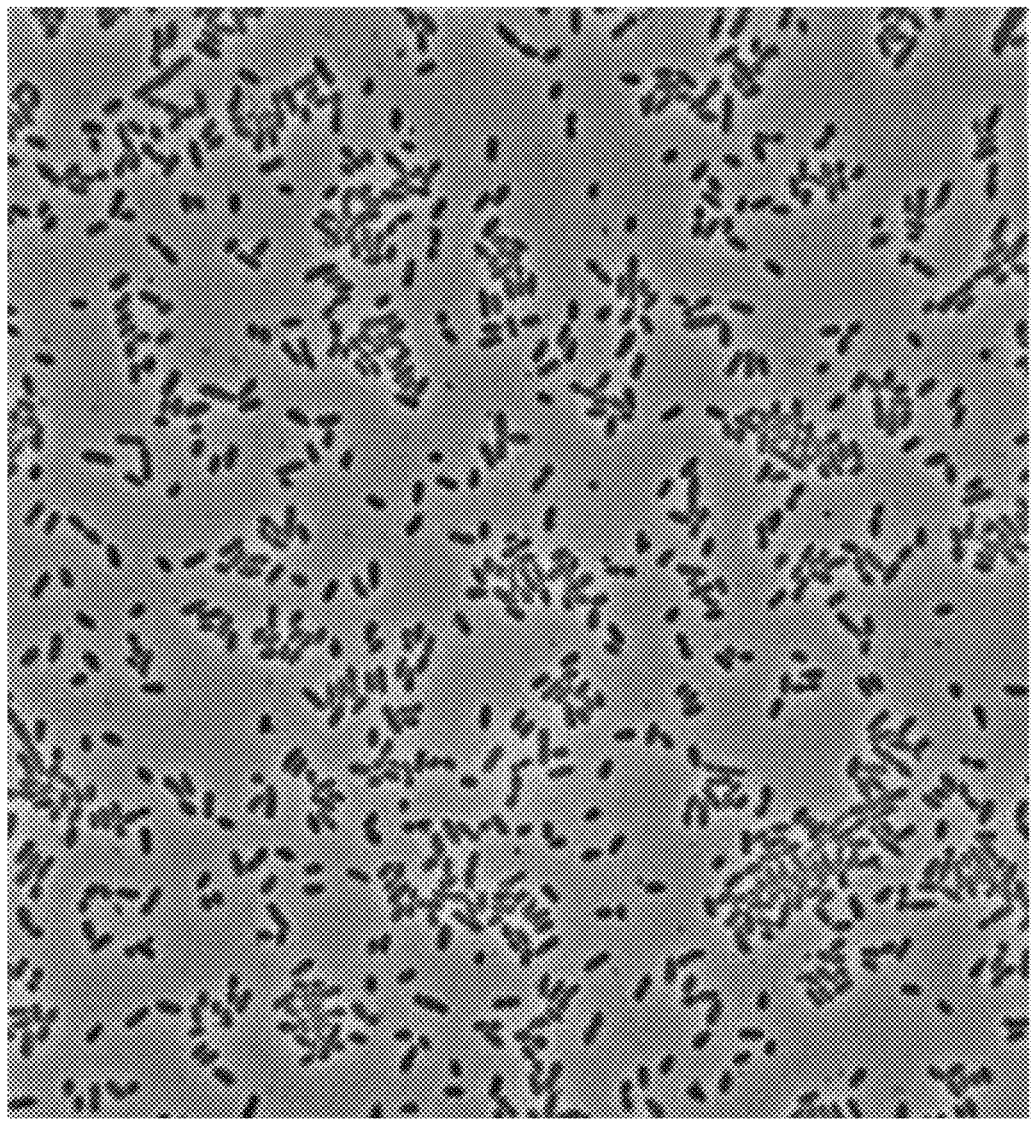
FIG. 2 shows *Lactobacillus salivarius* LS159 observed under a microscope.

*Lactococcus lactis* subsp. *lactis* LL358, and *Lactobacillus salivarius* L5159 are isolated from vegetable pickles, which are as shown in FIGS. 1 and 2.

It can be known from the result of identification by Food Industry Research and Development Institute (Taiwan) that *Lactococcus lactis* subsp. *lactis* LL358 and *Lactobacillus salivarius* L5159 are characterized in that they are Gram positive bacteria, have no catalyst, but have an oxidase and mobility, produce no endospores, and are able to grow in aerobic and anaerobic environments and allowed to be cultured in a *Lactobacillus* MRS medium at a temperature of 37° C.

Referring to FIG. 3, the 16S rDNA sequence of *Lactococcus lactis* subsp. *lactis* LL358 is as shown in SEQ ID No. 1. Based on 16S rDNA sequencing, it can be known that *Lactococcus lactis* subsp. *lactis* LL358 has 98% or more similarity to *Lactococcus lactis* subsp. *lactis, Lactococcus lactis* subsp. *hordniae, Lactococcus lactis* subsp. *tructae, Lactococcus lactis* subsp. *Cremoris*, and *Lactococcus lactis* subsp. *Taiwanensis*. It is confirmed by API microbial identification system that *Lactococcus lactis* subsp. *lactis* LL358 is mostly closest to *Lactococcus lactis* subsp. *lactis*. Therefore, the identification result shows that *Lactococcus lactis* subsp. *lactis* LL358 is a new strain of *Lactococcus lactis* subsp. *lactis*.

Referring to FIG. 4, the 16S rDNA sequence of *Lactobacillus salivarius* LS159 is as shown in SEQ ID No. 2. Based on 16S rDNA sequencing, it can be known that *Lactobacillus salivarius* L5159 has up to 99.4% similarity to *Lactobacillus salivarius*. It is confirmed by API microbial identification system that *Lactobacillus salivarius* LS159 is mostly closest to *Lactobacillus salivarius*. Therefore, the identification result shows that *Lactobacillus salivarius* L5159 is a new strain of *Lactobacillus salivarius*.

Example 2: Preparation of Lactic Acid Bacteria Containing Composition

*Lactococcus lactis* subsp. *lactis* LL358 and *Lactobacillus salivarius* L5159 obtained in Example 1 were mixed with *Lactobacillus pentosus* to prepare a lactic acid bacteria containing composition, where the proportion of *Lactococcus lactis* subsp. *lactis* LL358, *Lactobacillus salivarius* LS159, and *Lactobacillus pentosus* was 1:1:1.

Example 3: Test in Human

It should be noted that this test was examined and approved by the Member of Institutional Review Board, Tungs' Taichung MetroHarbor Hospital, Taiwan (IRB No. TTMH: 102023).

A total of 80 patients with stages 3 and 4 chronic kidney disease were screened out in out-patient clinic, department of nephrology, Tungs' Taichung MetroHarbor Hospital, 29 patients dropped out from the test due to personal reasons, and the remaining patients signed the information consent form and became a subject.

The subjects were randomized to a test group and a placebo group. The subjects in the test group were each given a pack of the lactic acid bacteria containing composition (3 g/pack, and having a total bacterial count of $1 \times 10^{11}$ CFU/pack) at the morning and evening every day, and the subjects in the placebo group were given equal dosage of resistant starch at the morning and evening. During the test (weeks 0 to 12) and 4-week (weeks 13 to 16) follow-up after withdrawal, the subjects were still administered with the prescribed drugs and continued the original diet, and collected for basic data, blood and urine specimens, and gastrointestinal symptoms rating scale for analysis respectively at weeks 0, 12, and 16 (that is, 4 weeks after withdrawal).

A total of 41 subjects completed the test, of which 26 had stage 3 chronic kidney disease, and 15 had stage 4 chronic kidney disease, and the average age was 60.32±8.26 years. The subjects had estimated Glomerular Filtration Rate (eGFR) of 44.74±8.65 ml/min/1.73 $m^2$ and 43.53±8.55 ml/min/1.73 $m^2$, and 22.85±3.81 ml/min/1.73 $m^2$ and 21.73±3.65 ml/min/1.73 $m^2$, by using Modification of Diet in Renal Disease (MDRD) formula and by using Chronic Kidney Disease Epidemiology Collaboration (CKD-EPI) formula respectively.

Example 4: Physical Condition Analysis

The body condition data of the 41 subjects who had completed the test is shown in Tables 1 and 2 below. Tables 1 and 2 compare the difference between the two groups by Chi-square test, and the values are expressed as numbers and percentages. Except for genders, the difference between the two groups is compared by 2-Independent-Samples t-test, and the values are expressed as mean, standard deviation, and minimum-maximum. In the tables, the symbol "#" indicates that there is significant difference between those with different genders or with different courses of disease in the same group (p<0.05); and the symbol "*" indicates that there is significant difference between different groups (p<0.05). It can be known from the statistical results in Table 1 that the patients with stages 3 and 4 chronic kidney disease have a BMI values of 27.98±5.62 kg/m2 and 27.03±4.00 kg/m2 respectively, and they are all of obesity (BMI value 27 kg/m2). The average body fat percentage of these subjects is 29.55±5.79%, which is close to the obesity standard for women (body fat percentage of 30%); and the average visceral fat percentage is 16.16±7.24%, which is greater than the standard (12%). Moreover, the waist circumference, hip circumference and waist-hip ratio of the patients with stage 3 chronic kidney disease are all higher than those of the patients with stage 4 chronic kidney disease, and the average waist circumferences of the male and female patients are 96.06±11.75 cm and 95.79±14.22 cm respectively, which are both larger than the standards for metabolic syndrome (male ≥90 cm, and female ≥80 cm).

Further, Tables 3 and 4 compare the difference between the two groups by Wilcoxon rank-sum test, and the values are expressed as mean, standard deviation, and minimum-maximum. In the tables, the symbol "*" indicates that there is significant difference between different groups (p<0.05); and the symbol "#" indicates that there is difference between those with different courses of disease in the same group (p<0.05).

It can be known from Tables 3 and 4 that before test, the mean waist circumference and waist-hip ratio of the patients in the test group and the placebo group are 95.67±14.79 and 97.00±10.52 cm, and 0.96±0.08 and 0.98±0.06 respectively. It can be found through comparison of the subjects in the test group and the placebo group that there is no significant difference between the body conditions in terms of the body weight, BMI, body fat ratio, visceral fat ratio, subcutaneous body fat percentage, total body skeletal muscle, waist circumference, and waist-hip ratio (P>0.05), prior to and post test. However, the patients with stage 4 chronic kidney disease in the test group have obviously reduced visceral fat percentage during the test, as compared with the patients in the placebo group.

TABLE 1

Basic data and body condition analysis of all the subjects before test

|  | Mean | Standard Deviation (SD) | Range |
|---|---|---|---|
| Sex (n, %) |  |  |  |
| Male | 33 | 80.5# |  |
| Female | 8 | 19.5 |  |
| Age (years) | 61.32 | 8.26 | 44-75 |
| High (cm) | 162.64 | 7.02 | 150-180 |
| Weight (kg) | 73.39 | 15.40 | 45.3-116.8 |
| BMI, (kg/m$^2$) | 27.66 | 5.08 | 18.5-40.5 |
| Body fat ratio (%) | 29.46 | 6.55 | 16.3-44.4 |
| visceral fat ratio (%) | 15.13 | 6.63 | 3-30 |
| subcutaneous body fat percentage (%) | 20.87 | 8.07 | 4-43.4 |
| total body skeletal muscle (%) | 28.21 | 5.29 | 20.3-49.4 |
| waist circumference (cm) | 96.26 | 12.95 | 73-128 |
| Hip circumference (cm) | 99.49 | 8.11 | 84-120 |
| waist-hip ratio | 0.96 | 0.07 | 0.84-1.13 |

TABLE 2

Basic data and body condition analysis of subjects with stages 3 and 4 chronic kidney disease before test

|  | stage 3 (n = 26) | | | stage 4 (n = 15) | | |
|---|---|---|---|---|---|---|
|  | Mean | SD | Range | Mean | SD | Range |
| Sex (n, %) |  |  |  |  |  |  |
| Male | 24 | (92.3)# |  | 9 | (60.0)* |  |
| Female | 2 | (7.7) |  | 6 | (40.0) |  |
| Age(years) | 61.31 | 7.68 | 45-74 | 61.33 | 9.47 | 44-75 |
| High(cm) | 163.02 | 7.19 | 150-180 | 161.92 | 6.90 | 153-172 |
| Weight(kg) | 74.74 | 17.42 | 45.3-116.8 | 70.78 | 10.65 | 51-92.1 |
| BMI, (kg/m$^2$) | 27.98 | 5.62 | 18.5-40.5 | 27.03 | 4.00 | 21.8-37.4 |
| Body fat ratio (%) | 29.55 | 5.79 | 16.3-41.1 | 29.28 | 8.07 | 18.3-44.4 |
| visceral fat ratio (%) | 16.16 | 7.24 | 3-30 | 13.15 | 4.93 | 4-25 |
| subcutaneous body fat percentage (%) | 21.18 | 6.55 | 10-40.1 | 20.28 | 10.68 | 4-43.4 |
| total body skeletal muscle (%) | 26.92 | 2.87 | 21.8-31.7 | 30.68 | 7.74 | 20.3-49.4 |
| waist circumference(cm) | 97.08 | 13.38 | 73-128 | 94.83 | 12.50 | 77-122 |
| Hip circumference(cm) | 99.21 | 8.87 | 84-120 | 99.97 | 6.85 | 90-113 |
| waist-hip ratio | 0.98 | 0.07 | 0.87-1.13 | 0.95 | 0.07 | 0.84-1.08 |

TABLE 3

Body condition analysis of all the subjects during weeks 0 to 16 of the test

|  | Test group | | Placebo group | |
|---|---|---|---|---|
|  | Mean | SD | Mean | SD |
| Weight |  |  |  |  |
| Week 0 | 72.49 | 16.88 | 74.49 | 13.80 |
| Week 12 | 72.93 | 17.31 | 75.59 | 14.47 |
| Week 16 | 72.64 | 17.46 | 74.43 | 13.96 |
| BMI |  |  |  |  |
| Week 0 | 27.38 | 5.00 | 27.99 | 5.31 |
| Week 12 | 27.53 | 5.19 | 28.01 | 5.14 |
| Week 16 | 27.47 | 5.18 | 28.04 | 5.31 |

TABLE 3-continued

Body condition analysis of all the subjects during weeks 0 to 16 of the test

|  | Test group | | Placebo group | |
|---|---|---|---|---|
|  | Mean | SD | Mean | SD |
| Body fat ratio | | | | |
| Week 0 | 29.00 | 6.64 | 30.02 | 6.58 |
| Week 12 | 29.35 | 6.35 | 29.68 | 6.11 |
| Week 16 | 29.32 | 6.50 | 29.99 | 6.58 |
| visceral fat ratio | | | | |
| Week 0 | 14.71 | 7.40 | 15.65 | 5.71 |
| Week 12 | 15.00 | 7.52 | 16.12 | 5.38 |
| Week 16 | 15.05 | 7.58 | 16.13 | 5.64 |
| waist circumference | | | | |
| Week 0 | 95.67 | 14.79 | 97.00 | 10.52 |
| Week 12 | 95.85 | 14.55 | 97.21 | 10.24 |
| Week 16 | 95.83 | 14.53 | 96.69 | 10.41 |
| Hip circumference | | | | |
| Week 0 | 99.54 | 8.27 | 99.42 | 8.14 |
| Week 12 | 99.70 | 8.03 | 100.03 | 7.94 |
| Week 16 | 99.83 | 7.91 | 99.69 | 8.10 |
| waist-hip ratio | | | | |
| Week 0 | 0.96 | 0.08 | 0.98 | 0.06 |
| Week 12 | 0.96 | 0.08 | 0.97 | 0.06 |
| Week 16 | 0.96 | 0.08 | 0.97 | 0.06 |

TABLE 4

Body condition analysis of subjects with stages 3 and 4 chronic kidney disease during weeks 0 to 16 of the test

|  | stage 3 | | | | stage 4 | | | |
|---|---|---|---|---|---|---|---|---|
|  | Test group | | Placebo group | | Test group | | Placebo group | |
|  | Mean | SD | Mean | SD | Mean | SD | Mean | SD |
| Weight | | | | | | | | |
| Week 0 | 76.44 | 20.36 | 73.17 | 14.89 | 67.22 | 9.36 | 78.80 | 9.81 |
| Week 12 | 77.29 | 20.58 | 74.48 | 15.69 | 67.11 | 10.01 | 79.20 | 10.46 |
| Week 16 | 77.03 | 20.77 | 72.70 | 14.50 | 66.78 | 10.04 | 81.90 | 9.80 |
| BMI | | | | | | | | |
| Week 0 | 28.49 | 6.01 | 27.51 | 5.43 | 25.90 | 2.94 | 29.58 | 5.33 |
| Week 12 | 28.80 | 6.16 | 27.52 | 5.17 | 25.83 | 3.08 | 29.60 | 5.46 |
| Week 16 | 28.78 | 6.11 | 27.33 | 5.29 | 25.72 | 3.11 | 31.10 | 5.14 |
| Body fat ratio | | | | | | | | |
| Week 0 | 29.49 | 5.79 | 29.60 | 6.02 | 28.34 | 7.97 | 31.40 | 9.09 |
| Week 12 | 29.70 | 5.35 | 28.99 | 5.59 | 28.89 | 7.80 | 31.90 | 8.09 |
| Week 16 | 30.00 | 5.62 | 29.41 | 6.01 | 28.41 | 7.78 | 32.50 | 9.82 |
| visceral fat ratio | | | | | | | | |
| Week 0 | 17.33 | 8.55[#] | 15.08 | 5.92 | 11.22 | 3.53 | 17.50 | 5.26* |
| Week 12 | 17.92 | 8.50[#] | 15.77 | 5.80 | 11.11 | 3.52 | 17.25 | 4.19* |
| Week 16 | 17.92 | 8.62[#] | 15.46 | 5.84 | 11.22 | 3.56 | 19.00 | 4.36* |
| waist circumference | | | | | | | | |
| Week 0 | 99.13 | 17.07 | 95.32 | 9.50 | 91.91 | 11.43 | 102.88 | 13.27 |
| Week 12 | 99.25 | 16.72 | 95.50 | 9.67 | 92.14 | 11.36 | 102.75 | 11.50 |
| Week 16 | 99.25 | 16.81 | 95.15 | 9.44 | 92.09 | 11.15 | 103.33 | 14.01 |
| Hip circumference | | | | | | | | |
| Week 0 | 100.08 | 9.73 | 98.46 | 8.37 | 98.96 | 6.74 | 102.75 | 7.32 |
| Week 12 | 100.21 | 9.44 | 99.31 | 8.47 | 99.14 | 6.57 | 102.38 | 6.29 |
| Week 16 | 100.38 | 9.33 | 99.12 | 8.38 | 99.23 | 6.40 | 102.17 | 7.69 |
| waist-hip ratio | | | | | | | | |
| Week 0 | 0.98 | 0.09 | 0.97 | 0.06 | 0.93 | 0.06 | 1.00 | 0.06 |
| Week 12 | 0.99 | 0.09 | 0.96 | 0.06 | 0.93 | 0.06 | 1.00 | 0.05 |
| Week 16 | 0.98 | 0.09 | 0.96 | 0.06 | 0.93 | 0.06 | 1.01 | 0.06 |

Example 5: Blood Pressure Analysis

Tables 5 and 6 compare the difference between the two groups by Wilcoxon rank-sum test, and the values are expressed as mean, standard deviation, and minimum-maximum. The mean systolic and diastolic blood pressure, pulse rate and mean arterial pressure of the 41 subjects measured before test are 136.56±15.04 mmHg, 84.66±9.98 mmHg, 79.56±11.61 pulse/min, and 101.96±10.35 mmHg respectively. Subjects with stage 4 chronic kidney disease have a mean systolic blood pressure of 138.33±15.57 mmHg and a pulse rate of 80.27±11.39 pulse/min, which are higher than the mean systolic blood pressure of 135.54±14.93 mmHg and the pulse rate of 79.15±11.65 pulse/min of the subjects with stage 3 chronic kidney disease.

Tables 7 and 8 compare the difference between the two groups by Wilcoxon rank-sum test, and the values are expressed as mean, standard deviation, and minimum-maximum. It can be known from Tables 7 and 8 that the patients in both the placebo group and the test group have a systolic blood pressure and pulse rate that are higher than the standards for metabolic syndrome (130 mmHg, and 72 pulse/min), and have a diastolic blood pressure and a mean arterial pressure falling in a normal range (85 mmHg, and 80-95 mmHg). Moreover, there is no significant difference between the test group and the placebo group before test ($P>0.05$).

At week 12 of the test, the systolic blood pressure is measured. The systolic blood pressure of the subjects in the test group is increased by 1.61 mmHg, and the systolic blood pressure of the subjects in the placebo group is increased by 3.65 mmHg. At week 16 of the test, the systolic blood pressure of the subjects in the test group is decreased by 4.57 mmHg. This suggests that administration of the lactic acid bacteria containing composition according to the present invention results in a reduced elevation in the systolic blood pressure, and is still effective in controlling and reducing the systolic blood pressure after withdrawal.

Moreover, at week 12 of the test, the systolic blood pressure of the subjects with stage 4 chronic kidney disease in the test group is decreased by 0.73 mmHg, which is higher than the decrease (3.75±17.52 mmHg) in the systolic blood pressure of the subjects with stage 3 chronic kidney disease. Furthermore, after 4-week withdrawal, the systolic blood pressure of the subjects with stages 3 and 4 chronic kidney disease in the test group trends to further decrease, and is reduced by 6.64±10.63 and 2.67±18.62 mmHg respectively. In contrast, at week 12 of the test, the systolic blood pressure of the subjects with stages 3 and 4 chronic kidney disease in the placebo group is increased by 3.75±6.99 and 3.62±9.24 mmHg respectively. Furthermore, after 4-week withdrawal, the increase (1.15 mmHg) in the systolic blood pressure in the subjects with stage 3 chronic kidney disease is higher than that in the subjects with stage 4 chronic kidney disease (−2.33 mmHg).

At week 12 of the test, the diastolic blood pressure of the subjects in the test group is decreased by 1.09 mmHg on average, and the diastolic blood pressure of the subjects in the placebo group is decreased by 1.41 mmHg on average. The diastolic blood pressure of the subjects with stage 3 chronic kidney disease in the test group is decreased by 2.33 mmHg on average, which is advantageous over the average decrease (1.77 mmHg) in the diastolic blood pressure of the subjects with stage 3 chronic kidney disease in the placebo group. After 4-week withdrawal, the diastolic blood pressure of the subjects in the placebo group is increased by 1.56 mmHg on average, which is 3 times of the increase (0.39 mmHg) in the diastolic blood pressure of the subjects in the test group. Moreover, the diastolic blood pressure of the subjects with stage 4 chronic kidney disease in the test group is further decreased by 2.33 mmHg, which is approximately 3 times higher than the decrease in the subjects with stage 4 chronic kidney disease in the placebo group.

With respect to the mean arterial pressure, at weeks 12 and 16 of the test, the mean arterial pressure of the subjects in the test group is decreased by 0.19±12.46 and 0.71±10.22 mmHg respectively, and the mean arterial pressure of the subjects in the placebo group is increased by 0.27±7.55 and 1.21±7.03 mmHg respectively. The mean arterial pressure of the subjects with stages 3 and 4 chronic kidney disease in the test group trends to decrease after week 12 of the test, and is decreased by 0.3±13.00 and 0.06±12.43 mmHg respectively.

At week 12 of the test, the variation in pulse rate of the subjects in the placebo group is 0.12 pulse/min, which is approximately 2 times higher than that in the test group (−1.57 pulse/min). The decrease (−2.08 pulse/min) in the pulse rate of the subjects with stage 3 chronic kidney disease in the test group is higher than that (−1.00 pulse/min) of the subjects with stage 4 chronic kidney disease; and at week 16 of the test, the decrease (−4.45 pulse/min) in the pulse rate of the subjects with stage 4 chronic kidney disease in the test group is higher than that (0.08 pulse/min) of the subjects with stage 3 chronic kidney disease.

Tables 9 and 10 compare the difference between the two groups by Fisher's exact test, and the values are expressed as numbers (percentages). At weeks 12 and 16 of the test, the percentages of persons with reduced pulse rate among the subjects with stages 3 and 4 chronic kidney disease in the test group are 41.67% and 41.67%, and 45.45% and 54.55% respectively. It can be known from further analysis that at week 12 of the test, over 50% of the subjects with stage 3 chronic kidney disease in the test group have a systolic blood pressure, a diastolic blood pressure, and a mean arterial pressure decreased by more than 2 mmHg; and at week 16 of the test, over 50% of the subject still have a persistently decreased systolic blood pressure and mean arterial pressure (50% and 58%), and the decreases are higher than those in the placebo group. Compared with the placebo group, more subjects with stage 4 chronic kidney disease in the test group have a more profound decrease in the systolic blood pressure, the diastolic blood pressure and the mean arterial pressure.

It can be known from above data that administration of the lactic acid bacteria containing composition disclosed in the present invention can effectively reduce the systolic blood pressure, the diastolic blood pressure, and the mean arterial pressure in patients with chronic kidney disease, and has a better improvement effect in terms of the reduction in the systolic blood pressure, the mean arterial pressure and the pulse of the patients with stage 4 chronic kidney disease.

TABLE 5

Blood and pulse rate of all the subjects before test

|  | Mean | SD | Range |
|---|---|---|---|
| Systolic pressure (mmHg) | 136.56 | 15.04 | 108-172 |
| diastolic blood pressure (mmHg) | 84.66 | 9.98 | 60-111 |

TABLE 5-continued

Blood and pulse rate of all the subjects before test

| | Mean | SD | Range |
|---|---|---|---|
| mean arterial pressure (mmHg) | 101.96 | 10.30 | 84-131.33 |
| pulse (pulse/min) | 79.56 | 11.61 | 54-106 |

TABLE 6

Blood and pulse rate of subjects with stages 3 and 4 chronic kidney disease before test

| | stage 3 (n = 26) | | | stage 4 (n = 15) | | |
|---|---|---|---|---|---|---|
| | Mean | SD | Range | Mean | SD | Range |
| Systolic pressure (mmHg) | 135.54 | 14.93 | 108-170 | 138.33 | 15.57 | 116-172 |
| diastolic blood pressure (mmHg) | 86.69 | 8.20 | 73-101 | 81.13 | 11.98 | 60-111 |
| mean arterial pressure (mmHg) | 102.97 | 9.21 | 89-124 | 100.20 | 12.10 | 84-131.33 |
| pulse (pulse/min) | 79.15 | 11.65 | 54-106 | 80.27 | 11.93 | 60-102 |

TABLE 7

Blood and pulse rate of all the subjects during weeks 0 to 16 of the test

| | Test group | | Placebo group | |
|---|---|---|---|---|
| | Mean | SD | Mean | SD |
| Systolic pressure | | | | |
| Week 0 | 139.52 | 18.07 | 132.78 | 9.07 |
| Week 12 | 141.13 | 20.51 | 136.24 | 8.89 |
| Week 16 | 136.57 | 19.51 | 136.50 | 12.75 |
| diastolic blood pressure | | | | |
| Week 0 | 85.13 | 11.04 | 84.06 | 8.71 |
| Week 12 | 84.04 | 12.50 | 82.53 | 8.09 |
| Week 16 | 84.43 | 13.35 | 83.63 | 8.62 |
| mean arterial pressure | | | | |
| Week 0 | 103.26 | 12.04 | 100.30 | 7.52 |
| Week 12 | 103.07 | 14.45 | 100.43 | 7.70 |
| Week 16 | 102.36 | 14.07 | 101.25 | 9.41 |
| pulse | | | | |
| Week 0 | 77.52 | 13.09 | 82.17 | 9.10 |
| Week 12 | 75.96 | 14.39 | 82.76 | 7.07* |
| Week 16 | 73.87 | 15.23 | 80.13 | 9.31 |

TABLE 8

Blood and pulse rate of subjects with stages 3 and 4 chronic kidney disease during weeks 0 to 16 of the test

| | stage 3 | | | | stage 4 | | | |
|---|---|---|---|---|---|---|---|---|
| | Test group | | Placebo group | | Test group | | Placebo group | |
| | Mean | SD | Mean | SD | Mean | SD | Mean | SD |
| Systolic pressure | | | | | | | | |
| Week 0 | 139.50 | 19.86 | 132.14 | 8.26 | 139.55 | 16.88 | 135.00 | 12.70 |
| Week 12 | 143.25 | 23.43 | 135.46 | 8.54 | 138.82 | 17.63 | 138.75 | 10.90 |
| Week 16 | 140.58 | 16.38 | 136.62 | 13.59 | 132.18 | 22.40 | 136.00 | 10.58 |
| diastolic blood pressure | | | | | | | | |
| Week 0 | 88.25 | 8.85 | 85.36 | 7.66 | 81.73 | 12.55 | 79.50 | 11.82 |
| Week 12 | 85.92 | 13.42 | 83.54 | 8.04 | 82.00 | 11.70 | 79.25 | 8.46 |
| Week 16 | 87.83 | 10.43 | 85.00 | 8.83 | 80.73 | 15.60 | 77.67 | 4.93 |
| mean arterial pressure | | | | | | | | |
| Week 0 | 105.3 | 11.4 | 101.0 | 6.5 | 101.00 | 12.82 | 98.00 | 11.25 |
| Week 12 | 105.0 | 15.9 | 100.8 | 7.9 | 100.94 | 13.14 | 99.08 | 8.14 |
| Week 16 | 105.4 | 11.3 | 102.2 | 9.9 | 99.03 | 16.51 | 97.11 | 6.81 |
| pulse | | | | | | | | |
| Week 0 | 77.75 | 14.81 | 80.36 | 8.48 | 77.27 | 11.64 | 88.50 | 9.43 |
| Week 12 | 75.67 | 15.52 | 81.92 | 7.61 | 76.27 | 13.79 | 85.50 | 4.65 |
| Week 16 | 75.75 | 16.25 | 79.38 | 9.79 | 71.82 | 14.52 | 83.33 | 7.51 |

TABLE 9

Distribution of the number of persons with improvement among all the subjects prior to and post test

| | Test group (n, %) | Placebo group (n, %) |
|---|---|---|
| Decrease of Systolic pressure more than 2 mmHg | | |
| Week 12 | 9 (39.13) | 5 (29.41) |
| Week 16 | 12 (52.17) | 4 (25.00) |
| Decrease of diastolic blood pressure more than 2 mmHg | | |
| Week 12 | 11 (47.83) | 8 (47.06) |
| Week 16 | 10 (43.38) | 3 (18.75) |
| Decrease of mean arterial pressure more than 2 mmHg | | |
| Week 12 | 10 (43.48) | 7 (41.18) |
| Week 16 | 11 (47.83) | 5 (31.25) |
| Decrease of pulse more than 2 mmHg | | |
| Week 12 | 10 (43.48) | 6 (35.29) |
| Week 16 | 11 (47.83) | 10 (62.50) |

TABLE 10

Distribution of the number of persons with improvement among subjects with stages 3 and 4 chronic kidney disease prior to and post test

| | stage 3 (n, %) | | stage 4 (n, %) | |
|---|---|---|---|---|
| | Test group | Placebo group | Test group | Placebo group |
| Decrease of Systolic pressure more than 2 mmHg | | | | |
| Week 12 | 6 (50.00) | 4 (30.77) | 3 (27.27) | 1 (25.00) |
| Week 16 | 6 (50.00) | 3 (23.08) | 6 (54.55) | 1 (33.33) |
| Decrease of diastolic blood pressure more than 2 mmHg | | | | |
| Week 12 | 7 (58.33) | 7 (53.85) | 4 (36.36) | 1 (25.00) |
| Week 16 | 5 (41.67) | 3 (23.08) | 5 (45.45) | 0 (0.00) |
| Decrease of mean arterial pressure more than 2 mmHg | | | | |
| Week 12 | 7 (58.33) | 6 (46.15) | 3 (27.27) | 1 (25.00) |
| Week 16 | 7 (58.33) | 4 (30.77) | 4 (36.36) | 1 (33.33) |
| Decrease of pulse more than 2 mmHg | | | | |
| Week 12 | 5 (41.67) | 5 (38.46) | 5 (45.45) | 1 (25.00) |
| Week 16 | 5 (41.67) | 7 (53.85) | 6 (54.55) | 3 (100.00) |

Example 6: Hematological Analysis

Tables 11 and 12 compare the difference between the two groups by Wilcoxon rank-sum test, and the values are expressed as mean, standard deviation, and minimum-maximum. In the tables, the symbol "*" indicates that there is significant difference between different groups ($p<0.05$); and the symbol "#" indicates that there is difference between those with different courses of disease in the same group ($p<0.05$). It can be known from Tables 11 and 12 that the mean triglyceride and blood glucose level of the 41 subjects are 179.27±105.33 mg/dL and 141.45±78.80 mg/dL respectively. The subjects with stage 3 chronic kidney disease have a mean triglyceride and blood glucose level of 174.04±106.14 mg/dL and 146.69±81.69 mg/dL, the subjects with stage 4 chronic kidney disease have a mean triglyceride and blood glucose of 188.33±106.96 mg/dL and 131.71±75.09 mg/dL, and thus the mean triglyceride and blood glucose of the subjects with stages 3 and 4 chronic kidney disease are both higher than the standards for metabolic syndrome (triglyceride ≥150 mg/dL, and blood glucose ≥100 mg/dL). Moreover, the mean plasma total cholesterol, low-density lipoprotein cholesterol, high-density lipoprotein cholesterol, and thyroid function of the subject fall within a normal range. The subjects with stage 4 chronic kidney disease have a high-density lipoprotein cholesterol level of 48.07±14.67 μg/dL, which is lower than that (52.19±14.10 μg/dL) of the subjects with stage 3 chronic kidney disease, but have a higher plasma total cholesterol, triglyceride, and low-density lipoprotein cholesterol level compared with the subjects with stage 3 chronic kidney disease.

Further, at week 12 of the test, the average reduction in the blood glucose level of the subjects in the test group is 22.78±74.29 mg/dL, which is approximately 2 times higher than that (−11.24±49.93 mg/dL) of the subjects in the placebo group. The blood glucose level of the subjects with stage 3 chronic kidney disease in the test group is decreased by −54.17±81.83 mg/dL, which is superior to that (3.36±33.89 mg/dL) of the subjects with stage 3 chronic kidney disease in the placebo group. The decrease (11.45±48.00 mg/dL) in the blood glucose level of the subjects with stage 4 chronic kidney disease in the test group is obviously higher than that (−79.33±63.52 mg/dL) of the subjects with stage 4 chronic kidney disease in the placebo group.

At week 12 of the test, the plasma triglyceride level of the subjects in the test group is decreased by −3.86±84.09 mg/dL, and the plasma triglyceride level of the subjects in the placebo group is decreased by −13.56±113.15 mg/dL. The plasma triglyceride level of the subjects with stage 3 chronic kidney disease in the test group is decreased by −28.17±59.59 mg/dL, which is obviously advantageous over that (12.14±73.65 mg/dL) of the subjects with stage 3 chronic kidney disease in the placebo group. At week 16 of the test, the plasma triglyceride level of the subjects in the test group is increased by 8.00 mg/dL, and the plasma triglyceride level of the subjects in the placebo group is increased by 17.11 mg/dL. The plasma triglyceride level of the subjects with stage 4 chronic kidney disease in the placebo group is increased significantly by up to 12±54.31 mg/dL.

At week 0 of the test, the mean plasma cholesterol level of the subjects in the test group and the placebo group is 164.52±35.44 mg/dL and 172.44±39.92 mg/dL respectively, the mean low-density lipoprotein cholesterol (LDL-C) level is 77.22±30.14 mg/dL and 88.72±31.08 mg/dL respectively, and the mean high-density lipoprotein cholesterol (HDL-C) level is 50.61±13.15 mg/dL and 50.78±15.97 mg/dL respectively.

At week 12 of the test, the mean LDL-C level of the subjects in the test group and the placebo group is increased by 8.09±32.67 mg/dL and 9.89±34.65 mg/dL respectively, and still falls within a normal range (plasma cholesterol <200 mg/dL, and LDL-C<100 mg/dL). The increase in the test group is lower than that in the placebo group ($P>0.05$). The mean HDL-C level of the subjects in the test group and the placebo group is decreased by −4.96±9.28 mg/dL and −2.22±8.19 mg/dL respectively, and still falls within a normal range 40 mg/dL).

At week 12 of the test, the thyroxine of the subjects is 8.40±1.56 μg/dL in the test group, and is 7.38±1.33 μg/dL in the placebo group, both of which fall within a normal range (4.5-12 μg/dL).

Tables 13 and 14 compare the difference between the two groups by Fisher's exact test, and the values are expressed as numbers (percentages). At week 12 of the test, improvements are made in 65.22% and 63.00% on average of the subjects in the test group in terms of blood glucose and triglyceride levels, and the improvement rates are still 43.00% and 47.80% after 4-week withdrawal. Up to 83% of the subjects with stage 3 chronic kidney disease have ameliorated blood glucose and triglyceride level, and the improvement effects on the subjects with stage 3 chronic kidney disease are better than those on the subjects with stage 4 chronic kidney disease.

The above results show that the blood glucose and triglyceride levels of the subjects all reach the standards for metabolic syndrome, which can be obviously ameliorated by administering the lactic acid bacteria containing composition disclosed in the present invention, while the LDL-C, HDL-C and T4 levels of the subject are maintained in a normal range. The improvement effect is better with respect to the blood glucose and triglyceride levels of the subjects with stage 3 chronic kidney disease. Therefore, the lactic acid bacteria containing composition disclosed in the present invention can definitely effectively reduce the blood glucose and triglyceride levels in the patients with chronic kidney disease, without affecting the plasma cholesterol, LDL-C, HDL-C, and T4 levels in the patients.

TABLE 11

Hematological analysis of all the subjects during weeks 0 to 16 of the test

| | Test group | | Placebo group | |
|---|---|---|---|---|
| | Mean | SD | Mean | SD |
| blood sugar | | | | |
| Week 0 | 143.74 | 82.83 | 138.35 | 75.38 |
| Week 12 | 120.96 | 31.01 | 124.28 | 59.65 |
| Week 16 | 133.13 | 45.89 | 116.00 | 49.52 |
| triglyceride | | | | |
| Week 0 | 188.50 | 90.19 | 174.06 | 133.06 |
| Week 12 | 183.35 | 80.31 | 160.50 | 80.84 |
| Week 16 | 192.70 | 112.69 | 177.61 | 127.09 |
| cholesterol | | | | |
| Week 0 | 164.52 | 35.44 | 172.44 | 32.92 |
| Week 12 | 171.09 | 30.79 | 178.56 | 37.09 |
| Week 16 | 173.04 | 35.08 | 178.00 | 37.10 |
| LDL-C | | | | |
| Week 0 | 77.22 | 30.14 | 88.72 | 31.08 |
| Week 12 | 85.30 | 24.69 | 98.61 | 38.02 |
| Week 16 | 88.17 | 27.88 | 99.76 | 38.72 |
| HDL-C | | | | |
| Week 0 | 50.61 | 13.15 | 50.78 | 15.97 |
| Week 12 | 45.65 | 13.03 | 48.56 | 16.31 |
| Week 16 | 47.57 | 12.48 | 54.53 | 35.01 |
| T4 | | | | |
| Week 0 | 8.40 | 1.56 | 7.38 | 1.33* |
| Week 12 | 7.78 | 1.63 | 7.43 | 1.50 |
| Week 16 | 7.68 | 1.47 | 7.48 | 1.42 |

TABLE 12

Hematological analysis of subjects with stages 3 and 4 chronic kidney disease during weeks 0 to 16 of the test

| | stage 3 | | | | stage 4 | | | |
|---|---|---|---|---|---|---|---|---|
| | Test group | | Placebo group | | Test group | | Placebo group | |
| | Mean | SD | Mean | SD | Mean | SD | Mean | SD |
| blood sugar | | | | | | | | |
| Week 0 | 177.50 | 101.99 | 120.29 | 49.02 | 106.91 | 28.14 | 222.67 | 129.98* |
| Week 12 | 123.33 | 32.51 | 123.64 | 60.60 | 118.36 | 30.63 | 126.50 | 65.10 |
| Week 16 | 144.75 | 52.61 | 112.79 | 54.20 | 120.46 | 35.34 | 127.25 | 30.80 |
| triglyceride | | | | | | | | |
| Week 0 | 206.33 | 90.99 | 146.36 | 113.46 | 158.27 | 61.29 | 271.00 | 168.64 |
| Week 12 | 178.17 | 87.42 | 158.50 | 89.88 | 200.90 | 96.58 | 267.50 | 44.11 |
| Week 16 | 211.75 | 134.51 | 148.50 | 89.93 | 171.91 | 84.42 | 279.50 | 196.71 |
| cholesterol | | | | | | | | |
| Week 0 | 164.83 | 46.68 | 167.36 | 30.33 | 164.18 | 19.13 | 190.25 | 40.14 |
| Week 12 | 166.00 | 29.88 | 174.07 | 33.72 | 176.64 | 32.23 | 194.25 | 49.47 |
| Week 16 | 173.00 | 36.70 | 173.29 | 31.82 | 173.09 | 35.01 | 194.50 | 54.30 |
| LDL-C | | | | | | | | |
| Week 0 | 74.08 | 39.74 | 83.93 | 31.46 | 80.64 | 15.38 | 105.50 | 26.49 |
| Week 12 | 83.08 | 25.50 | 92.14 | 33.98 | 87.73 | 24.77 | 121.25 | 48.07 |
| Week 16 | 86.58 | 32.51 | 96.79 | 31.36 | 89.91 | 23.25 | 113.67 | 72.45 |

TABLE 12-continued

Hematological analysis of subjects with stages 3 and 4
chronic kidney disease during weeks 0 to 16 of the test

|  | stage 3 | | | | stage 4 | | | |
| --- | --- | --- | --- | --- | --- | --- | --- | --- |
|  | Test group | | Placebo group | | Test group | | Placebo group | |
|  | Mean | SD | Mean | SD | Mean | SD | Mean | SD |
| HDL-C | | | | | | | | |
| Week 0 | 49.50 | 11.37 | 54.50 | 16.13 | 51.82 | 15.34 | 37.75 | 5.12 |
| Week 12 | 46.83 | 14.34 | 51.14 | 17.57 | 44.36 | 11.99 | 39.50 | 5.45 |
| Week 16 | 47.08 | 13.14 | 59.14 | 37.11 | 48.09 | 12.33 | 33.00 | 2.65 |
| T4 | | | | | | | | |
| Week 0 | 8.38 | 1.46 | 7.42 | 1.44* | 8.43 | 1.75 | 7.23 | 0.95 |
| Week 12 | 7.77 | 1.65 | 7.56 | 1.59 | 7.79 | 1.71 | 6.98 | 1.23 |
| Week 16 | 7.17 | 1.15 | 7.65 | 1.53 | 8.23 | 1.65 | 6.83 | 0.75 |

TABLE 13

Distribution of the number of persons with improvement
among all the subjects prior to and post test

|  | Test group (n, %) | Placebo group (n, %) |
| --- | --- | --- |
| blood sugar | | |
| Week 12 | 15 (65.22) | 9 (52.94) |
| Week 16 | 10 (43.48) | 8 (47.06) |
| triglyceride | | |
| Week 12 | 14 (63.64) | 9 (50.00) |
| Week 16 | 11 (47.83) | 10 (55.56) |
| cholesterol | | |
| Week 12 | 9 (39.13) | 6 (33.33) |
| Week 16 | 7 (30.43) | 11 (61.11) |
| LDL-C | | |
| Week 12 | 6 (26.09) | 7 (38.89) |
| Week 16 | 7 (30.43) | 9 (52.94) |
| HDL-C | | |
| Week 12 | 17 (73.91) | 11 (61.11) |
| Week 16 | 16 (69.57) | 11 (64.71 |

TABLE 14

Distribution of the number of persons with improvement
among subjects with stages 3 and 4 chronic kidney disease
prior to and post test

|  | stage 3 (n, %) | | stage 4 (n, %) | |
| --- | --- | --- | --- | --- |
|  | Test group | Placebo group | Test group | Placebo group |
| blood sugar | | | | |
| Week 12 | 10 (83.33) | 6 (42.86) | 5 (45.450 | 3 (100.0) |
| Week 16 | 6 (50.00) | 5 (35.71) | 4 (36.36) | 3 (100.0) |
| triglyceride | | | | |
| Week 12 | 10 (83.33) | 7 (50.00) | 4 (40.00) | 2 (50.00) |
| Week 16 | 6 (50.00) | 8 (57.14) | 5 (45.45) | 2 (50.00) |
| cholesterol | | | | |
| Week 12 | 4 (33.33) | 4 (28.57) | 5 (45.45) | 2 (50.00) |
| Week 16 | 4 (33.33) | 9 (64.29) | 3 (27.27) | 2 (50.00) |
| LDL-C | | | | |
| Week 12 | 3 (25.00) | 6 (42.86) | 3 (27.27) | 1 (25.00) |
| Week 16 | 4 (33.33) | 8 (57.14) | 3 (27.270 | 1 (33.33) |

TABLE 14-continued

Distribution of the number of persons with improvement
among subjects with stages 3 and 4 chronic kidney disease
prior to and post test

|  | stage 3 (n, %) | | stage 4 (n, %) | |
| --- | --- | --- | --- | --- |
|  | Test group | Placebo group | Test group | Placebo group |
| HDL-C | | | | |
| Week 12 | 8 (66.67) | 9 (64.29) | 9 (81.82) | 2 (50.00) |
| Week 16 | 7 (58.33) | 10 (71.43) | 9 (81.82) | 1 (31.33) |

Example 7: Analysis of Renal Function Indices

The analysis results of renal function indices for 41 subjects are shown in Tables 15 and 16, in which the difference between the two groups are compared by Wilcoxon rank-sum test, and the values are expressed as mean, standard deviation, and minimum-maximum. It can be known from Tables 15 and 16 that the chronic kidney disease classification index MDRD-eGFR of the subjects is $36.73 \pm 12.87$ mL/min/1.73 m$^2$, and the CKD-EPI value is $35.55 \pm 12.78$ mL/min/1.73 m$^2$, which are both below the normal value (90-120 mL/min/1.73 m$^2$). The mean MDRD-eGFR value of the subjects with stage 4 chronic kidney disease is $22.85 \pm 3.81$ mL/min/1.73 m$^2$, and the CKD-EPI value is $21.73 \pm 3.65$ mL/min/1.73 m$^2$, which are both greatly lower than the mean MDRD-eGFR value ($44.74 \pm 8.65$ mL/min/1.73 m$^2$) and the CKD-EPI value ($43.53 \pm 8.55$ mL/min/1.73 m$^2$) of the subjects with stage 3 chronic kidney disease. Accordingly, the subjects meet the classification criteria of stages 3 and 4 chronic kidney disease.

The subjects have an average blood urea nitrogen (BUN) level of $30.53 \pm 12.23$ mg/dL, a creatinine level of $2.09 \pm 0.68$ mg/dL, a uric acid (UA) level of $7.34 \pm 2.18$ mg/dL, an indolyl sulfate (IS) level of $1.97 \pm 1.70$ mg/L, and a p-cresol sulfate (PCS) level of $3.45 \pm 2.73$ mg/L, which are all above the normal values (7-25 mg/dL, <0.6-1.3 mg/dL, 1.5-8 mg/dL, $0.6 \pm 0.2$ mg/L, and <0.5 mg/L). Before test, the subjects with stage 4 chronic kidney disease have an average BUN of $41.59 \pm 9.23$ mg/dL, a creatinine level of $2.79 \pm 0.59$ mg/dL, an IS level of $3.05 \pm 2.22$ mg/L, and a PCS level of $4.55 \pm 3.13$ mg/L, which are all higher than the values of the subjects with stage 3 chronic kidney disease ($24.16 \pm 8.72$ mg/dL, $1.68 \pm 0.29$ mg/dL, $1.35 \pm 0.87$ mg/L, and $2.81 \pm 2.30$ mg/L); and there is no obvious difference between the serum UA level of the subjects with stages 3 and 4 chronic kidney disease.

Tables 17 and 18 compare the difference between the two groups by Wilcoxon rank-sum test, and the values are expressed as mean, standard deviation, and minimum-maximum. In the tables, the symbol "*" indicates that there is significant difference between different groups (p<0.05); the symbol "#" indicates that there is difference between those with different courses of disease in the same group (p<0.05); and the symbol "##" indicates that there is significant difference between those with different courses of disease in the same group (p<0.01). At week 12 of the test, the decrease in the MDRD-eGFR and CKD-EPI values of test group is higher than that of the placebo group. After 4-week withdrawal, the increase in the MDRD-eGFR and CKD-EPI values of the placebo group is higher than that of the test group. At week 12 of the test, the subjects with stage 3 chronic kidney disease in the test group have a MDRD-eGFR and CKD-EP value decreased by 2.58±5.57 mL/min/1.73 m$^2$ and 2.63±5.68 mL/min/1.73 m$^2$ respectively, and the decreases are larger than those (−1.61±6.89 mL/min/1.73 m$^2$ and −16.2±6.88 mL/min/1.73 m$^2$) of the placebo group. Although at weeks 12 and 16 of the test, the MDRD-eGFR and CKD-EPI values of the subjects with stage 4 chronic kidney disease in the test group and the placebo group are increased, the increase in the placebo group at week 16 of the test is ten times of that in the test group.

At week 12 of the test, the serum UA levels (7.37±1.93 mg/dL, and 7.31±2.53 mg/dL) in the test group and the placebo group are decreased by 0.51±2.09 mg/dL and 0.73±1.68 mg/dL. At week 16 of the test, the serum UA level is further decreased by 0.18±1.16 mg/dL in the test group, and trends to increase in the placebo group. At week 12 of the test, the serum UA levels of the subjects with stage 3 chronic kidney disease in the test group and the placebo group are both decreased; and at week 16 of the test, the increase in the test group is lower than that in the placebo group.

With respect to serum nephrotoxins, at week 12 of the test, the subjects with stage 4 chronic kidney disease have a BUN level of 31.55±14.12 mg/dL, a creatinine level of 2.19±0.80 mg/dL, an IS level of 2.29±2.06 mg/L, and a PCS level of 4.09±2.90 mg/L, all of which have no significant difference from the values determined at week 0 of the test (P>0.05). For the subjects with stage 3 chronic kidney disease in the test group, except that the PCS level is higher than that in the placebo group, the BUN level (22.10±9.67 mg/dL), the creatinine level (1.57±0.20 mg/dL), and the IS level (1.27±0.66 mg/L) are all increased by a value lower than that of the placebo group (0.02±5.11 mg/dL, 0.13±0.25 mg/dL, 0.13±0.82 mg/dL). Moreover, after 4-week withdrawal, the BUN level, the creatinine level, and the PCS level are decreased by 0.19±5.11 mg/L, 0.07±0.20 mg/L, and 0.25±2.04 mg/L respectively. For the subjects with stage 4 chronic kidney disease in the test group, except for the serum creatinine level (2.86±0.64 mg/dL), the BUN level (41.85±10.58 mg/dL), the IS level (3.40±2.49 mg/L), and the PCS level (5.55±3.05 mg/L) are all slightly increased (by 0.03±11.99 mg/L, 0.69±2.52 mg/L, and 2.69±7.15 mg/L). However, after 4-week withdrawal, the BUN and IS level are persistently decreased. The BUN, creatinine, and UA levels in the test group continuously decrease on a whole after withdrawal.

At week 12 of the test, the percentages of subjects with improvement in the test group and the placebo group are statistically calculated, and the results show that the percentages of subjects with improvements in MDRD-eGFR and CKD-EPI values in the test group are up to 36.84% on average. The improvement rate (45.45%) of the subjects with stage 3 chronic kidney disease is higher than that (25.00%) of the subjects with stage 4 chronic kidney disease. Moreover, the percentages of subjects with stage 3 chronic kidney disease in the test group that are improved in terms of the UA and IS levels are 54.50% and 41.67% on average respectively, which are higher than the placebo group (50.00%, and 35.71%). Furthermore, at week 16 of the test, the number of persons with persistent improvements in the mean BUN and UA levels, the serum UA level of the subjects with stage 3 chronic kidney disease, and the BUN level, the creatinine level, and the UA level of the subjects with stage 4 chronic kidney disease in the test group are all higher than that in the placebo group.

It can be known from the results above that the lactic acid bacteria containing composition disclosed in the present invention has the effect of maintaining renal functions. The improvement effects on the creatinine level of the subjects with stage 4 chronic kidney disease and on the serum IS and UA levels of the subjects with stage 3 chronic kidney disease are all better than those before the lactic acid bacteria containing composition disclosed in the present invention is administered. Moreover, after withdrawal, the increase in the indices with administration of the lactic acid bacteria containing composition disclosed in the present invention is obviously lower than that found without administration. Therefore, it can be known that administration of the lactic acid bacteria containing composition disclosed in the present invention has the effect of maintaining renal functions, efficacy of ameliorating the serum UA level, and thus the capability of preventing hyperuricemia.

TABLE 15

Analysis of renal function indices of all the subjects before test

|  | Mean | SD | Range |
|---|---|---|---|
| MDRD-eGFR (mL/min/1.73 m$^2$) | 36.73 | 12.87 | 17.31-59.85 |
| CKD-EPI (mL/min/1.73 m$^2$) | 35.55 | 12.78 | 16.33-59.31 |
| BUN (mg/dL) | 30.53 | 12.23 | 13.5-60.8 |
| Creatinine (mg/dL) | 2.09 | 0.68 | 1.3-3.8 |
| IS (mg/L) | 1.97 | 1.70 | 0.05-8.9 |
| PCS (mg/L) | 3.45 | 2.73 | 0.28-9.99 |
| UA (mg/L) | 7.34 | 2.18 | 3.3-12.4 |

TABLE 16

Analysis of renal function indices of subjects with stages 3 and 4 chronic kidney disease before test

|  | stage 3 (n = 26) | | | stage 4 (n = 15) | | |
|---|---|---|---|---|---|---|
|  | Mean | SD | Range | Mean | SD | Range |
| MDRD-eGFR (mL/min/1.73 m$^2$) | 44.74 | 8.65 | 30.02-59.85 | 22.85 | 3.81 | 17.31-29.15 |
| CKD-EPI (mL/min/1.73 m$^2$) | 43.53 | 8.55 | 27.73-59.31 | 21.73 | 3.65 | 16.33-27.14 |
| BUN (mg/dL) | 24.16 | 8.72 | 13.5-48.9 | 41.59 | 9.23 | 25.2-60.8 |
| Creatinine (mg/dL) | 1.68 | 0.29 | 1.3-2.4 | 2.79 | 0.59 | 1.8-3.8 |

TABLE 16-continued

Analysis of renal function indices of subjects with
stages 3 and 4 chronic kidney disease before test

|  | stage 3 (n = 26) | | | stage 4 (n = 15) | | |
|---|---|---|---|---|---|---|
|  | Mean | SD | Range | Mean | SD | Range |
| IS (mg/L) | 1.35 | 0.87 | 0.05-4.28 | 3.05 | 2.22 | 0.96-8.90 |
| PCS (mg/L) | 2.81 | 2.30 | 0.28-8.32 | 4.55 | 3.13 | 0.78-9.99 |
| UA (mg/L) | 7.22 | 2.52 | 3.3-12.4 | 7.55 | 1.49 | 4.3-9.9 |

TABLE 17

Analysis of renal function indices of all the subjects during
weeks 0 to 16 of the test

|  | Test group | | Placebo group | |
|---|---|---|---|---|
|  | Mean | SD | Mean | SD |
| MDRD-eGFR | | | | |
| Week 0 | 35.83 | 14.55 | 37.87 | 10.65 |
| Week 12 | 35.85 | 15.55 | 36.75 | 12.75 |
| Week 16 | 35.40 | 15.66 | 39.00 | 12.44 |
| CKD-EPI | | | | |
| Week 0 | 34.72 | 14.50 | 36.63 | 10.50 |
| Week 12 | 34.76 | 15.46 | 35.51 | 12.56 |
| Week 16 | 34.41 | 15.69 | 37.86 | 12.58 |
| BUN | | | | |
| Week 0 | 31.55 | 14.12 | 29.24 | 9.52 |
| Week 12 | 30.62 | 14.97 | 28.87 | 11.77 |
| Week 16 | 31.33 | 11.73 | 27.81 | 9.48 |
| Creatinine | | | | |
| Week 0 | 2.19 | 0.80 | 1.96 | 0.47 |
| Week 12 | 2.17 | 0.77 | 2.13 | 0.85 |
| Week 16 | 2.20 | 0.80 | 1.99 | 0.69 |
| IS | | | | |
| Week 0 | 2.29 | 2.06 | 1.56 | 0.99 |
| Week 12 | 2.60 | 2.20 | 1.77 | 1.19 |
| Week 16 | 2.94 | 2.57 | 1.89 | 1.41 |
| PCS | | | | |
| Week 0 | 4.09 | 2.90 | 2.62 | 2.33 |
| Week 12 | 6.05 | 5.55 | 2.64 | 2.74* |
| Week 16 | 6.22 | 7.01 | 3.01 | 2.66 |
| UA | | | | |
| Week 0 | 7.37 | 1.93 | 7.31 | 2.53 |
| Week 12 | 6.54 | 1.65 | 6.57 | 1.68 |
| Week 16 | 6.67 | 1.59 | 6.88 | 2.20 |

TABLE 18

Analysis of renal function indices of subjects with stages 3
and 4 chronic kidney disease during weeks 0 to 16 of the test

|  | stage 3 | | | | stage 3 | | | |
|---|---|---|---|---|---|---|---|---|
|  | Test group | | Placebo group | | Test group | | Placebo group | |
|  | Mean | SD | Mean | SD | Mean | SD | Mean | SD |
| MDRD-eGFR | | | | | | | | |
| Week 0 | 48.00 | 8.37[##] | 41.94 | 8.14[##] | 22.57 | 4.19 | 23.64 | 2.85 |
| Week 12 | 46.27 | 11.99[##] | 40.33 | 11.70[#] | 21.53 | 3.37 | 24.20 | 7.61 |
| Week 16 | 48.10 | 11.72[##] | 42.84 | 10.73[#] | 22.70 | 4.53 | 25.56 | 8.24 |
| CKD-EPI | | | | | | | | |
| Week 0 | 46.91 | 8.19[##] | 40.64 | 8.01[##] | 21.42 | 3.99 | 22.57 | 2.81 |
| Week 12 | 45.14 | 11.90[##] | 39.02 | 11.49[#] | 20.50 | 3.27 | 23.24 | 7.99 |
| Week 16 | 47.25 | 11.54[##] | 41.65 | 10.95[#] | 21.57 | 4.30 | 24.61 | 8.70 |
| BUN | | | | | | | | |
| Week 0 | 22.10 | 9.67[##] | 25.92 | 7.73[#] | 41.85 | 10.58 | 40.85 | 4.90 |
| Week 12 | 22.84 | 9.75[##] | 26.43 | 11.35[#] | 42.86 | 13.83 | 37.43 | 10.08 |
| Week 16 | 24.29 | 6.87[##] | 24.67 | 7.06[#] | 38.38 | 11.56 | 38.80 | 9.30 |
| Creatinine | | | | | | | | |
| Week 0 | 1.57 | 0.20[##] | 1.79 | 0.32[##] | 2.86 | 0.64 | 2.58 | 0.41 |
| Week 12 | 1.66 | 0.35[##] | 1.97 | 0.81 | 2.97 | 0.52 | 2.68 | 0.86 |
| Week 16 | 1.60 | 0.33[##] | 1.83 | 0.60 | 2.80 | 0.67 | 2.55 | 0.79 |
| IS | | | | | | | | |
| Week 0 | 1.27 | 0.66[##] | 1.42 | 1.03 | 3.40 | 2.49 | 2.06 | 0.69 |
| Week 12 | 1.39 | 1.15[##] | 1.77 | 1.21 | 4.06 | 2.32 | 1.76 | 1.31 |
| Week 16 | 2.00 | 2.28[#] | 1.89 | 1.20 | 4.06 | 2.54 | 1.90 | 2.22 |
| PCS | | | | | | | | |
| Week 0 | 2.76 | 2.06[#] | 2.86 | 2.56 | 5.55 | 3.05 | 1.80 | 1.00* |
| Week 12 | 3.62 | 1.72 | 3.00 | 3.06 | 8.48 | 6.98 | 1.46 | 0.44* |
| Week 16 | 3.13 | 3.11[#] | 3.62 | 2.83 | 9.92 | 8.66 | 1.20 | 0.43* |

TABLE 18-continued

Analysis of renal function indices of subjects with stages 3 and 4 chronic kidney disease during weeks 0 to 16 of the test

|  | stage 3 | | | | stage 3 | | | |
|---|---|---|---|---|---|---|---|---|
|  | Test group | | Placebo group | | Test group | | Placebo group | |
|  | Mean | SD | Mean | SD | Mean | SD | Mean | SD |
| UA |  |  |  |  |  |  |  |  |
| Week 0 | 7.28 | 2.23 | 7.17 | 2.83 | 7.47 | 1.65 | 7.78 | 1.11 |
| Week 12 | 6.45 | 1.86 | 6.44 | 1.80 | 6.69 | 1.36 | 7.03 | 1.23 |
| Week 16 | 6.83 | 1.91 | 6.82 | 2.44 | 6.50 | 1.29 | 7.10 | 1.25 |

Example 8: Analysis of Liver Function Indices

The liver function indices of the 41 subjects are detected before test, and the analysis results are shown in Tables 19 and 20 below. Tables 19 and 20 compare the difference between the two groups by Wilcoxon rank-sum test, and the values are expressed as mean, standard deviation, and minimum-maximum. Tables 19 and 20 shows that the aspartate aminotransferase (AST), alanine aminotransferase (ALT), alkaline phosphatase (ALP), total proteins (TP), albumin (ALB), globulin, A/G (albumin/globulin) ratio, r-GT, total bilirubin (TB), and direct bilirubin (DB) all fall thin normal range. The subjects with stage 4 chronic kidney disease have an obviously lower ALT level, compared with the subjects with stage 3 chronic kidney disease.

Table 21 and 22 compare the difference between the two groups by Wilcoxon rank-sum test, and the values are expressed as mean, standard deviation, and minimum-maximum. In the tables, the symbol "*" indicates that there is significant difference between different groups (p<0.05); the symbol "#" indicates that there is difference between those with different courses of disease in the same group (p<0.05); and the symbol "##" indicates that there is significant difference between those with different courses of disease in the same group (p<0.01). At week 0 of the test, the average serum globulin level in the test group is 3.43±0.35 g/dL, and the average total protein and average globulin levels of the subjects with stage 4 chronic kidney disease in the test group are 7.71±0.46 g/dL, and 3.51±0.38 g/dL respectively. The average serum globulin level in the placebo group is 3.19±0.22 g/dL, and the average total protein and average globulin levels of the subjects with stage 4 chronic kidney disease in the test group are 7.08±0.22 g/dL and 3.03±0.22 g/dL respectively. It can be known from comparison of above data that the average total protein and globulin levels in the test group are higher than those in the placebo group.

The average A/G ratio in the test group is 1.22±0.17. The subjects with stage 3 chronic kidney disease have an albumin level of 4.07±0.24 g/dL, and an A/G ratio of 1.22±0.14; and the subjects with stage 4 chronic kidney disease have an aspartate aminotransferase level of 19.45±5.34 U/dL. In contrast, in the placebo group, the average A/G ratio is 1.33±0.11, the subjects with stage 3 chronic kidney disease have an albumin level of 4.29±0.27 g/dL and an A/G ratio of 1.33±0.09, and the subjects with stage 4 chronic kidney disease has an aspartate aminotransferase level of 28.00±7.62 U/dL, which are all higher than the test group.

At week 12 of the test, the serum aspartate aminotransferase, alanine aminotransferase, alkaline phosphatase and r-GT levels in the test group and the placebo group trend to decrease. The decrease in the alanine aminotransferase, alkaline phosphatase and r-GT levels of the test group is larger than that of the placebo group. The average decrease in the albumin, globulin, and A/G ratio of the test group is greatly lower than that of the placebo group (P<0.05). The increase in the serum A/G ratio of the subjects with stage 3 chronic kidney disease in the test group is larger than that of the placebo group, and the increase in the serum alanine aminotransferase level of the subjects with stage 4 chronic kidney disease is obviously lower than that of the placebo group. Moreover, the serum DB and r-GT levels in the subjects with stage 3 chronic kidney disease in the test group are higher than those of the subjects with stage 4 chronic kidney disease in the test group. At week 16 of the test, the A/G ratio and DB level of the test group are further decreased.

It can be known from above data that administration of the lactic acid bacteria containing composition disclosed in the present invention is effective in reducing the values of liver function indices, and the effect in patients with stage 3 chronic kidney disease is better.

TABLE 19

Blood biochemistry of all the subjects before test

|  | Mean | SD | Range |
|---|---|---|---|
| AST (U/dL) | 24.27 | 11.32 | 11-62 |
| ALT (U/dL) | 22.59 | 15.82 | 7-81 |
| ALP(U/dL) | 63.29 | 16.49 | 37-101 |
| TP (g/dL) | 7.50 | 0.42 | 6.8-8.6 |
| ALB (g/dL) | 4.19 | 0.30 | 3.6-5.1 |
| Globulin (g/dL) | 3.32 | 0.32 | 2.8-4.2 |
| A/G ratio | 1.27 | 0.16 | 0.95-1.70 |
| r-GT (g/dL) | 34.41 | 36.71 | 12-222 |
| TB (mg/dL) | 0.51 | 0.23 | 0.2-1.4 |
| DB (mg/dL) | 0.17 | 0.09 | 0.1-0.5 |

TABLE 20

Blood biochemistry of subjects with stages 3 and 4 chronic kidney disease before test

|  | stage 3 (n = 26) | | | stage 4 (n = 15) | | |
|---|---|---|---|---|---|---|
|  | Mean | SD | Range | Mean | SD | Range |
| AST (U/dL) | 25.73 | 13.12 | 11-62 | 21.73 | 6.93 | 12-39 |
| ALT (U/dL) | 26.31 | 18.30 | 9-81 | 16.13 | 6.85 | 7-34 |
| ALP(U/dL) | 61.65 | 15.67 | 37-97 | 66.13 | 18.03 | 44-101 |
| TP (g/dL) | 7.48 | 0.37 | 6.9-8.4 | 7.54 | 0.49 | 6.8-8.6 |
| ALB (g/dL) | 4.18 | 0.27 | 3.6-4.7 | 4.19 | 0.34 | 3.7-5.1 |
| Globulin (g/dL) | 3.29 | 0.26 | 2.8-3.8 | 3.38 | 0.40 | 2.8-4.2 |

TABLE 20-continued

Blood biochemistry of subjects with stages 3 and 4 chronic kidney disease before test

|  | stage 3 (n = 26) | | | stage 4 (n = 15) | | |
| --- | --- | --- | --- | --- | --- | --- |
|  | Mean | SD | Range | Mean | SD | Range |
| A/G ratio | 1.28 | 0.13 | 0.95-1.46 | 1.26 | 0.20 | 0.95-1.70 |
| r-GT (g/dL) | 38.19 | 42.41 | 14-222 | 27.87 | 23.78 | 12-104 |
| TB (mg/dL) | 0.56 | 0.25 | 0.2-1.4 | 0.43 | 0.16 | 0.3-0.7 |
| DB (mg/dL) | 0.19 | 0.10 | 0.1-0.5 | 0.14 | 0.06 | 0.1-0.3 |

TABLE 21

Blood biochemistry of all the subjects during weeks 0 to 16 of the test

|  | Test group | | Placebo group | |
| --- | --- | --- | --- | --- |
|  | Mean | SD | Mean | SD |
| TP |  |  |  |  |
| Week 0 | 7.56 | 0.43 | 7.42 | 0.40 |
| Week 12 | 7.54 | 0.36 | 7.51 | 0.49 |
| Week 16 | 7.64 | 0.42 | 7.50 | 0.48 |
| ALB |  |  |  |  |
| Week 0 | 4.15 | 0.31 | 4.23 | 0.28 |
| Week 12 | 4.30 | 0.30 | 4.21 | 0.36 |
| Week 16 | 4.25 | 0.25 | 4.28 | 0.28 |
| Globulin |  |  |  |  |
| Week 0 | 3.43 | 0.35 | 3.19 | 0.22* |
| Week 12 | 3.28 | 0.35 | 3.30 | 0.36 |
| Week 16 | 3.37 | 0.34 | 3.27 | 0.30 |
| A/G ratio |  |  |  |  |
| Week 0 | 1.22 | 0.17 | 1.33 | 0.11* |
| Week 12 | 1.31 | 0.17 | 1.29 | 0.19 |
| Week 16 | 1.28 | 0.15 | 1.32 | 0.15 |
| AST |  |  |  |  |
| Week 0 | 23.78 | 11.37 | 24.89 | 11.55 |
| Week 12 | 23.32 | 8.48 | 23.61 | 9.19 |
| Week 16 | 20.73 | 6.15 | 25.19 | 8.84 |
| ALT |  |  |  |  |
| Week 0 | 23.35 | 18.83 | 21.61 | 11.34 |
| Week 12 | 18.59 | 7.93 | 20.11 | 8.41 |
| Week 16 | 18.41 | 8.03 | 21.56 | 10.56 |
| ALP |  |  |  |  |
| Week 0 | 63.87 | 16.33 | 62.56 | 17.14 |
| Week 12 | 59.73 | 14.28 | 60.17 | 16.71 |
| Week 16 | 59.91 | 15.50 | 60.56 | 16.52 |
| r-GT |  |  |  |  |
| Week 0 | 36.87 | 44.90 | 31.28 | 23.29 |
| Week 12 | 27.82 | 14.93 | 28.94 | 14.33 |
| Week 16 | 28.64 | 16.32 | 29.19 | 15.63 |
| TB |  |  |  |  |
| Week 0 | 0.49 | 0.24 | 0.54 | 0.21 |
| Week 12 | 0.50 | 0.27 | 0.54 | 0.26 |
| Week 16 | 0.52 | 0.24 | 0.51 | 0.22 |
| DB |  |  |  |  |
| Week 0 | 0.17 | 0.09 | 0.18 | 0.09 |
| Week 12 | 0.18 | 0.09 | 0.16 | 0.08 |
| Week 16 | 0.15 | 0.08 | 0.17 | 0.08 |

TABLE 22

Blood biochemistry of subjects with stages 3 and 4 chronic kidney disease during weeks 0 to 16 of the test

|  | stage 3 | | | | stage 4 | | | |
| --- | --- | --- | --- | --- | --- | --- | --- | --- |
|  | Test group | | Placebo group | | Test group | | Placebo group | |
|  | Mean | SD | Mean | SD | Mean | SD | Mean | SD |
| TP |  |  |  |  |  |  |  |  |
| Week 0 | 7.43 | 0.36 | 7.52 | 0.39# | 7.71 | 0.46 | 7.08 | 0.22* |
| Week 12 | 7.50 | 0.43 | 7.56 | 0.52 | 7.59 | 0.28 | 7.33 | 0.34 |
| Week 16 | 7.59 | 0.45 | 7.45 | 0.53 | 7.69 | 0.40 | 7.70 | 0.17 |
| ALB |  |  |  |  |  |  |  |  |
| Week 0 | 4.07 | 0.24 | 4.29 | 0.27* | 4.24 | 0.36 | 4.05 | 0.29 |
| Week 12 | 4.28 | 0.24 | 4.26 | 0.38 | 4.33 | 0.36 | 4.03 | 0.21 |
| Week 16 | 4.28 | 0.25 | 4.28 | 0.32 | 4.22 | 0.25 | 4.28 | 0.05 |
| Globulin |  |  |  |  |  |  |  |  |
| Week 0 | 3.36 | 0.31 | 3.24 | 0.20 | 3.51 | 0.38 | 3.03 | 0.22* |
| Week 12 | 3.22 | 0.36 | 3.30 | 0.38 | 3.36 | 0.33 | 3.30 | 0.37 |
| Week 16 | 3.31 | 0.33 | 3.23 | 0.32 | 3.45 | 0.35 | 3.43 | 0.15 |
| A/G ratio |  |  |  |  |  |  |  |  |
| Week 0 | 1.22 | 0.14 | 1.33 | 0.09* | 1.23 | 0.21 | 1.35 | 0.17 |
| Week 12 | 1.35 | 0.18 | 1.31 | 0.19 | 1.27 | 0.16 | 1.23 | 0.18 |
| Week 16 | 1.31 | 0.14 | 1.34 | 0.16 | 1.24 | 0.16 | 1.24 | 0.05 |
| AST |  |  |  |  |  |  |  |  |
| Week 0 | 27.75 | 14.03 | 24.00 | 12.54 | 19.45 | 5.34 | 28.00 | 7.62* |
| Week 12 | 24.67 | 9.80 | 23.36 | 9.77 | 21.70 | 6.72 | 24.50 | 7.94 |
| Week 16 | 21.33 | 6.75 | 24.62 | 9.73 | 20.00 | 5.62 | 27.67 | 2.52 |
| ALT |  |  |  |  |  |  |  |  |
| Week 0 | 31.83 | 22.79# | 21.57 | 12.33 | 14.09 | 5.26 | 21.75 | 8.34 |
| Week 12 | 22.67 | 8.25## | 20.14 | 8.91 | 13.70 | 3.86 | 20.00 | 7.53 |
| Week 16 | 22.58 | 8.40## | 21.15 | 11.36 | 13.40 | 3.60 | 23.33 | 7.51* |
| ALP |  |  |  |  |  |  |  |  |
| Week 0 | 60.42 | 14.50 | 62.71 | 17.08 | 67.64 | 18.04 | 62.00 | 20.02 |
| Week 12 | 54.42 | 12.44 | 61.71 | 15.94 | 66.10 | 14.28 | 54.75 | 20.77 |
| Week 16 | 56.67 | 16.72 | 61.00 | 15.32 | 63.80 | 13.73 | 58.67 | 25.17 |
| r-GT |  |  |  |  |  |  |  |  |
| Week 0 | 52.17 | 58.90 | 26.21 | 13.73 | 20.18 | 5.67 | 49.00 | 41.46 |
| Week 12 | 33.42 | 17.95 | 26.50 | 10.70 | 21.10 | 5.88 | 37.50 | 23.27 |
| Week 16 | 35.50 | 19.28# | 24.85 | 7.81 | 20.40 | 5.38 | 48.00 | 28.51 |
| TB |  |  |  |  |  |  |  |  |
| Week 0 | 0.55 | 0.30 | 0.57 | 0.21 | 0.43 | 0.16 | 0.43 | 0.19 |
| Week 12 | 0.62 | 0.30 | 0.59 | 0.28 | 0.35 | 0.11 | 0.40 | 0.08 |
| Week 16 | 0.63 | 0.27 | 0.55 | 0.23 | 0.39 | 0.11 | 0.33 | 0.06 |
| DB |  |  |  |  |  |  |  |  |
| Week 0 | 0.20 | 0.11 | 0.19 | 0.09 | 0.14 | 0.05 | 0.15 | 0.10 |
| Week 12 | 0.22 | 0.09# | 0.17 | 0.08 | 0.13 | 0.05 | 0.13 | 0.05 |
| Week 16 | 0.18 | 0.09 | 0.18 | 0.08 | 0.12 | 0.04 | 0.10 | 0.00 |

Example 9: Analysis of Serum Minerals

Tables 24 to 26 compare the difference between the two groups by Wilcoxon rank-sum test, and the values are expressed as mean, standard deviation, and minimum-maximum. In Table 26, the symbol "*" indicates that there is significant difference between those having the same course of disease in different groups ($p<0.05$); and the symbol "#" indicates that there is difference between those with different courses of disease in the same group ($p<0.05$). It can be known from comparison of the data before and after test that all the values fall within normal ranges. There is no significant difference between the serum potassium, chloride, calcium, phosphorus, and magnesium levels of the subjects with stages 3 and 4 chronic kidney disease; however, the serum magnesium level in subjects with stage 3 chronic kidney disease in the test group is higher than that in the placebo group. The serum potassium level in subjects with stage 3 chronic kidney disease in the placebo group is significantly higher than that in the subjects with stage 4 chronic kidney disease. The serum chloride, phosphorus, and magnesium levels in subjects with stage 3 chronic kidney disease in the test group are obviously lower than those in subjects with stage 4 chronic kidney disease.

At week 12 of the test, the serum sodium, chloride, calcium, and phosphorus levels in the test group tend to decrease. Only the serum chloride level in the patients with stage 3 chronic kidney disease in the test group tends to decrease, and other minerals trend to increase. The serum potassium, chloride, and calcium levels in the placebo group all tend to decrease.

At week 16 of the test, serum sodium, calcium, phosphorus, and magnesium levels tend to persistent decrease. The serum sodium, potassium, chloride, calcium, phosphorus, and magnesium levels in subjects with stage 4 chronic kidney disease in the test group and the potassium and calcium levels in the placebo group all tend to decrease. Compared with the subjects with stage 4 chronic kidney disease in the test group, the serum calcium and magnesium levels of the subjects with stage 3 chronic kidney disease in the test group are increased considerably, and the case in the placebo group is on the contrary.

It can be known from above that the serum sodium, potassium, and chloride levels in the test group tend to decrease, and the chloride and calcium levels in the placebo group also tend to decrease. The results suggest that administration of the lactic acid bacteria containing composition disclosed in the present invention is effective in improving the serum sodium, potassium, calcium, phosphorus, and magnesium levels in the patients with stage 3 chronic kidney disease. In other words, the lactic acid bacteria containing composition disclosed in the present invention can maintain blood calcium level, and thus be useful as a composition for preventing hypocalcemia.

TABLE 23

Analysis of serum minerals in all the subjects before test

|  | Mean | SD | Range |
|---|---|---|---|
| sodium (meq/L) | 140.15 | 2.98 | 134-149 |
| potassium (meq/L) | 4.34 | 0.76 | 3.4-7.5 |
| chloride (meq/L) | 105.05 | 2.74 | 98.3-109.5 |
| calcium (mg/L) | 9.52 | 0.56 | 8.8-12.1 |
| phosphorus (mg/L) | 3.36 | 1.18 | 1.6-9.3 |
| magnesium (mg/L) | 2.19 | 0.31 | 1.4-2.8 |

TABLE 24

Analysis of serum minerals in subjects with stages 3 and 4 chronic kidney disease before test

|  | Stage 3 (n = 26) | | | Stage 4 (n = 15) | | |
|---|---|---|---|---|---|---|
|  | Mean | SD | Range | Mean | SD | Range |
| sodium (meq/L) | 140.31 | 2.92 | 134-149 | 139.87 | 3.16 | 134-146 |
| potassium (meq/L) | 4.21 | 0.78 | 3.4-7.5 | 4.57 | 0.69 | 3.7-5.7 |
| chloride (meq/L) | 104.59 | 2.49 | 98.3-108.7 | 105.84 | 3.05 | 98.3-109.5 |
| calcium (mg/L) | 9.42 | 0.40 | 8.8-10.5 | 9.69 | 0.75 | 8.9-12.1 |
| phosphorus (mg/L) | 3.03 | 0.50 | 1.6-3.9 | 3.93 | 1.72 | 2.3-9.3 |
| magnesium (mg/L) | 2.17 | 0.27 | 1.7-2.8 | 2.22 | 0.37 | 1.4-2.7 |

TABLE 25

Analysis of serum minerals in all the subjects during weeks 0 to 16 of the test

|  | Test group | | Placebo group | |
|---|---|---|---|---|
|  | Mean | SD | Mean | SD |
| sodium | | | | |
| Week 0 | 140.00 | 2.61 | 140.33 | 3.46 |
| Week 12 | 139.77 | 2.64 | 141.06 | 3.06 |
| Week 16 | 140.13 | 2.60 | 140.31 | 3.24 |
| potassium | | | | |
| Week 0 | 4.19 | 0.54 | 4.54 | 0.96 |
| Week 12 | 4.39 | 0.57 | 4.26 | 0.54 |
| Week 16 | 4.52 | 0.80 | 4.25 | 0.46 |
| chloride | | | | |
| Week 0 | 104.94 | 2.82 | 105.18 | 2.71 |
| Week 12 | 104.07 | 2.31 | 104.67 | 2.85 |
| Week 16 | 105.10 | 2.42 | 106.16 | 1.91 |
| calcium | | | | |
| Week 0 | 9.48 | 0.36 | 9.57 | 0.75 |
| Week 12 | 9.40 | 0.45 | 9.38 | 0.76 |
| Week 16 | 9.33 | 0.52 | 9.53 | 0.84 |
| phosphorus | | | | |
| Week 0 | 3.57 | 1.38 | 3.09 | 0.82 |
| Week 12 | 3.27 | 0.65 | 3.14 | 0.62 |
| Week 16 | 3.18 | 0.48 | 3.01 | 0.54 |
| magnesium | | | | |
| Week 0 | 2.20 | 0.31 | 2.18 | 0.31 |
| Week 12 | 2.26 | 0.30 | 2.28 | 0.33 |
| Week 16 | 2.19 | 0.46 | 2.09 | 0.26 |

TABLE 26

Analysis of serum minerals in subjects with stages 3 and 4
chronic kidney disease during weeks 0 to 16 of the test

| | stage 3 | | | | stage 4 | | | |
| --- | --- | --- | --- | --- | --- | --- | --- | --- |
| | Test group | | Placebo group | | Test group | | Placebo group | |
| | Mean | SD | Mean | SD | Mean | SD | Mean | SD |
| sodium | | | | | | | | |
| Week 0 | 139.58 | 2.50 | 140.93 | 3.20 | 140.46 | 2.77 | 138.25 | 4.03 |
| Week 12 | 140.00 | 2.86 | 141.00 | 2.96 | 139.50 | 2.46 | 141.25 | 3.86 |
| Week 16 | 139.42 | 2.23 | 140.15 | 3.39 | 140.91 | 2.84 | 141.00 | 3.00 |
| potassium | | | | | | | | |
| Week 0 | 4.04 | 0.45 | 4.36 | 0.98# | 4.35 | 0.59 | 5.18 | 0.62 |
| Week 12 | 4.22 | 0.44 | 4.11 | 0.37 | 4.60 | 0.65 | 4.75 | 0.79 |
| Week 16 | 4.51 | 0.93 | 4.18 | 0.47 | 4.53 | 0.67 | 4.53 | 0.42 |
| chloride | | | | | | | | |
| Week 0 | 103.76 | 2.73# | 105.30 | 2.10 | 106.23 | 2.41 | 104.78 | 4.70 |
| Week 12 | 103.35 | 2.08 | 104.15 | 2.43 | 104.93 | 2.37 | 106.48 | 3.87 |
| Week 16 | 104.87 | 2.33 | 105.88 | 1.96 | 105.36 | 2.59 | 107.30 | 1.40 |
| calcium | | | | | | | | |
| Week 0 | 9.38 | 0.37 | 9.46 | 0.44 | 9.59 | 0.34 | 9.95 | 1.46 |
| Week 12 | 9.52 | 0.51 | 9.29 | 0.46 | 9.25 | 0.33 | 9.68 | 1.49 |
| Week 16 | 9.40 | 0.65 | 9.31 | 0.43 | 9.26 | 0.35 | 10.50 | 1.56 |
| phosphorus | | | | | | | | |
| Week 0 | 3.05 | 0.44# | 3.02 | 0.57 | 4.15 | 1.81 | 3.33 | 1.53 |
| Week 12 | 3.10 | 0.48 | 3.07 | 0.42 | 3.47 | 0.79 | 3.38 | 1.14 |
| Week 16 | 3.03 | 0.37 | 2.98 | 0.43 | 3.35 | 0.56 | 3.17 | 1.03 |
| magnesium | | | | | | | | |
| Week 0 | 2.07 | 0.28# | 2.26 | 0.23* | 2.35 | 0.27 | 1.88 | 0.41* |
| Week 12 | 2.23 | 0.32 | 2.32 | 0.32 | 2.31 | 0.28 | 2.13 | 0.38 |
| Week 16 | 2.12 | 0.33 | 2.16 | 0.19 | 2.27 | 0.59 | 1.77 | 0.32 |

Example 10: Analysis of Blood Cell Characteristics

The analysis results of blood cell characteristics of the subjects before test are shown in Tables 27 and 28, in which the difference between the two groups are compared by Wilcoxon rank-sum test, and the values are expressed as mean, standard deviation, and minimum-maximum. In the tables, the symbol "*" indicates that there is significant difference between different groups ($p<0.05$); and the symbol "#" indicates that there is difference between those with different courses of disease in the same group ($p<0.05$). Tables 27 and 28 show that except for subjects with stage 4 chronic kidney disease, the average hematocrit in other subjects is lower than the lowest standard, and other average values fall within normal ranges. Moreover, the leukocyte and erythrocyte counts, hematocrit, hematochrome level, mean hemoglobin concentration, platelet and lymphocyte counts in subjects with stage 4 chronic kidney disease are all lower than those in subjects with stage 3 chronic kidney disease, and there is difference between the erythrocyte counts, hematochrome and hematocrit, and lymphocyte counts.

Table 29 and 30 compare the difference between the two groups by Wilcoxon rank-sum test, and the values are expressed as mean, standard deviation, and minimum-maximum. In the tables, the symbol "*" indicates that there is significant difference between those with the same courses of disease in different groups ($p<0.05$); and the symbol "#" indicates that there is difference between those with different courses of disease in the same group ($p<0.05$). At week 12 of the test, the decrease in leukocyte and lobulated leukocyte counts of the subjects with stage 3 chronic kidney disease in the test group is significantly larger than that in the placebo group, and the increase in the lymphocyte counts is obviously higher than that in the placebo group.

At week 0 of the test, the lobulated leukocyte counts in the subjects with stage 4 chronic kidney disease in the test group are considerably lower than those in the placebo group; however, at week 16 of the test, there is no obvious difference from the placebo group. Furthermore, at week 16 of the test, the mean corpuscular volume in the test group is significantly higher than that in the placebo group, and the case is on the contrary for platelets.

Before test, the hematocrit in the subjects with stage 3 chronic kidney disease in the test group is higher than that in the subjects with stage 4 chronic kidney disease; and at weeks 12 and 16 of the test, the erythrocyte counts, hemoglobin concentration, hematocrit, and lymphocyte counts are higher than those in subjects with stage 4 chronic kidney disease. At week 0 of the test, the erythrocyte counts, hemoglobin concentration, hematocrit, lymphocyte and lobulated leukocyte counts in the subjects with stage 3 chronic kidney disease in the placebo group are significantly higher than those in subjects with stage 4 chronic kidney disease in the placebo group. At week 16 of the test, the erythrocyte counts, hematocrit and monocyte counts in the subjects with stage 3 chronic kidney disease in the placebo group are also significantly higher than those in subjects with stage 4 chronic kidney disease in the placebo group. However, at weeks 12 and 16 of the test, the variation in platelets of the subjects with stage 3 chronic kidney disease in the placebo group is obviously lower than that of the subjects with stage 4 chronic kidney disease in the placebo group.

The above results show that in a severe course of chronic kidney disease, nutrient-related average erythrocyte counts, hematochrome concentration, hematocrit, and lymphocyte counts are reduced, while inflammation-related mean corpuscular volume, and eosinophil, lymphocyte, monocyte and basophil counts are increased. By administering the lactic acid bacteria containing composition disclosed in the present invention, the symptoms can be improved.

TABLE 27

Analysis of blood cell characteristics in all the subject before test

|  | Mean | SD | Range |
|---|---|---|---|
| leukocyte (×10³/uL) | 6.89 | 2.03 | 3.1-14.6 |
| erythrocyte (×10⁶/dL) | 4.38 | 0.62 | 3.26-5.81 |
| hematochrome (g/dL) | 13.14 | 1.81 | 9.6-17.4 |
| hematocrit (%) | 38.89 | 4.86 | 28.5-48.7 |
| mean corpuscular volume (fL) | 89.10 | 4.45 | 73.46-96.11 |
| mean corpuscular hemoglobin (pg) | 30.07 | 1.65 | 23.55-32.67 |
| mean hemoglobin concentration (%) | 33.72 | 1.20 | 31.50-36.10 |
| platelet (×10³/uL) | 215.20 | 68.30 | 111-502 |
| eosinophil (%) | 2.94 | 1.92 | 0.12-8.31 |
| lymphocyte (K/uL) | 26.37 | 8.02 | 7.52-40.90 |
| monocyte (K/uL) | 6.04 | 1.94 | 1.12-9.80 |
| lobulated leukocyte (K/uL) | 64.18 | 9.73 | 50.2-91.21 |
| basophil (K/uL) | 0.47 | 0.26 | 0.1-1.3 |

TABLE 28

Analysis of blood cell characteristics in subjects with stages 3 and 4 chronic kidney disease before test

|  | Stage 3 (n = 26) | | | Stage 4 (n = 15) | | |
|---|---|---|---|---|---|---|
|  | Mean | SD | Range | Mean | SD | Range |
| leukocyte (×10³/uL) | 7.01 | 2.18 | 3.8-14.6 | 6.69 | 1.81 | 3.1-10.5 |
| erythrocyte (×10⁶/dL) | 4.61 | 0.58 | 3.46-5.81 | 3.98 | 0.47 | 3.26-4.99 |
| hematochrome (g/dL) | 13.78 | 1.73 | 9.9-17.4 | 12.01 | 1.36 | 9.6-15.0 |
| hematocrit (%) | 40.67 | 4.39 | 31.3-48.7 | 35.81 | 4.12 | 28.5-44.1 |
| mean corpuscular volume (fL) | 88.55 | 5.01 | 73.46-95.59 | 90.04 | 3.18 | 85.49-96.11 |
| mean corpuscular hemoglobin (pg) | 29.97 | 1.93 | 23.55-32.67 | 30.25 | 1.01 | 28.35-32.13 |
| mean hemoglobin concentration (%) | 33.78 | 1.24 | 31.57-36.10 | 33.61 | 1.16 | 31.50-35.52 |
| platelet (×10³/uL) | 219.35 | 79.20 | 111-502 | 208.00 | 45.16 | 140-279 |
| eosinophil (%) | 2.72 | 1.65 | 0.2-5.5 | 3.34 | 2.32 | 0.12-8.31 |
| lymphocyte (K/uL) | 28.23 | 7.52 | 12.02-40.9 | 23.14 | 8.08 | 7.52-35.0 |
| monocyte (K/uL) | 5.97 | 1.81 | 2.9-9.4 | 6.17 | 2.22 | 1.12-9.8 |
| lobulated leukocyte (K/uL) | 62.62 | 9.30 | 50.2-82.91 | 66.87 | 10.19 | 50.2-91.21 |
| basophil (K/uL) | 0.46 | 0.22 | 0.1-1.0 | 0.48 | 0.32 | 0.1-1.3 |

TABLE 29

Analysis of blood cell characteristics in all the subject during weeks 0 to 16 of the test

|  | Test group | | Placebo group | |
|---|---|---|---|---|
|  | Mean | SD | Mean | SD |
| leukocyte | | | | |
| Week 0 | 6.73 | 1.47 | 7.10 | 2.61 |
| Week 12 | 6.27 | 1.58 | 7.44 | 2.64 |
| Week 16 | 6.24 | 1.78 | 6.84 | 2.28 |
| erythrocyte | | | | |
| Week 0 | 4.32 | 0.62 | 4.45 | 0.63 |
| Week 12 | 4.28 | 0.63 | 4.49 | 0.58 |
| Week 16 | 4.27 | 0.64 | 4.55 | 0.59 |
| hematochrome | | | | |
| Week 0 | 13.06 | 2.00 | 13.23 | 1.59 |
| Week 12 | 12.98 | 2.03 | 13.26 | 1.67 |
| Week 16 | 13.04 | 2.07 | 13.32 | 1.56 |
| hematocrit | | | | |
| Week 0 | 38.74 | 5.04 | 39.08 | 4.75 |
| Week 12 | 38.40 | 5.26 | 39.26 | 4.78 |
| Week 16 | 38.76 | 5.21 | 39.47 | 4.84 |
| mean corpuscular volume | | | | |
| Week 0 | 89.85 | 3.50 | 88.14 | 5.38 |
| Week 12 | 89.92 | 3.00 | 87.67 | 5.83 |
| Week 16 | 90.97 | 2.95 | 87.48 | 5.39* |
| mean corpuscular hemoglobin | | | | |
| Week 0 | 30.22 | 1.05 | 29.88 | 2.21 |
| Week 12 | 30.33 | 1.30 | 29.62 | 2.44 |
| Week 16 | 30.53 | 1.27 | 29.40 | 2.46 |
| mean hemoglobin concentration | | | | |
| Week 0 | 33.58 | 1.19 | 33.89 | 1.21 |
| Week 12 | 33.73 | 1.15 | 33.77 | 1.21 |
| Week 16 | 33.58 | 1.29 | 33.58 | 1.42 |

TABLE 29-continued

Analysis of blood cell characteristics in all the subject during weeks 0 to 16 of the test

| | Test group | | Placebo group | |
|---|---|---|---|---|
| | Mean | SD | Mean | SD |
| platelet | | | | |
| Week 0 | 209.26 | 74.88 | 222.78 | 60.10 |
| Week 12 | 206.48 | 71.33 | 218.78 | 63.47 |
| Week 16 | 211.04 | 73.10 | 221.33 | 69.11 |
| eosinophil | | | | |
| Week 0 | 3.13 | 2.08 | 2.70 | 1.73 |
| Week 12 | 3.83 | 2.48 | 3.09 | 1.87 |
| Week 16 | 3.17 | 2.16 | 7.59 | 15.41 |
| lymphocyte | | | | |
| Week 0 | 26.17 | 4.71 | 26.63 | 11.07 |
| Week 12 | 29.29 | 6.79 | 26.90 | 7.98 |
| Week 16 | 28.12 | 5.83 | 29.72 | 8.38 |
| monocyte | | | | |
| Week 0 | 5.59 | 1.61 | 6.63 | 2.21 |
| Week 12 | 6.49 | 1.85 | 6.74 | 1.39 |
| Week 16 | 5.97 | 2.13 | 6.39 | 1.51 |
| lobulated leukocyte | | | | |
| Week 0 | 64.62 | 6.50 | 63.62 | 12.95 |
| Week 12 | 59.87 | 6.32 | 62.85 | 8.99 |
| Week 16 | 56.96 | 17.97 | 51.59 | 20.86 |
| basophil | | | | |
| Week 0 | 0.50 | 0.26 | 0.42 | 0.26 |
| Week 12 | 0.52 | 0.24 | 0.44 | 0.21 |
| Week 16 | 0.44 | 0.20 | 0.52 | 0.28 |

TABLE 30

Analysis of blood cell characteristics in subjects with stages 3 and 4 chronic kidney disease during weeks 0 to 16 of the test

| | Stage 3 | | | | Stage 4 | | | |
|---|---|---|---|---|---|---|---|---|
| | Test group | | Placebo group | | Test group | | Placebo group | |
| | Mean | SD | Mean | SD | Mean | SD | Mean | SD |
| leukocyte | | | | | | | | |
| Week 0 | 7.10 | 1.16 | 6.94 | 2.82 | 6.33 | 1.72 | 7.68 | 1.91 |
| Week 12 | 6.14 | 1.14 | 7.04 | 2.66 | 6.40 | 2.01 | 8.83 | 2.33 |
| Week 16 | 6.58 | 1.26 | 6.59 | 2.14 | 5.88 | 2.22 | 7.73 | 2.85 |
| erythrocyte | | | | | | | | |
| Week 0 | 4.58 | 0.65 | 4.64 | 0.55[#] | 4.04 | 0.48 | 3.80 | 0.46 |
| Week 12 | 4.61 | 0.60[#] | 4.64 | 0.53 | 3.92 | 0.44 | 3.98 | 0.46 |
| Week 16 | 4.61 | 0.63[#] | 4.72 | 0.55[#] | 3.90 | 0.43 | 3.97 | 0.34 |
| hematochrome | | | | | | | | |
| Week 0 | 13.90 | 2.18 | 13.69 | 1.32[#] | 12.14 | 1.33 | 11.65 | 1.59 |
| Week 12 | 14.01 | 2.03[#] | 13.59 | 1.53 | 11.85 | 1.35 | 12.10 | 1.81 |
| Week 16 | 14.13 | 2.09[#] | 13.69 | 1.40 | 11.86 | 1.29 | 12.05 | 1.61 |
| hematocrit | | | | | | | | |
| Week 0 | 40.91 | 5.12[#] | 40.46 | 3.84[#] | 36.37 | 3.91 | 34.25 | 4.89 |
| Week 12 | 41.33 | 4.79[#] | 40.27 | 4.36 | 35.19 | 3.72 | 35.73 | 5.08 |
| Week 16 | 41.59 | 4.77[#] | 40.89 | 4.09[#] | 35.66 | 3.82 | 34.53 | 4.29 |
| mean corpuscular volume | | | | | | | | |
| Week 0 | 89.62 | 3.56 | 87.63 | 5.97 | 90.09 | 3.59 | 89.90 | 2.07 |
| Week 12 | 89.86 | 3.17 | 87.10 | 6.41 | 89.98 | 2.96 | 89.65 | 2.79 |
| Week 16 | 90.57 | 3.33 | 86.93 | 5.94 | 91.40 | 2.57 | 89.39 | 2.36 |
| mean corpuscular hemoglobin | | | | | | | | |
| Week 0 | 30.31 | 1.08 | 29.67 | 2.45 | 30.12 | 1.05 | 30.59 | 0.92 |
| Week 12 | 30.35 | 1.32 | 29.41 | 2.67 | 30.30 | 1.35 | 30.36 | 1.41 |
| Week 16 | 30.62 | 1.13 | 29.15 | 2.66 | 30.42 | 1.45 | 30.27 | 1.52 |
| mean hemoglobin concentration | | | | | | | | |
| Week 0 | 33.70 | 1.18 | 33.84 | 1.32 | 33.45 | 1.25 | 34.04 | 0.85 |
| Week 12 | 33.79 | 1.29 | 33.75 | 1.35 | 33.67 | 1.02 | 33.85 | 0.64 |
| Week 16 | 33.84 | 1.38 | 33.50 | 1.55 | 33.29 | 1.19 | 33.86 | 0.95 |

TABLE 30-continued

Analysis of blood cell characteristics in subjects with stages 3 and 4 chronic kidney disease during weeks 0 to 16 of the test

|  | Stage 3 | | | | Stage 4 | | | |
| --- | --- | --- | --- | --- | --- | --- | --- | --- |
|  | Test group | | Placebo group | | Test group | | Placebo group | |
|  | Mean | Mean | Mean | SD | Mean | SD | Mean | SD |
| platelet | | | | | | | | |
| Week 0 | 222.75 | 96.17 | 216.43 | 64.94 | 194.55 | 41.30 | 245.00 | 36.65 |
| Week 12 | 227.00 | 87.95 | 217.21 | 67.92 | 184.09 | 40.36 | 224.25 | 52.77 |
| Week 16 | 236.42 | 88.78 | 214.36 | 72.83 | 183.36 | 38.33 | 245.75 | 55.27 |
| eosinophil | | | | | | | | |
| Week 0 | 2.51 | 1.72 | 2.89 | 1.64 | 3.81 | 2.30 | 2.03 | 2.12 |
| Week 12 | 3.04 | 1.78 | 3.54 | 1.85* | 4.77 | 2.95 | 1.51 | 0.82* |
| Week 16 | 2.51 | 2.07 | 8.74 | 17.17 | 3.89 | 2.12 | 3.03 | 1.62 |
| lymphocyte | | | | | | | | |
| Week 0 | 25.89 | 4.07 | 30.24 | 9.23#* | 26.47 | 5.52 | 14.01 | 7.17* |
| Week 12 | 32.39 | 4.98# | 28.35 | 7.11 | 25.57 | 7.01 | 21.82 | 9.87 |
| Week 16 | 30.02 | 4.87 | 30.85 | 8.02 | 25.85 | 6.31 | 24.81 | 9.81 |
| monocyte | | | | | | | | |
| Week 0 | 5.11 | 1.61 | 6.71 | 1.68* | 6.11 | 1.52 | 6.36 | 3.90 |
| Week 12 | 5.88 | 1.72 | 6.71 | 1.47 | 7.22 | 1.80 | 6.84 | 1.25 |
| Week 16 | 5.38 | 1.52 | 6.75 | 1.45#* | 6.68 | 2.61 | 4.87 | 0.47 |
| lobulated leukocyte | | | | | | | | |
| Week 0 | 66.04 | 5.91 | 59.69 | 10.81#* | 63.06 | 7.03 | 77.35 | 10.96* |
| Week 12 | 58.13 | 4.75 | 60.93 | 8.06 | 61.96 | 7.53 | 69.56 | 9.97 |
| Week 16 | 56.71 | 17.08 | 48.06 | 21.40 | 57.27 | 19.91 | 66.87 | 9.10 |
| basophil | | | | | | | | |
| Week 0 | 0.45 | 0.19 | 0.46 | 0.26 | 0.55 | 0.33 | 0.28 | 0.22 |
| Week 12 | 0.55 | 0.24 | 0.47 | 0.22 | 0.48 | 0.25 | 0.33 | 0.05 |
| Week 16 | 0.47 | 0.17 | 0.54 | 0.30 | 0.41 | 0.23 | 0.43 | 0.15 |

Example 11: Urine Analysis

The urine analysis results of the 41 subjects before test are shown in Tables 31 and 32, where the difference between the two groups is compared by Wilcoxon rank-sum test, and the values are expressed as mean, standard deviation, and minimum-maximum. In the tables, the symbols "(+), (++), (+++) and (++++)" indicating urine positive are represented by "1, 2, 3, and 4" sequentially. It can be known from the detection results that the average UPro (Urinary protein), UG (Urine glucose), UOB (Urine occult blood), and ULE (Urine leukocyte lipase) positive reaction rates in subjects with chronic kidney disease are greater than "0". Except for the UG and SG, other indices in subjects with stage 4 chronic kidney disease are higher than those in subjects with stage 3 chronic kidney disease. The subjects with stage 4 chronic kidney disease has an average Upro of 60.7%, and the positive reaction rate before test is obviously higher than that of the subjects with stage 3 chronic kidney disease (18.2%). The quantified values are 1.33±0.82 and 0.69±0.97 on average respectively, suggesting that the subjects with stage 4 chronic kidney disease has a more serious UPro than the subjects with stage 3 chronic kidney disease. However, the SG value of the subjects with stage 4 chronic kidney disease is considerably lower than that of the subjects with stage 3 chronic kidney disease (P<0.05).

Tables 33 and 34 compare the difference between the two groups by Wilcoxon rank-sum test, and the values are expressed as mean, standard deviation, and minimum-maximum. In the tables, the symbol "#" indicates that there is difference between those with different courses of disease in the same group (p<0.05). At week 12 of the test, the UG value of the subjects with stage 3 chronic kidney disease in the test group is decreased by 0.83±1.40, and is obviously lower than that of the placebo group (0.36±0.93) (P<0.05). The UPro, UOB and ULE of the subjects with stage 4 chronic kidney disease in the test group are also decreased and are lower than those of the placebo group.

As can be known from the results above, the UPro, UG, UOB, and ULE of the test group are all reduced and are lower than those of the placebo group. At weeks 0, 12, and 16 of the test and after withdrawal (weeks 16 to 12), the variation in UPro of the subjects with stage 3 chronic kidney disease in the test group is lower than that of the subjects with stage 4 chronic kidney disease; and there is significant difference between the values at week 0 and 16 of the test. The variation in the UG value (weeks 16 to 12) is obviously higher than that of the subjects with stage 4 chronic kidney disease, and the case is on the contrary after withdrawal. These suggest that the lactic acid bacteria containing composition disclosed in the present invention can reduce the UPro, UG, UOB, and ULE values of the patients with stages 3 and 4 chronic kidney disease, and effect is more preferable upon consecutive administration. The effect is better in patients with stage 3 chronic kidney disease.

TABLE 31

Urine analysis of all the subjects before test

|  | Mean | SD | Range |
|---|---|---|---|
| PH | 5.60 | 0.62 | 5-8 |
| UPro | 0.93 | 0.96 | 0-3 |
| UG | 0.49 | 1.14 | 0-4 |
| UOB | 0.17 | 0.44 | 0-2 |
| ULE | 0.10 | 0.49 | 0-3 |
| Urine specific gravity | 1.01 | 0.01 | 1.00-1.03 |

TABLE 32

Urine analysis of subjects with stages 3 and 4 chronic kidney disease before test

|  | Stage 3 (n = 26) | | | Stage 4 (n = 15) | | |
|---|---|---|---|---|---|---|
|  | Mean | SD | Range | Mean | SD | Range |
| PH | 5.58 | 0.70 | 5-8 | 5.63 | 0.48 | 5-6.5 |
| UPro | 0.69 | 0.97 | 0-3 | 1.33 | 0.82 | 0-3 |
| UG | 0.69 | 1.35 | 0-4 | 0.13 | 0.52 | 0-2 |
| UOB | 0.12 | 0.43 | 0-2 | 0.27 | 0.46 | 0-1 |
| ULE | 0.00 | 0.00 | 0-0 | 0.27 | 0.80 | 0-3 |
| Urine specific gravity | 1.02 | 0.015 | 1.01-1.03 | 1.01 | 0.003 | 1.00-1.02 |

TABLE 33

Urine analysis of all the subjects during weeks 0 to 16 of the test

|  | Test group | | Placebo group | |
|---|---|---|---|---|
|  | Mean | SD | Mean | SD |
| PH | | | | |
| Week 0 | 5.74 | 0.77 | 5.75 | 0.97 |
| Week 12 | 5.87 | 0.89 | 5.96 | 0.99 |
| Week 16 | 5.68 | 0.76 | 5.63 | 0.74 |
| Upro | | | | |
| Week 0 | 1.13 | 0.92 | 0.75 | 0.97 |
| Week 12 | 1.09 | 1.04 | 0.92 | 1.00 |
| Week 16 | 1.23 | 0.97 | 0.83 | 0.94 |
| UG | | | | |
| Week 0 | 0.57 | 1.31 | 1.08 | 1.68 |
| Week 12 | 0.17 | 0.65 | 0.25 | 0.87 |
| Week 16 | 0.36 | 1.05 | 0.67 | 1.37 |
| UOB | | | | |
| Week 0 | 0.13 | 0.34 | 0.00 | 0.00 |
| Week 12 | 0.04 | 0.21 | 0.00 | 0.00 |
| Week 16 | 0.09 | 0.29 | 0.00 | 0.00 |
| ULE | | | | |
| Week 0 | 0.13 | 0.63 | 0.00 | 0.00 |
| Week 12 | 0.09 | 0.29 | 0.00 | 0.00 |
| Week 16 | 0.09 | 0.29 | 0.00 | 0.00 |
| Urine specific gravity | | | | |
| Week 0 | 1.01 | 0.01 | 1.02 | 0.01 |
| Week 12 | 1.01 | 0.01 | 1.02 | 0.01 |
| Week 16 | 1.01 | 0.01 | 1.02 | 0.01 |

TABLE 34

Urine analysis of subjects with stages 3 and 4 chronic kidney disease during weeks 0 to 16 of the test

|  | Stage 3 | | | | Stage 4 | | | |
|---|---|---|---|---|---|---|---|---|
|  | Test group | | Placebo group | | Test group | | Placebo group | |
|  | Mean | SD | Mean | SD | Mean | SD | Mean | SD |
| PH | | | | | | | | |
| Week 0 | 5.75 | 0.97 | 5.43 | 0.33 | 5.73 | 0.52 | 5.38 | 0.25 |
| Week 12 | 5.96 | 0.99 | 5.50 | 0.44 | 5.77 | 0.82 | 5.75 | 0.65 |
| Week 16 | 5.63 | 0.74 | 5.62 | 0.51 | 5.75 | 0.82 | 5.75 | 0.65 |
| Upro | | | | | | | | |
| Week 0 | 0.75 | 0.97# | 0.64 | 1.01 | 1.55 | 0.69 | 0.75 | 0.96 |
| Week 12 | 0.92 | 1.00 | 0.64 | 0.93 | 1.27 | 1.10 | 1.25 | 1.26 |
| Week 16 | 0.83 | 0.94# | 0.77 | 0.93 | 1.70 | 0.82 | 1.00 | 0.82 |
| UG | | | | | | | | |
| Week 0 | 1.08 | 1.68 | 0.36 | 0.93 | 0.00 | 0.00 | 0.50 | 1.00 |
| Week 12 | 0.25 | 0.87 | 0.71 | 1.44 | 0.09 | 0.30 | 0.00 | 0.00 |
| Week 16 | 0.67 | 1.37 | 0.46 | 1.13 | 0.00 | 0.00 | 0.00 | 0.00 |
| UOB | | | | | | | | |
| Week 0 | 0.00 | 0.00 | 0.21 | 0.58 | 0.27 | 0.47 | 0.25 | 0.50 |
| Week 12 | 0.00 | 0.00 | 0.14 | 0.36 | 0.09 | 0.30 | 0.25 | 0.50 |
| Week 16 | 0.00 | 0.00 | 0.23 | 0.44 | 0.20 | 0.42 | 0.25 | 0.50 |
| ULE | | | | | | | | |
| Week 0 | 0.00 | 0.00 | 0.00 | 0.00 | 0.27 | 0.90 | 0.25 | 0.50 |
| Week 12 | 0.00 | 0.00 | 0.00 | 0.00 | 0.18 | 0.40 | 0.25 | 0.50 |
| Week 16 | 0.00 | 0.00 | 0.00 | 0.00 | 0.20 | 0.42 | 0.25 | 0.50 |
| Urine specific gravity | | | | | | | | |
| Week 0 | 1.02 | 0.01# | 1.01 | 0.00 | 1.01 | 0.00 | 1.01 | 0.01 |
| Week 12 | 1.02 | 0.01 | 1.01 | 0.01 | 1.01 | 0.00 | 1.01 | 0.00 |
| Week 16 | 1.02 | 0.01 | 1.01 | 0.00 | 1.01 | 0.00 | 1.01 | 0.01 |

Example 12: Analysis of Clinical Symptoms and Gastrointestinal Symptoms

One week before test, the 41 subjects experience the clinical symptoms including fatigue, dyskoimesis, dry mouth, chills, dizziness, breathlessness, chest distress, nausea, vomit, loss of appetite, diarrhea, constipation, dry skin, itchy skin, muscle weakness, numbness of limbs, cramps, joint pain, and sexual problems.

After test, the incidence of the clinical symptoms to the subjects is analyzed. The results are shown in Table 35 and 36, where the incidences of the symptoms in the two groups are compared by Fisher's exact test. The improvement rate is calculated by a formula: (week 12-week 0)*100. In the tables, the symbol "*" indicates that there is significant difference between the improvement rats before and after test ($p<0.05$). The improvement rate is the incidence at week 12 minus the incidence at week 0 of the test (W12-W0). The results show that at week 12 of the test, the incidences of fatigue, dyskoimesis, dry mouth, dizziness, breathlessness, nausea, diarrhea, constipation, dry skin, muscle weakness, cramps, joint pain, sexual problems, and other symptoms in the test group are reduced; and the improvement effect (in terms of proportions of persons) on dyskoimesis, dry mouth, dizziness, breathlessness, nausea, diarrhea, dry skin, cramps, joint pain, sexual problems, and other symptoms are superior to that in the placebo group.

Further, after consuming the lactic acid bacteria containing composition, the incidences of fatigue, dizziness, breathlessness, nausea, diarrhea, constipation, dry skin, itchy skin, muscle weakness, joint pain, sexual problems, and other symptoms to the subjects with stage 3 chronic kidney disease in the test group are reduced, and the improvement effect (in terms of proportions of persons) on dyskoimesis, breathlessness, nausea, diarrhea, constipation and sexual problems is superior to that in the placebo group. After consuming the lactic acid bacteria containing composition, the incidences of fatigue, dyskoimesis, dry mouth, dizziness, chest distress, diarrhea, constipation, muscle weakness, cramps, joint pain, and other symptoms to the subjects with stage 4 chronic kidney disease in the test group are reduced, and the improvement effect (in terms of proportions of persons) on dyskoimesis, dry mouth, nausea, loss of appetite, diarrhea, constipation, dry skin, itchy skin, muscle weakness, numbness of limbs, cramps, joint pain and other symptoms is also superior to that in the placebo group.

Tables 37 and 38 compare the difference between the two groups by Wilcoxon rank-sum test, and the values are expressed as mean, standard deviation, and minimum-maximum. The improvement rate is calculated by a formula: (week 12-week 0)*100. In the tables, the symbol "*" indicates that there is significant difference between those with the same course of disease in different groups ($p<0.05$). The results show that by using the lactic acid bacteria containing composition disclosed in the present invention, the clinical symptoms including fatigue, cramps, dyskoimesis, constipation, muscle weakness, dry mouth, breathlessness, dry skin, joint pain, dizziness, diarrhea, and sexual problems can be ameliorated. With respect to the patients with stage 3 chronic kidney disease, dizziness, dry mouth, breathlessness, diarrhea, constipation and other symptoms are reduced. With respect to the patients with stage 4 chronic kidney disease, dizziness, dry mouth, breathlessness, loss of appetite, constipation and other symptoms are reduced.

It can be known from the results above that by administering the lactic acid bacteria containing composition disclosed in the present invention, the improvement rate is 52.17% for the fatigue symptom of the patients with chronic kidney disease, 47.83% for the cramp symptom, and over 30% for dyskoimesis, dry mouth, itchy skin, muscle weakness, dizziness, constipation, dry skin, joint pain, and other symptoms. In particular, by administering the lactic acid bacteria containing composition disclosed in the present invention, the improvement rate is 50% for the fatigue symptom of the patient with stage 3 chronic kidney disease; over 40% for dyskoimesis, muscle weakness, cramps, joint pain, sexual problems, and other symptoms, and over 30% for itchy skin, dizziness, breathlessness, constipation and other symptoms. By administering the lactic acid bacteria containing composition disclosed in the present invention, the improvement rate is over 50% for fatigue, dry mouth, cramps, and other symptoms of the patients with stage 4 chronic kidney disease; over 40% for dry skin, joint pain, and other symptoms; and over 30% for dyskoimesis, muscle weakness, constipation, and other symptoms.

Accordingly, it can be known that the lactic acid bacteria containing composition disclosed in the present invention is useful in ameliorating the clinical symptoms in patients with chronic kidney disease, including for example fatigue, cramps, dyskoimesis, dyspnea, dry mouth, itchy skin, muscle weakness, dizziness, tachypnea, chest tightness, sexual problems, constipation, dry skin, and joint pain, as well as in ameliorating dyskoimesis, dry mouth, nausea, loss of appetite, diarrhea, constipation, dry skin, itchy skin, muscle weakness, numbness of limbs, cramps, joint pain, and other symptoms.

TABLE 35

Number analysis of persons with clinical symptoms among all the subjects during week 0 to 12 of the test

| clinical symptoms | | Test group (n, %) | Placebo group (n, %) |
|---|---|---|---|
| fatigue | Week 0 | 19 (82.6) | 15 (83.3) |
| | Week 12 | 14 (60.9) | 12 (66.)7 |
| | Improvement rate | 12 (52.17) | 11 (61.11) |
| dyscoimesis | Week 0 | 12 (52.2) | 10 (55.6) |
| | Week 12 | 10 (43.5) | 11 (61.1) |
| | Improvement rate | 9 (39.13) | 3 (16.67) |
| dry mouth | Week 0 | 12 (52.2) | 12 (66.7) |
| | Week 12 | 11 (47.8) | 12 (66.7) |
| | Improvement rate | 9 (39.13) | 5 (27.78) |
| itchy skin | Week 0 | 13 (56.5) | 9 (50.0) |
| | Week 12 | 13 (56.5) | 5 (27.8) |
| | Improvement rate | 7 (30.43) | 8 (44.44) |
| muscle weakness | Week 0 | 13 (56.5) | 10 (55.6) |
| | Week 12 | 10 (43.5) | 4 (22.2) |
| | Improvement rate | 9 (39.13) | 8 (44.44) |
| numbness of limbs | Week 0 | 13 (56.5) | 11 (61.1) |
| | Week 12 | 13 (56.5) | 8 (44.4) |
| | Improvement rate | 6 (26.09) | 7 (38.89) |
| cramps | Week 0 | 17 (73.9) | 12 (66.7) |
| | Week 12 | 13 (56.5) | 6 (33.3) |
| | Improvement rate | 11 (47.83) | 8 (44.44) |
| feel cold | Week 0 | 2 (8.7) | 4 (22.2) |
| | Week 12 | 5 (21.7) | 3 (16.7) |
| | Improvement rate | 1 (4.35) | 4 (22.22) |
| dizziness | Week 0 | 10 (43.5) | 11 (61.1) |
| | Week 12 | 8 (34.8) | 7 (38.9) |
| | Improvement rate | 7 (30.43) | 8 (44.44) |
| dyspnea | Week 0 | 9 (39.1) | 6 (33.3) |
| | Week 12 | 7 (30.4) | 4 (22.2) |
| | Improvement rate | 5 (27.74) | 5 (27.78) |
| chest tightness | Week 0 | 7 (30.4) | 7 (38.9) |
| | Week 12 | 7 (30.4) | 5 (27.8) |
| | Improvement rate | 3 (13.04) | 3 (16.67) |
| sexual problems | Week 0 | 9 (39.1) | 6 (33.3) |
| | Week 12 | 8 (34.8) | 6 (33.3) |
| | Improvement rate | 5 (27.74 | 3 (16.67) |
| nausea | Week 0 | 5 (21.7) | 4 (22.2) |
| | Week 12 | 4 (17.4) | 4 (22.2) |
| | Improvement rate | 4 (17.39) | 2 (11.11) |
| loss of appetite | Week 0 | 4 (17.4) | 3 (16.7) |
| | Week 12 | 4 (17.4) | 3 (16.7) |
| | Improvement rate | 4 (17.39) | 2 (11.11) |
| diarrhea | Week 0 | 8 (34.8) | 4 (22.2) |
| | Week 12 | 6 (26.1) | 9 (50.0) |
| | Improvement rate | 5 (21.74) | 2 (11.11) |
| constipation | Week 0 | 15 (65.2) | 7 (38.9) |
| | Week 12 | 10 (43.5) | 4 (22.2) |
| | Improvement rate | 8 (34.78) | 4 (22.22) |
| vomiting | Week 0 | 3 (13.0) | 3 (16.7) |
| | Week 12 | 4 (17.4) | 2 (11.1) |
| | Improvement rate | 0 (0.00) | 1 (5.56) |

TABLE 35-continued

Number analysis of persons with clinical symptoms among all the subjects during week 0 to 12 of the test

| clinical symptoms | | Test group (n, %) | Placebo group (n, %) |
|---|---|---|---|
| dry skin | Week 0 | 13 (56.5) | 6 (33.3) |
| | Week 12 | 12 (52.2) | 7 (38.9) |
| | Improvement rate | 8 (34.78) | 5 (27.78) |
| joint pain | Week 0 | 17 (73.9) | 14 (77.8) |
| | Week 12 | 13 (56.5) | 11 (61.1) |
| | Improvement rate | 9 (39.13) | 7 (38.89) |

TABLE 36

Number analysis of persons with clinical symptoms among subjects with stages 3 and 4 chronic kidney disease during weeks 0 to 12 of the test

| | | Stage 3 (n, %) | | Stage 4 (n, %) | |
|---|---|---|---|---|---|
| | | Test (n = 12) | Placebo (n = 14) | Test (n = 11) | Placebo (n = 4) |
| fatigue | Week 0 | 10 (83.3) | 11 (78.6) | 9 (81.8) | 4 (100.0) |
| | Week 12 | 8 (66.7) | 9 (64.3) | 6 (54.5) | 3 (75.0) |
| | Improvement rate | 6 (50.0) | 7 (50.00) | 6 (54.55) | 4 (100.0) |
| dyscoimesis | Week 0 | 6 (50.0) | 8 (57.1) | 6 (54.5) | 2 (50.0) |
| | Week 12 | 6 (50.0) | 9 (64.3) | 4 (36.4) | 2 (50.0) |
| | Improvement rate | 5 (41.67) | 2 (14.29) | 4 (36.36) | 1 (25.00) |
| dry mouth | Week 0 | 5 (41.7) | 11 (78.6) | 7 (63.6) | 1 (25.0) |
| | Week 12 | 7 (58.3) | 9 (64.3) | 4 (36.4) | 3 (75.0) |
| | Improvement rate | 3 (25.00) | 5 (35.71) | 6 (54.550) | 0 (0.00) |
| itchy skin | Week 0 | 7 (58.3) | 7 (50.0) | 6 (54.5) | 2 (50.0) |
| | Week 12 | 6 (50.0) | 4 (28.6) | 7 (63.6) | 1 (25.0) |
| | Improvement rate | 4 (33.33) | 7 (50.00) | 3 (27.27) | 1 (25.00) |
| muscle weakness | Week 0 | 8 (66.7) | 7 (50.0) | 5 (45.5) | 3 (75.0) |
| | Week 12 | 6 (50.0) | 2 (14.3) | 4 (36.4) | 2 (50.0) |
| | Improvement rate | 5 (41.67) | 7 (50.00) | 4 (36.36) | 1 (25.00) |
| numbness of limbs | Week 0 | 7 (58.3) | 9 (64.3) | 6 (54.5) | 2 (50.0) |
| | Week 12 | 7 (58.3) | 6 (42.9) | 6 (54.5) | 2 (50.0) |
| | Improvement rate | 3 (25.00) | 6 (42.86) | 3 (27.270) | 1 (25.00) |
| cramps | Week 0 | 7 (58.3) | 10 (71.4) | 10 (90.9) | 2 (50.0) |
| | Week 12 | 7 (58.3) | 4 (28.6) | 6 (54.5) | 2 (50.0) |
| | Improvement rate | 5 (41.67) | 8 (57.14) | 6 (54.55) | 0 (0.00) |
| feel cold | Week 0 | 2 (16.7) | 3 (21.4) | 0 (0.0) | 1 (25.0) |
| | Week 12 | 3 (25.0) | 1 (7.10) | 2 (18.2) | 2 (50.0) |
| | Improvement rate | 1 (8.33) | 3 (21.43) | 0 (0.00) | 1 (25.00) |
| dizziness | Week 0 | 7 (58.3) | 8 (57.1) | 3 (27.3) | 3 (75.0) |
| | Week 12 | 6 (50.0) | 5 (35.7) | 2 (18.2) | 2 (50.0) |
| | Improvement rate | 4 (33.33) | 6 (42.86) | 3 (27.27) | 2 (50.00) |
| dyspnea | Week 0 | 7 (58.3) | 5 (35.7) | 2 (18.2) | 1 (25.0) |
| | Week 12 | 5 (41.7) | 3 (21.4) | 2 (18.2) | 1 (25.0) |
| | Improvement rate | 4 (33.33) | 4 (25.57) | 1 (9.09) | 1 (25.00) |
| chest tightness | Week 0 | 3 (25.0) | 6 (42.9) | 4 (36.4) | 1 (25.0) |
| | Week 12 | 4 (33.3) | 5 (35.7) | 3 (27.3) | 0 (0.0) |
| | Improvement rate | 1 (8.33) | 2 (14.29) | 2 (18.18) | 1 (25.00) |
| sexual problems | Week 0 | 6 (50.0) | 4 (28.6) | 3 (27.3) | 2 (50.0) |
| | Week 12 | 4 (33.3) | 6 (42.9) | 4 (36.4) | 0 (0.0) |
| | Improvement rate | 5 (41.67) | 1 (7.14) | 0 (0.00) | 2 (50.00) |
| nausea | Week 0 | 3 (25.0) | 3 (21.4) | 2 (18.2) | 1 (25.0) |
| | Week 12 | 2 (16.7) | 3 (21.4) | 2 (18.2) | 1 (25.0) |
| | Improvement rate | 2 (16.67) | 2 (14.29) | 2 (18.18) | 0 (0.00) |
| loss of appetite | Week 0 | 1 (8.3) | 3 (21.4) | 3 (27.3) | 0 (0.0) |
| | Week 12 | 2 (16.7) | 3 (21.4) | 2 (18.2) | 0 (0.0) |
| | Improvement rate | 1 (8.33) | 2 (14.49) | 3 (27.27) | 0 (0.00) |
| diarrhea | Week 0 | 3 (25.0) | 4 (28.6) | 5 (45.5) | 0 (0.0) |
| | Week 12 | 2 (16.7) | 8 (57.1)* | 4 (36.4) | 1 (25.0) |

TABLE 36-continued

Number analysis of persons with clinical symptoms among subjects with stages 3 and 4 chronic kidney disease during weeks 0 to 12 of the test

| | | Stage 3 (n, %) | | Stage 4 (n, %) | |
|---|---|---|---|---|---|
| | | Test (n = 12) | Placebo (n = 14) | Test (n = 11) | Placebo (n = 4) |
| | Improvement rate | 3 (25.00) | 2 (14.29) | 2 (18.18) | 0 (0.00) |
| constipation | Week 0 | 8 (66.7) | 5 (35.7) | 7 (63.6) | 2 (50.0) |
| | Week 12 | 5 (41.7) | 3 (21.4) | 5 (45.5) | 1 (25.0) |
| | Improvement rate | 4 (33.33) | 3 (21.43) | 4 (36.36) | 1 (25.00) |
| vomiting | Week 0 | 2 (16.7) | 2 (14.3) | 1 (9.1) | 1 (25.0) |
| | Week 12 | 3 (25.0) | 1 (7.1) | 1 (9.1) | 1 (25.0) |
| | Improvement rate | 0 (0.00) | 1 (7.14) | 0 (0.00) | 0 (0.00) |
| dry skin | Week 0 | 7 (58.3) | 5 (35.7) | 6 (54.5) | 1 (25.0) |
| | Week 12 | 6 (50.0) | 5 (35.7) | 6 (54.5) | 2 (50.0) |
| | Improvement rate | 3 (25.00) | 5 (35.71) | 5 (45.45) | 0 (0.00) |
| joint pain | Week 0 | 9 (75.0) | 12 (85.7) | 8 (72.7) | 2 (50.0) |
| | Week 12 | 8 (66.7) | 9 (64.3) | 5 (45.5) | 2 (50.0) |
| | Improvement rate | 5 (41.67) | 7 (50.00) | 4 (36.36) | 0 (0.00) |

TABLE 37

Incidence rate of clinical symptoms in subjects in the two groups

| | | Test group | | Placebo group | |
|---|---|---|---|---|---|
| | | Mean | SD | Mean | SD |
| fatigue | Week 0 | 0.65 | 0.88 | 1.28 | 1.27 |
| | Week 12 | 0.43 | 0.73 | 0.61 | 0.85 |
| | Improvement rate | 22 | 109 | 67 | 108 |
| dyscoimesis | Week 0 | 1.00 | 1.17 | 1.17 | 1.04 |
| | Week 12 | 0.65 | 0.78 | 1.00 | 0.97 |
| | Improvement rate | 35 | 127 | 17 | 99 |
| dry mouth | Week 0 | 0.30 | 0.47 | 0.56 | 0.86 |
| | Week 12 | 0.35 | 0.57 | 0.44 | 0.78 |
| | Improvement rate | −4 | 56 | 11 | 96 |
| itchy skin | Week 0 | 0.74 | 1.10 | 0.50 | 0.79 |
| | Week 12 | 0.43 | 0.79 | 0.28 | 0.57 |
| | Improvement rate | 30 | 115 | 22 | 88 |
| muscle weakness | Week 0 | 0.22 | 0.42 | 0.33 | 0.77 |
| | Week 12 | 0.26 | 0.62 | 0.28 | 0.57 |
| | Improvement rate | −4 | 71 | 6 | 94 |
| numbness of limbs | Week 0 | 0.17 | 0.49 | 0.17 | 0.38 |
| | Week 12 | 0.26 | 0.62 | 0.11 | 0.32 |
| | Improvement rate | −9 | −42 | 6 | −24 |
| cramps | Week 0 | 0.22 | 0.52 | 0.22 | 0.55 |
| | Week 12 | 0.26 | 0.69 | 0.17 | 0.38 |
| | Improvement rate | −4 | −82 | 6 | −42 |
| feel cold | Week 0 | 0.43 | 0.66 | 0.50 | 0.99 |
| | Week 12 | 0.35 | 0.71 | 0.72 | 0.89 |
| | Improvement rate | 9 | −100 | −22 | −88 |
| dizziness | Week 0 | 1.26 | 1.21 | 0.50 | 0.71* |
| | Week 12 | 0.87 | 1.18 | 0.33 | 0.77 |
| | Improvement rate | 39 | −89 | 17 | −71 |
| dyspnea | Week 0 | 1.22 | 1.24 | 0.89 | 1.02 |
| | Week 12 | 0.87 | 1.14 | 0.44 | 0.98 |
| | Improvement rate | 35 | −130 | 44 | −120 |
| chest tightness | Week 0 | 1.04 | 1.15 | 0.94 | 1.00 |
| | Week 12 | 1.13 | 1.25 | 0.89 | 1.18 |
| | Improvement rate | −9 | −104 | 6 | −111 |
| sexual problems | Week 0 | 1.26 | 1.01 | 1.22 | 1.17 |
| | Week 12 | 0.78 | 0.85 | 0.50 | 0.86 |
| | Improvement rate | 48 | −95 | 72 | −102 |
| nausea | Week 0 | 1.43 | 1.12 | 1.72 | 1.13 |
| | Week 12 | 1.17 | 1.23 | 1.28 | 1.27 |
| | Improvement rate | 26 | −114 | 44 | −110 |
| loss of appetite | Week 0 | 1.61 | 1.03 | 1.56 | 1.10 |
| | Week 12 | 1.04 | 1.07 | 0.78 | 0.65 |
| | Improvement rate | 57 | −104 | 78 | −106 |
| diarrhea | Week 0 | 1.13 | 1.25 | 0.67 | 1.08 |
| | Week 12 | 0.87 | 1.06 | 0.61 | 0.98 |
| | Improvement rate | 26 | −136 | 6 | −116 |
| constipation | Week 0 | 0.91 | 1.00 | 0.61 | 0.70 |
| | Week 12 | 0.91 | 0.95 | 0.28 | 0.46* |
| | Improvement rate | 0 | −117 | 33 | −84 |
| vomiting | Week 0 | 0.09 | 0.29 | 0.50 | 1.04 |
| | Week 12 | 0.26 | 0.54 | 0.22 | 0.55 |
| | Improvement rate | −17 | −58 | 28 | −127 |
| dry skin | Week 0 | 1.00 | 1.13 | 1.00 | 1.08 |
| | Week 12 | 0.57 | 0.79 | 1.00 | 1.03 |
| | Improvement rate | 43 | −120 | 0 | −77 |
| joint pain | Week 0 | 0.74 | 1.10 | 0.67 | 1.03 |
| | Week 12 | 0.65 | 1.03 | 0.50 | 0.86 |
| | Improvement rate | 9 | −128 | 17 | −99 |

TABLE 38

Incidence rate of clinical symptoms in subjects with stages 3 and 4 chronic kidney disease

|  |  | Stage 3 | | | | Stage 4 | | | |
|  |  | Test | | Placebo | | Test | | Placebo | |
|  |  | Mean | SD | Mean | SD | Mean | SD | Mean | SD |
| --- | --- | --- | --- | --- | --- | --- | --- | --- | --- |
| fatigue | Week 0 | 0.83 | 0.94 | 1.21 | 1.31 | 0.45 | 0.82 | 1.50 | 1.29 |
|  | Week 12 | 0.67 | 0.89 | 0.50 | 0.76 | 0.18 | 0.40 | 1.00 | 1.15 |
|  | Improvement rate | 17 | 134 | 71 | 120 | 27 | 79 | 50 | 58 |
| dyscoimesis | Week 0 | 0.92 | 1.31 | 1.36 | 1.01 | 1.09 | 1.04 | 0.50 | 1.00 |
|  | Week 12 | 0.83 | 0.83 | 1.00 | 1.04 | 0.45 | 0.69 | 1.00 | 0.82 |
|  | Improvement rate | 8 | 124 | 36 | 101 | 64 | 129 | −50 | 58 |
| dry mouth | Week 0 | 0.25 | 0.45 | 0.50 | 0.65 | 0.36 | 0.50 | 0.75 | 1.50 |
|  | Week 12 | 0.33 | 0.49 | 0.57 | 0.85 | 0.36 | 0.67 | 0.00 | 0.00 |
|  | Improvement rate | −8 | 51 | −7 | 73 | 0 | 63 | 75 | 150 |
| itchy skin | Week 0 | 0.92 | 1.00 | 0.57 | 0.85 | 0.55 | 1.21 | 0.25 | 0.50 |
|  | Week 12 | 0.50 | 0.67 | 0.29 | 0.61 | 0.36 | 0.92 | 0.25 | 0.50 |
|  | Improvement rate | 42 | 131 | 29 | 91 | 18 | 98 | 0 | 82 |
| muscle weakness | Week 0 | 0.25 | 0.45 | 0.36 | 0.84 | 0.18 | 0.40 | 0.25 | 0.50 |
|  | Week 12 | 0.33 | 0.78 | 0.29 | 0.61 | 0.18 | 0.40 | 0.25 | 0.50 |
|  | Improvement rate | −8 | 79 | 7 | 107 | 0 | 63 | 0 | 0 |
| numbness of limbs | Week 0 | 0.25 | 0.62 | 0.14 | 0.36 | 0.09 | 0.30 | 0.25 | 0.50 |
|  | Week 12 | 0.42 | 0.79 | 0.07 | 0.27 | 0.09 | 0.30 | 0.25 | 0.50 |
|  | Improvement rate | −17 | 58 | 7 | 27 | 0 | 0 | 0 | 0 |
| cramps | Week 0 | 0.08 | 0.29 | 0.29 | 0.61 | 0.36 | 0.67 | 0.00 | 0.00 |
|  | Week 12 | 0.33 | 0.89 | 0.21 | 0.43 | 0.18 | 0.40 | 0.00 | 0.00 |
|  | Improvement rate | −25 | 97 | 7 | 47 | 18 | 60 | 0 | 0 |
| feel cold | Week 0 | 0.33 | 0.65 | 0.64 | 1.08 | 0.55 | 0.69 | 0.00 | 0.00 |
|  | Week 12 | 0.17 | 0.39 | 0.79 | 0.89* | 0.55 | 0.93 | 0.50 | 1.00 |
|  | Improvement rate | 17 | 83 | −14 | 86 | 0 | 118 | −50 | 100 |
| dizziness | Week 0 | 1.33 | 1.30 | 0.50 | 0.76 | 1.18 | 1.17 | 0.50 | 0.58 |
|  | Week 12 | 0.83 | 1.19 | 0.36 | 0.84 | 0.91 | 1.22 | 0.25 | 0.50 |
|  | Improvement rate | 50 | 90 | 14 | 77 | 27 | 90 | 25 | 50 |
| dyspnea | Week 0 | 1.58 | 1.24 | 0.71 | 0.91 | 0.82 | 1.17 | 1.50 | 1.29 |
|  | Week 12 | 1.17 | 1.27 | 0.29 | 0.83* | 0.55 | 0.93 | 1.00 | 1.41 |
|  | Improvement rate | 42 | 144 | 43 | 128 | 27 | 119 | 50 | 100 |
| chest tightness | Week 0 | 1.17 | 1.19 | 1.07 | 1.07 | 0.91 | 1.14 | 0.50 | 0.58 |
|  | Week 12 | 1.17 | 1.27 | 0.79 | 1.12 | 1.09 | 1.30 | 1.25 | 1.50 |
|  | Improvement rate | 0 | 85 | −29 | 83 | 18 | 125 | 75 | 171 |
| sexual problems | Week 0 | 1.17 | 1.19 | 1.43 | 1.22 | 1.36 | 0.81 | 0.50 | 0.58 |
|  | Week 12 | 0.92 | 1.00 | 0.50 | 0.94 | 0.64 | 0.67 | 0.50 | 0.58 |
|  | Improvement rate | −25 | 106 | −93 | 107 | −73 | 79 | 0 | 0 |
| nausea | Week 0 | 1.67 | 1.23 | 1.93 | 1.07 | 1.18 | 0.98 | 1.00 | 1.15 |
|  | Week 12 | 1.25 | 1.14 | 1.29 | 1.27 | 1.09 | 1.38 | 1.25 | 1.50 |
|  | Improvement rate | −42 | 124 | −64 | 115 | −9 | 104 | 25 | 50 |
| loss of appetite | Week 0 | 1.75 | 1.14 | 1.29 | 1.07 | 1.45 | 0.93 | 2.50 | 0.58 |
|  | Week 12 | 1.25 | 1.14 | 0.79 | 0.70 | 0.82 | 0.98 | 0.75 | 0.50 |
|  | Improvement rate | −50 | 117 | −50 | 102 | −64 | 92 | −175 | 50* |
| diarrhea | Week 0 | 1.25 | 1.36 | 0.64 | 1.01 | 1.00 | 1.18 | 0.75 | 1.50 |
|  | Week 12 | 1.00 | 1.28 | 0.50 | 0.85 | 0.73 | 0.79 | 1.00 | 1.41 |
|  | Improvement rate | −25 | 148 | −14 | 129 | −27 | 127 | 25 | 50 |
| constipation | Week 0 | 0.92 | 1.00 | 0.64 | 0.74 | 0.91 | 1.04 | 0.50 | 0.58 |
|  | Week 12 | 0.83 | 0.94 | 0.29 | 0.47 | 1.00 | 1.00 | 0.25 | 0.50 |
|  | Improvement rate | −8 | 124 | −36 | 93 | 9 | 114 | −25 | 50 |
| vomiting | Week 0 | 0.17 | 0.39 | 0.50 | 1.09 | 0.00 | 0.00 | 0.50 | 1.00 |
|  | Week 12 | 0.25 | 0.45 | 0.14 | 0.53 | 0.27 | 0.65 | 0.50 | 0.58 |

TABLE 38-continued

Incidence rate of clinical symptoms in subjects with stages 3 and 4 chronic kidney disease

|  |  | Stage 3 | | | | Stage 4 | | | |
|---|---|---|---|---|---|---|---|---|---|
|  |  | Test | | Placebo | | Test | | Placebo | |
|  |  | Mean | SD | Mean | SD | Mean | SD | Mean | SD |
|  | Improvement rate | 8 | 51 | −36 | 128 | 27 | 65 | 0 | 141 |
| dry skin | Week 0 | 1.08 | 1.24 | 1.00 | 1.11 | 0.91 | 1.04 | 1.00 | 1.15 |
|  | Week 12 | 0.75 | 0.97 | 1.07 | 1.07 | 0.36 | 0.50 | 0.75 | 0.96 |
|  | Improvement rate | −33 | 130 | 7 | 62 | −55 | 113 | −25 | 126 |
| joint pain | Week 0 | 1.00 | 1.21 | 0.50 | 0.85 | 0.45 | 0.93 | 1.25 | 1.50 |
|  | Week 12 | 0.58 | 1.00 | 0.64 | 0.93 | 0.73 | 1.10 | 0.00 | 0.00 |
|  | Improvement rate | −42 | 162 | 14 | 53 | 27 | 65 | −125 | 150* |

TABLE 39

Distribution of the number of persons with improved symptoms among subjects at week 12 of the test, as compared with the situations before test

| | All Subjects | | |
|---|---|---|---|
| n (%) | Test group | Placebo group | P-value |
| fatigue | 12 (52.17) | 11 (61.11) | 0.752 |
| dyscoimesis | 9 (39.13) | 3 (16.67) | 0.171 |
| dry mouth | 9 (39.13) | 5 (27.78) | 0.520 |
| itchy skin | 7 (30.43) | 8 (44.44) | 0.514 |
| muscle weakness | 9 (39.13) | 8 (44.44) | 0.759 |
| numbness of limbs | 6 (26.09) | 7 (38.89) | 0.503 |
| cramps | 11 (47.83) | 8 (44.44) | 1.000 |
| feel cold | 1 (4.35) | 4 (22.22) | 0.150 |
| dizziness | 7 (30.43) | 8 (44.44) | 0.514 |
| dyspnea | 5 (27.74) | 5 (27.78) | 0.724 |
| chest tightness | 3 (13.04) | 3 (16.67) | 1.000 |
| sexual problems | 5 (27.74) | 3 (16.67) | 1.000 |
| nausea | 4 (17.39) | 2 (11.11) | 0.678 |
| loss of appetite | 4 (17.39) | 2 (11.11) | 0.678 |
| diarrhea | 5 (21.74) | 2 (11.11) | 0.438 |
| constipation | 8 (34.78) | 4 (22.22) | 0.496 |
| vomiting | 0 (0.00) | 1 (5.56) | 0.439 |
| dry skin | 8 (34.78) | 5 (27.78) | 0.741 |
| joint pain | 9 (39.13) | 7 (38.89) | 1.000 |

TABLE 40

Distribution of the number of persons with improved symptoms among subjects with stages 3 and 4 chronic kidney disease at week 12 of the test, as compared with the situations before test

| | Stage 3 | | | Stage 4 | | |
|---|---|---|---|---|---|---|
| n (%) | Test | Placebo | P-value | Test | Placebo | P-value |
| fatigue | 6 (50.0) | 7 (50.00) | 1.000 | 6 (54.55) | 4 (100.0) | 0.230 |
| dyscoimesis | 5 (41.67) | 2 (14.29) | 0.190 | 4 (36.36) | 1 (25.00) | 1.000 |
| dry mouth | 3 (25.00) | 5 (35.71) | 0.682 | 6 (54.550) | 0 (0.00) | 0.103 |
| itchy skin | 4 (33.33) | 7 (50.00) | 0.452 | 3 (27.27) | 1 (25.00) | 1.000 |
| muscle weakness | 5 (41.67) | 7 (50.00) | 0.713 | 4 (36.36) | 1 (25.00) | 1.000 |
| numbness of limbs | 3 (25.00) | 6 (42.86) | 0.429 | 3 (27.270) | 1 (25.00) | 1.000 |
| cramps | 5 (41.67) | 8 (57.14) | 0.695 | 6 (54.55) | 0 (0.00) | 0.103 |
| feel cold | 1 (8.33) | 3 (21.43) | 0.598 | 0 (0.00) | 1 (25.00) | 0.267 |
| dizziness | 4 (33.33) | 6 (42.86) | 0.701 | 3 (27.27) | 2 (50.00) | 0.560 |
| dyspnea | 4 (33.33) | 4 (25.57) | 1.000 | 1 (9.09) | 1 (25.00) | 0.476 |
| chest tightness | 1 (8.33) | 2 (14.29) | 1.000 | 2 (18.18) | 1 (25.00) | 1.000 |
| sexual problems | 5 (41.67) | 1 (7.14) | 0.652 | 0 (0.00) | 2 (50.00) | 0.049 |
| nausea | 2 (16.67) | 2 (14.29) | 1.000 | 2 (18.18) | 0 (0.00) | 1.000 |
| loss of appetite | 1 (8.33) | 2 (14.49) | 1.000 | 3 (27.27) | 0 (0.00) | 0.516 |
| diarrhea | 3 (25.00) | 2 (14.29) | 0.634 | 2 (18.18) | 0 (0.00) | 1.000 |
| constipation | 4 (33.33) | 3 (21.43) | 0.665 | 4 (36.36) | 1 (25.00) | 1.000 |
| vomiting | 0 (0.00) | 1 (7.14) | 1.000 | 0 (0.00) | 0 (0.00) | — |
| dry skin | 3 (25.00) | 5 (35.71) | 0.683 | 5 (45.45) | 0 (0.00) | 0.231 |
| joint pain | 5 (41.67) | 7 (50.00) | 0.713 | 4 (36.36) | 0 (0.00) | 0.517 |

Example 13: Analysis of the Lactic Acid Bacteria Containing Composition and Renal Function Indices The renal function indices and other factors of the subjects are analyzed. The results are shown in Tables 41 and 42. The correlation between the renal function indices and other items of analysis is determined by Pearson correlation coefficients. In the tables, the symbol "*" indicates $p<0.05$; and the symbol "**" indicates $p<0.01$.

At week 0 of the test, the MDR-eGFR and CKD-EPI negatively correlate with the total body skeletal muscle, BS, TG, CHOL, LDL, IS, PCS, TP, ALB, Globulin, ALP, mean corpuscular volume, mean hemoglobin concentration, PH, UPro, UOB, and ULE, suggesting that when the MDR-eGFR and CKD-EPI in patients with progressive chronic kidney disease are reduced, the IS, PCS and urine protein are increased, and the correlation with the IS, PCS, and urine protein are significant. The cases for other items are on the contrary. However, the MDR-eGFR and CKD-EPI are in obviously positive correlation with the erythrocyte count, hemoglobin concentration, hematocrit, ALT, and specific gravity of urine.

The IS value is in obviously negative correlation with the erythrocyte counts, hematocrit, and specific gravity of urine, and in obviously positive correlation with the TP, Globulin, dry skin, and sexual problems. The PCS value is in obviously positive correlation with the problem of itchy skin.

The BUN value is in obviously negative correlation with the erythrocyte counts, hematocrit and specific gravity of urine, in obviously negative correlation with the MDR-eGFR, CKD-EPI, TP, Globulin, dry skin, and sexual problems, but in obviously positive correlation with the IS, PCS, creatinine, and urine protein.

The creatinine value is in obviously negative correlation with the MDR-eGFR, CKD-EPI, erythrocyte counts, hematocrit, ALT, and specific gravity of urine, in obviously negative correlation with the MDR-eGFR, CKD-EPI, TP, Globulin, dry skin, and sexual problems, but in obviously positive correlation with the IS, PCS, and urine protein.

Further, the data above is analyzed by Pearson correlation coefficients. The results are shown in Table 43 and 44. The correlation between the renal function indices and other items of analysis is determined by Pearson correlation coefficients. In the tables, the symbol "*" indicates $p<0.05$; and the symbol "**" indicates $p<0.01$. Tables 43 and 44 show that the decrease (week 12-week 0 of the test) in MDR-eGFR D and CKD-EPI of the patients with chronic kidney disease negatively correlates with the body weight, BMI, total body skeletal muscle, TG, BS (week 12-week 0 of the test), ALP, TP, ALB, A/G Ratio, erythrocyte counts, hemoglobin concentration, hematocrit, average corpuscular volume, and variations in PH (week 12-week 0 of the test), GLU (week 12-week 0 of the test), and SG (week 12-week 0 of the test), as well as other items, but the correlation is insignificant.

The decrease in serum BUN is in obviously negative correlation with the body fat percentage, visceral fat percentage, and subcutaneous body fat percentage, suggesting that the more the decrease in BUN is, the lower the values are, and there is significant difference with respect to the body fat percentage. The decrease in serum BUN is in positive correlation with the body weight, BMI, WHR, specific gravity of urine, total body skeletal muscle, waist circumference, and waist-hip ratio, and the correlation with the waist-hip ratio is significant.

The decrease in serum creatinine level is in negative correlation with subcutaneous body fat percentage, waist circumference, waist-hip ratio, HDL, variation in T4 (week 12-week 0 of the test), ALT, Globulin, A/G Ratio, erythrocyte counts, hemoglobin concentration, hematocrit, mean corpuscular-hemoglobin, mean hemoglobin concentration, platelets, and variations in PH (week 12-week 0 of the test) and GLU (week 12-week 0 of the test), and the correlation with the body fat percentage is significant. The decrease in serum creatinine level positively correlates with other items, and the correlation with the erythrocyte counts and hematocrit are significant.

The decrease in serum uric acid (UA) is in positive correlation with the total body skeletal muscle, waist-hip ratio, TG, AST, globulin counts, RBC, hemoglobin concentration, mean corpuscular hemoglobin, mean hemoglobin concentration, variation in PH (week 12-week 0 of the test), proteins (week 12-week 0 of the test), GLU (week 12-week 0 of the test), urine occult blood (W12-W0), and specific gravity of urine (Week 12-week 0 of the test), and in negative correlation with other items; however, the correlation is insignificant.

The decrease in IS is in negative correlation with the body weight, BMI, visceral fat percentage, total body skeletal muscle, waist circumference, waist-hip ratio, CHOL, TG, variations in LDL (week 12-week 0 of the test) and T4 (week 12-week 0 of the test), AST, ALT, A/G Ratio, erythrocyte counts, hemoglobin concentration, hematocrit, mean corpuscular volume, platelets, and variations in PH (week 12-week 0 of the test) and PRO (week 12-week 0 of the test), and in positive correlation with other items. The correlation with the body weight, BMI, hematocrit, platelet counts, and mean hemoglobin concentration is significant.

The decrease in PCS is in negative correlation with the body weight, BMI, visceral fat percentage, subcutaneous body fat percentage, CHOL, variations in LDL (week 12-week 0 of the test) and T4 (week 12-week 0 of the test), AST, ALT, ALP, TP, ALB, Globulin, A/G Ratio, erythrocyte counts, hemoglobin concentration, hematocrit, mean corpuscular volume, platelets, erythrocyte, hemoglobin concentration, hematocrit, mean corpuscular volume, platelets, and variations in PH (week 12-week 0 of the test), PRO (week 12-week 0 of the test) and SG (week 12-week 0 of the test), in positive correlation with other items, and in obviously positive correlation with urine occult blood.

The analysis results above show that after administering the lactic acid bacteria containing composition disclosed in the present invention, for the patients with chronic kidney disease who have a large decrease in body weight and BMI, the MDRD-eGFR and CKD-EPI value, and the serum IS, PCS, and UA levels are low, indicating that consumption of the lactic acid bacteria containing composition disclosed in the present invention enables the body weight and renal function indices to be improved. The decrease in body fat percentage has the same effect in amelioration of the serum creatinine level; however, the case for the erythrocyte counts and hematocrit is on the contrary, suggesting that consumption of the lactic acid bacteria containing composition disclosed in the present invention has the effect of improving the anemia indices including erythrocyte counts and hematocrit. The increase in the IS level leads to the decrease of the mean hemoglobin concentration, hematocrit, and serum creatinine level; however, the case for the platelet counts is on the contrary. Therefore, long-term consumption of the lactic acid bacteria containing composition disclosed in the present invention definitely has the efficacy of increasing the MDRD-eGFR, CKD-EPI, erythrocyte counts, and hematocrit, and ameliorating the serum BUN, creatinine, IS, and PCS levels.

TABLE 41

Pearson correlation coefficient analysis of renal function indices with other items of analysis of the subjects before test

| | BUN | Creatinint | UA | MDRD-eGFR | CKD-EPI | IS | PCS |
|---|---|---|---|---|---|---|---|
| Age | −0.147 | −0.180 | 0.071 | 0.116 | 0.041 | −0.030 | −0.215 |
| Weight | −0.241 | −0.186 | −0.056 | 0.240 | 0.261 | 0.016 | −0.055 |
| BMI | −0.265 | −0.244 | −0.055 | 0.177 | 0.204 | −0.072 | −0.028 |
| Body fat ratio | −0.053 | −0.360* | 0.133 | 0.119 | 0.137 | 0.036 | −0.073 |
| visceral fat | −0.350* | −0.291 | −0.072 | 0.292 | 0.310 | −0.103 | −0.054 |
| total body skeletal muscle | −0.176 | −0.250 | −0.105 | 0.094 | 0.112 | −0.105 | −0.186 |
| total body skeletal muscle | 0.328* | 0.295 | 0.174 | −0.295 | −0.288 | 0.237 | 0.318 |
| waist circumference | −0.144 | −0.196 | 0.062 | 0.187 | 0.194 | −0.055 | −0.038 |
| waist-hip ratio | −0.147 | −0.189 | 0.159 | 0.201 | 0.190 | −0.062 | −0.014 |
| triglyceride | −0.065 | −0.039 | 0.072 | −0.023 | −0.021 | −0.081 | −0.135 |
| triglyceride | 0.138 | 0.156 | 0.248 | −0.140 | −0.120 | −0.055 | −0.073 |
| cholesterol | 0.115 | 0.148 | 0.210 | −0.238 | −0.242 | −0.132 | 0.068 |
| LDL-C | 0.134 | 0.233 | 0.174 | −0.289 | −0.307 | −0.065 | 0.166 |
| HDL-C | −0.158 | −0.299 | −0.187 | 0.200 | 0.197 | −0.123 | −0.111 |
| T4 | −0.180 | −0.073 | 0.027 | 0.177 | 0.168 | 0.027 | 0.191 |
| MDRD-eGFR | −0.750** | −0.887** | −0.102 | — | — | — | — |
| CKD-EPI | −0.747** | −0.886** | −0.107 | 0.997** | | — | — |
| Creatinint | 0.701** | — | — | — | — | — | — |
| UA | 0.158 | −0.016 | — | — | — | — | — |
| IS | 0.507** | 0.522** | 0.180 | −0.472** | −0.473** | — | — |
| PCS | 0.324* | 0.336* | 0.126 | −0.341* | −0.330* | 0.160 | — |
| TP | 0.135 | 0.108 | 0.048 | −0.048 | −0.048 | 0.510** | 0.111 |
| ALB | −0.027 | −0.042 | 0.130 | −0.018 | −0.031 | 0.253 | −0.050 |
| Globulin | 0.187 | 0.166 | −0.040 | −0.065 | −0.055 | 0.430** | 0.184 |
| A/G ratio | −0.132 | −0.108 | 0.100 | 0.002 | −0.014 | −0.157 | −0.147 |
| AST | −0.273 | −0.285 | 0.054 | 0.263 | 0.253 | −0.232 | −0.189 |
| ALT | −0.415** | −0.338* | 0.046 | 0.327* | 0.326* | −0.298 | −0.212 |
| ALP | 0.043 | 0.104 | −0.113 | −0.088 | −0.100 | 0.050 | 0.115 |
| erythrocyte | −0.466** | −0.465** | −0.084 | 0.641** | 0.647** | −0.343* | −0.090 |
| hemoglobin | −0.448** | −0.426** | −0.029 | 0.594** | 0.592** | −0.290 | −0.184 |
| hematocrit | −0.470** | −0.431** | −0.047 | 0.584** | 0.589** | −0.367* | −0.136 |
| mean corpuscular volume | 0.119 | 0.202 | 0.062 | −0.306 | −0.309* | 0.034 | −0.104 |
| mean corpuscular hemoglobin | 0.070 | 0.137 | 0.074 | −0.142 | −0.163 | 0.170 | −0.249 |
| mean hemoglobin concentration | −0.017 | −0.022 | 0.091 | 0.136 | 0.107 | 0.237 | −0.204 |
| platelet | 0.206 | −0.004 | 0.045 | −0.088 | −0.065 | 0.024 | −0.079 |
| Blood PH | −0.110 | 0.076 | 0.048 | −0.050 | −0.054 | −0.230 | −0.004 |
| Upro | 0.261 | 0.539** | 0.077 | −0.490** | −0.473** | 0.112 | 0.302 |
| UG | −0.173 | −0.140 | −0.019 | 0.099 | 0.108 | −0.222 | −0.108 |
| UOB | 0.364* | 0.282 | 0.062 | −0.269 | −0.252 | 0.255 | 0.131 |
| Urine specific gravity | −0.036 | −0.064 | 0.104 | −0.135 | −0.143 | −0.002 | −0.040 |
| Urine PH | −0.331* | −0.364* | 0.056 | 0.411** | 0.432** | −0.321* | −0.061 |

TABLE 42

Spearman correlation coefficient analysis of the severity of the clinical symptoms with renal function indices after week 12 of the test

| | BUN | Creatinint | UA | MDRD-eGFR | CKD-EPI | IS | PCS |
|---|---|---|---|---|---|---|---|
| fatigue | −0.096 | −0.127 | 0.047 | 0.039 | 0.076 | 0.085 | −0.089 |
| dyscoimesis | −0.088 | −0.038 | 0.080 | 0.003 | −0.008 | −0.108 | 0.018 |
| dry mouth | −0.067 | −0.092 | 0.278 | 0.104 | 0.104 | 0.124 | −0.174 |
| itchy skin | 0.096 | 0.102 | −0.244 | −0.119 | −0.108 | 0.285 | 0.317* |
| muscle weakness | −0.122 | −0.204 | −0.188 | 0.202 | 0.224 | 0.083 | 0.199 |
| numbness of limbs | −0.024 | −0.016 | 0.021 | 0.023 | 0.023 | 0.065 | 0.137 |
| cramps | 0.206 | 0.215 | 0.188 | −0.249 | −0.279 | 0.165 | 0.146 |
| feel cold | 0.237 | 0.029 | 0.004 | −0.041 | −0.048 | −0.020 | 0.237 |
| dizziness | −0.109 | −0.204 | −0.006 | 0.122 | 0.138 | −0.159 | 0.000 |
| dyspnea | −0.170 | −0.097 | −0.229 | 0.097 | 0.103 | −0.158 | −0.041 |

TABLE 42-continued

Spearman correlation coefficient analysis of the severity of the
clinical symptoms with renal function indices after week 12 of the test

|  | BUN | Creatinint | UA | MDRD-eGFR | CKD-EPI | IS | PCS |
|---|---|---|---|---|---|---|---|
| chest tightness | −0.090 | 0.065 | 0.111 | −0.046 | −0.040 | 0.080 | 0.173 |
| sexual problems | −0.060 | −0.091 | −0.028 | 0.222 | 0.205 | 0.345* | −0.019 |
| nausea | 0.017 | −0.024 | −0.176 | 0.039 | 0.078 | 0.237 | 0.214 |
| loss of appetite | −0.321 | −0.175 | 0.089 | 0.048 | 0.069 | 0.123 | −0.051 |
| diarrhea | −0.204 | −0.177 | 0.068 | 0.080 | 0.111 | 0.110 | 0.076 |
| constipation | 0.284 | −0.021 | −0.027 | −0.114 | −0.102 | 0.305 | 0.285 |
| vomiting | −0.035 | −0.148 | −0.012 | 0.111 | 0.104 | 0.146 | 0.152 |
| dry skin | 0.218 | 0.149 | 0.256 | −0.178 | −0.168 | 0.335* | 0.077 |
| joint pain | −0.071 | −0.207 | −0.144 | 0.174 | 0.164 | −0.267 | −0.092 |

TABLE 43

Correlation analysis of renal function indices with other items
of analysis of the subject in the test group after week 12 of the test

| | Test Group | | | | | | |
|---|---|---|---|---|---|---|---|
| | BUN | Creatinint | UA | MDRD-eGFR | CKD-EPI | IS | PCS |
| Weight (Kg) | 0.169 | 0.326 | −0.278 | −0.069 | −0.072 | −0.485* | −0.091 |
| BMI (kg/m$^2$) | 0.175 | 0.273 | −0.238 | −0.020 | −0.022 | −0.470* | −0.074 |
| Body fat ratio (%) | −0.150 | −0.515* | −0.117 | 0.414 | 0.418 | 0.190 | 0.130 |
| visceral fat ratio (%) | −0.116 | 0.097 | −0.451 | 0.203 | 0.198 | −0.315 | −0.204 |
| subcutaneous body fat percentage (%) | −0.317 | −0.081 | −0.055 | 0.103 | 0.104 | 0.155 | −0.201 |
| total body skeletal muscle (%) | 0.285 | 0.103 | 0.085 | −0.152 | −0.149 | −0.185 | 0.147 |
| waist circumference (cm) | 0.418 | −0.153 | −0.002 | 0.228 | 0.227 | −0.165 | 0.493* |
| waist-hip ratio | 0.471* | −0.139 | 0.179 | 0.169 | 0.170 | −0.190 | 0.280 |
| BS (W12-W0) | 0.161 | 0.031 | −0.075 | −0.100 | −0.100 | 0.237 | 0.218 |
| TG | −0.043 | 0.139 | 0.038 | −0.188 | −0.189 | −0.020 | 0.001 |
| CHOL | 0.258 | 0.064 | −0.177 | 0.162 | 0.159 | −0.207 | −0.030 |
| HDL | 0.224 | −0.269 | −0.031 | 0.278 | 0.279 | 0.053 | 0.121 |
| LDL (W12-W0) | 0.276 | 0.058 | −0.162 | 0.110 | 0.106 | −0.234 | −0.065 |
| T4 (W12-W0) | 0.227 | −0.193 | −0.295 | 0.301 | 0.302 | −0.096 | 0.006 |
| AST | −0.135 | 0.005 | 0.147 | 0.037 | 0.035 | −0.025 | −0.060 |
| ALT | −0.159 | −0.008 | −0.169 | 0.063 | 0.063 | −0.102 | −0.031 |
| ALP | −0.253 | 0.277 | −0.393 | −0.322 | −0.324 | 0.107 | −0.054 |
| TP | −0.330 | 0.159 | −0.192 | −0.090 | −0.093 | 0.215 | −0.137 |
| ALB | −0.303 | 0.365 | −0.293 | −0.340 | −0.343 | 0.184 | −0.182 |
| Globulin | −0.133 | −0.075 | 0.000 | 0.129 | 0.128 | 0.128 | −0.019 |
| A/G Ratio | −0.023 | 0.204 | −0.123 | −0.226 | −0.225 | −0.019 | −0.051 |
| erythrocyte | −0.206 | 0.546* | −0.035 | −0.225 | −0.222 | −0.316 | −0.147 |
| hemoglobin | −0.219 | 0.410 | 0.097 | −0.145 | −0.144 | −0.204 | −0.091 |
| hematocrit | −0.271 | 0.653** | −0.181 | −0.318 | −0.317 | −0.454* | −0.227 |
| mean corpuscular volume | −0.123 | 0.260 | −0.308 | −0.250 | −0.255 | −0.337 | −0.206 |
| mean corpuscular hemoglobin | −0.017 | −0.262 | 0.421 | 0.226 | 0.222 | 0.244 | 0.212 |
| mean hemoglobin concentration | 0.058 | −0.342 | 0.433 | 0.323 | 0.324 | 0.426* | 0.310 |
| platelet | 0.291 | −0.013 | −0.098 | 0.085 | 0.090 | −0.508* | −0.137 |
| PH | −0.022 | −0.017 | 0.030 | −0.020 | −0.020 | −0.158 | −0.059 |
| Upro | −0.034 | 0.000 | 0.380 | 0.062 | 0.062 | −0.017 | −0.012 |
| UG | −0.011 | −0.015 | −0.145 | −0.048 | −0.048 | 0.333 | 0.318 |
| UOB | −0.257 | 0.000 | 0.281 | 0.111 | 0.111 | 0.174 | 0.474* |
| Urine specific gravity | 0.473* | 0.240 | 0.441 | −0.364 | −0.364 | 0.122 | −0.093 |

TABLE 44

Correlation analysis of renal function indices with other items of analysis of the subjects in the placebo group after week 12 of the test

| | placebo group | | | | | | |
|---|---|---|---|---|---|---|---|
| | BUN | Creatinint | UA | MDRD-eGFR | CKD-EPI | IS | PCS |
| Weight (Kg) | −0.061 | −0.033 | −0.085 | 0.000 | 0.007 | 0.182 | 0.039 |
| BMI (kg/m$^2$) | 0.233 | 0.208 | 0.336 | −0.311 | −0.296 | −0.063 | 0.000 |
| Body fat ratio (%) | 0.148 | 0.208 | −0.158 | −0.168 | −0.172 | −0.028 | 0.012 |
| visceral fat ratio (%) | 0.038 | 0.168 | 0.192 | −0.078 | −0.072 | −0.276 | 0.073 |
| subcutaneous body fat percentage (%) | 0.037 | 0.072 | −0.344 | −0.017 | −0.021 | −0.148 | 0.041 |
| total body skeletal muscle (%) | −0.311 | −0.223 | −0.042 | 0.327 | 0.330 | −0.154 | 0.139 |
| waist circumference (cm) | 0.295 | 0.345 | 0.359 | −0.359 | −0.361 | −0.106 | 0.171 |
| waist-hip ratio | 0.081 | 0.302 | 0.403 | −0.298 | −0.295 | −0.143 | 0.415 |
| BS (W12-W0) | 0.177 | 0.201 | 0.065 | −0.280 | −0.291 | 0.139 | −0.161 |
| TG | −0.031 | 0.093 | 0.102 | −0.191 | −0.199 | −0.189 | 0.394 |
| CHOL | 0.141 | 0.008 | 0.005 | −0.227 | −0.237 | 0.026 | 0.073 |
| HDL | −0.245 | −0.342 | −0.207 | 0.382 | 0.386 | 0.188 | 0.167 |
| LDL (W12-W0) | 0.144 | −0.016 | −0.028 | −0.153 | −0.159 | 0.172 | −0.186 |
| T4 (W12-W0) | 0.133 | 0.239 | 0.200 | −0.112 | −0.117 | 0.262 | 0.216 |
| AST | 0.360 | 0.116 | −0.056 | −0.029 | −0.041 | 0.068 | 0.153 |
| ALT | 0.035 | −0.147 | −0.309 | 0.378 | 0.362 | 0.278 | 0.204 |
| ALP | 0.193 | 0.038 | −0.356 | 0.150 | 0.135 | 0.029 | −0.358 |
| TP | 0.393 | 0.449 | 0.434 | −0.326 | −0.328 | 0.168 | 0.003 |
| ALB | 0.246 | 0.407 | 0.432 | −0.424 | −0.428 | 0.141 | 0.218 |
| Globulin | 0.280 | 0.207 | 0.166 | −0.034 | −0.034 | 0.087 | −0.190 |
| A/G Ratio | −0.044 | 0.074 | 0.107 | −0.226 | −0.229 | −0.001 | 0.286 |
| erythrocyte | 0.099 | 0.165 | −0.094 | −0.212 | −0.214 | −0.101 | −0.169 |
| hemoglobin | 0.002 | 0.133 | −0.014 | −0.138 | −0.141 | 0.148 | 0.014 |
| hematocrit | 0.007 | 0.200 | −0.029 | −0.254 | −0.252 | −0.135 | −0.095 |
| mean corpuscular volume | −0.200 | 0.101 | 0.230 | −0.151 | −0.142 | −0.046 | 0.249 |
| mean corpuscular hemoglobin | −0.146 | −0.024 | 0.151 | 0.085 | 0.082 | 0.489* | 0.351 |
| mean hemoglobin concentration | −0.001 | −0.094 | 0.029 | 0.186 | 0.175 | 0.653** | 0.227 |
| platelet | 0.131 | 0.171 | −0.129 | −0.044 | −0.045 | −0.068 | −0.464 |
| PH | −0.163 | −0.071 | 0.576* | 0.063 | 0.063 | −0.016 | 0.161 |
| Upro | −0.169 | 0.084 | 0.259 | −0.076 | −0.076 | −0.037 | −0.029 |
| UG | 0.284 | −0.092 | 0.038 | 0.024 | 0.024 | 0.202 | −0.085 |
| UOB | 0.117 | 0.213 | 0.305 | −0.210 | −0.210 | −0.304 | −0.153 |
| Urine specific gravity | 0.049 | 0.110 | 0.498* | −0.095 | −0.095 | 0.007 | 0.171 |

Example 14: Analysis of Nutrient Intake from Diets

The nutrient intake from diets of the subjects is analyzed at about week 12 of the test. The results are shown in Tables 45 and 46, where the difference between the two groups is compared by 2-Independent-Samples t-test, and the values are expressed as mean, standard deviation, and minimum-maximum. In the tables, the symbol "*" indicates p<0.05. It can be known from Tables 45 and 46 that there are no significant differences in the intake of calories, three main nutrients (in percentages), saturated fat, dietary fiber, ash and sodium before and after test (P>0.05), and between the subjects with stages 3 and 4 chronic kidney disease (P>0.05).

Compared with the recommends for patients with stages 3-4 chronic kidney disease in Clinical Practice Guidelines For Chronic Kidney Disease (K/DOQI), except that the fat intake in percentages from the diet is above the recommended value 30%, the protein intake before and after test is about 0.80 kg/kg/day (58.47 kg/73.39 kg; 13.41%) and 0.78 kg/kg/day (57.78 kg/74.26 kg; 13.48%) respectively, which conform to the recommends for patients with stages 3-4 chronic kidney disease: 0.6-0.8 kg/kg/day. Following the recommends for patients with stages 3-4 chronic kidney disease in the Clinical Practice Guidelines: about 1500-1800 kcal/day for those weighed 50-60 kg, the total intake of calories from the diet is 1746±565 kcal/day and 1746±565 kcal/day before and after test. The intake of the dietary fiber of the subjects is only 16.39±7.61 g/day and 15.27±6.92 g/day on average before and after test, which are below the recommend 20 g/day.

TABLE 45

Analysis of daily main nutrient intake of all the subjects

| | | Mean | SD | Range |
|---|---|---|---|---|
| Calorie | Week 0 | 1746 | 565 | 707-3133 |
| | Week 12 | 1761 | 515 | 536-2866 |
| Crude protein | Week 0 | 58.47 | 20.81 | 19.25-104.37 |
| | Week 12 | 57.78 | 17.46 | 16.84-93.38 |
| Crude protein % | Week 0 | 13.41 | 2.57 | 9.76-19.94 |
| | Week 12 | 13.48 | 3.61 | 4.60-25.29 |
| P Crude protein | Week 0 | 65.21 | 26.55 | 20.95-138.19 |
| | Week 12 | 63.92 | 25.27 | 10.32-110.87 |
| Crude protein | Week 0 | 33.40 | 7.77 | 13.70-53.23 |
| | Week 12 | 32.72 | 11.02 | 8.51-58.05 |
| Carbohydrates | Week 0 | 232.59 | 83.31 | 110.85-443.96 |
| | Week 12 | 233.72 | 90.45 | 69.82-413.78 |

TABLE 45-continued

Analysis of daily main nutrient intake of all the subjects

| | | Mean | SD | Range |
|---|---|---|---|---|
| pCHO | Week 0 | 53.58 | 8.08 | 36.15-69.40 |
| | Week 12 | 52.90 | 12.18 | 26.26-73.33 |
| Saturated fat | Week 0 | 16.23 | 8.19 | 3.24-38.27 |
| | Week 12 | 17.69 | 9.45 | 2.28-45.27 |
| Dietary fiber | Week 0 | 16.39 | 7.61 | 5.18-31.08 |
| | Week 12 | 15.27 | 6.92 | 3.72-32.15 |
| Ash | Week 0 | 10.05 | 3.73 | 4.25-19.91 |
| | Week 12 | 9.77 | 3.72 | 4.19-20.71 |

TABLE 46

Analysis of daily main nutrient intake of subjects in the two groups

| | | Test Group | | | Placebo Group | | |
|---|---|---|---|---|---|---|---|
| | | Mean | SD | Range | Mean | SD | Range |
| Calorie | Week 0 | 1661 | 469 | 915-2457 | 1853 | 666 | 707-3133 |
| | Week 12 | 1593 | 408 | 1013-2308 | 1919 | 565 | 536-2866 |
| Crude protein | Week 0 | 55.60 | 19.30 | 22.34-97.54 | 62.15 | 22.60 | 19.25-104.37 |
| | Week 12 | 53.77 | 16.49 | 21.67-76.10 | 61.57 | 17.95 | 16.84-93.38 |
| Crude protein % | Week 0 | 13.32 | 2.50 | 9.76-19.51 | 13.52 | 2.73 | 10.01-19.94 |
| | Week 12 | 13.96 | 4.61 | 4.60-25.29 | 13.02 | 2.38 | 9.82-21.14 |
| P Crude protein | Week 0 | 63.19 | 25.37 | 21.19-138.19 | 67.80 | 28.52 | 20.95-125.04 |
| | Week 12 | 57.57 | 27.07 | 10.32-110.62 | 69.91 | 22.57 | 11.21-110.87 |
| Crude protein | Week 0 | 34.04 | 8.21 | 20.83-53.23 | 32.59 | 7.32 | 13.70-44.46 |
| | Week 12 | 32.22 | 13.04 | 8.51-58.05 | 33.19 | 9.07 | 18.81-49.77 |
| Carbohydrates | Week 0 | 219.32 | 71.16 | 117.29-379.38 | 249.55 | 96.10 | 110.85-443.96 |
| | Week 12 | 206.87 | 72.22 | 69.82-356.43 | 259.07 | 100.27 | 88.04-413.78 |
| pCHO | Week 0 | 53.11 | 8.70 | 36.15-69.40 | 54.18 | 7.42 | 42.89-67.65 |
| | Week 12 | 52.42 | 14.80 | 26.26-73.33 | 53.34 | 9.50 | 37.38-68.21 |
| Saturated fat | Week 0 | 16.49 | 8.72 | 3.24-38.27 | 15.91 | 7.68 | 3.48-32.03 |
| | Week 12 | 16.35 | 11.58 | 2.28-45.27 | 18.96 | 6.99 | 4.77-31.37 |
| Dietary fiber | Week 0 | 15.94 | 7.40 | 5.18-29.65 | 16.96 | 8.06 | 6.59-31.08 |
| | Week 12 | 14.88 | 7.62 | 4.86-32.15 | 15.63 | 6.38 | 3.72-27.81 |
| Ash | Week 0 | 9.23 | 2.74 | 4.25-14.84 | 11.11 | 4.58 | 4.93-19.91 |
| | Week 12 | 10.22 | 4.59 | 4.19-20.71 | 9.34 | 2.72 | 4.34-14.59 |

It can be known from the results above that administration of the lactic acid bacteria containing composition disclosed in the present invention has no impact on the daily diet and nutrient uptake of the subjects. In other words, dietary factors do not affect the test results. This suggests that the lactic acid bacteria containing composition disclosed in the present invention has very good safety, does not affect the daily diet and nutrient uptake of the subjects, and does not cause any side effects, thus being useful as a dietary supplement, food, or a food additive, for maintaining the renal functions and delaying the occurrence of metabolic syndrome.

Taken together, it can be known that the lactic acid bacteria containing composition disclosed in the present invention has the efficacy of ameliorating metabolic syndrome and maintaining the renal function in patients with chronic kidney disease, and can effectively slow down the progression of the disease in patients with chronic kidney disease, reduce the potential of the patients undergoing dialysis treatment, and considerably reduce the risk of cardiovascular disease and stroke resulting from metabolic syndrome, thus reducing the mortality caused by chronic kidney disease.

Furthermore, the lactic acid bacteria containing composition disclosed in the present invention can not only maintain the renal functions, but also improve the liver functions and urine UPro, UG, UOB, and ULE levels, and enhance the serum calcium and magnesium levels. Therefore, for patients with chronic kidney disease, the lactic acid bacteria containing composition disclosed in the present invention is effective in the prevention of hypocalcemia, improvement of abnormalities in urine, and maintenance of liver functions. Also, the lactic acid bacteria containing composition disclosed in the present invention has good improvement effect on clinical symptoms of the patients with chronic kidney disease, thus being useful as a pharmaceutical composition or dietary supplement for improving the quality of life of the patients with chronic kidney disease.

In addition, the lactic acid bacteria containing composition disclosed in the present invention has very good safety, thus being useful as a pharmaceutical composition, daily dietary supplement, nutrient supplement, or other forms of food or compositions for being administered to subjects with chronic kidney disease for a prolonged period of time.

The present invention is described in detail by way of examples. It should be understood that any simple modifications or changes can be made by those skilled in the art without departing from the spirit of the present invention, which are all embraced in the protection scope of the claims of the present invention.

What is claimed is:

1. A composition of lactic acid bacteria comprising an isolated *Lactococcus lactis* subsp. *lactis* LL358 having Accession Number CGMCC 13317 and 16S rDNA of SEQ ID NO:1, an isolated *Lactobacillus salivarius* LS159 having Accession Number CGMCC 13316 and 16S rDNA of SEQ ID NO:2, and *Lactobacillus pentosus*, wherein the proportion of *Lactococcus lactis* subsp. *lactis* LL358, *Lactobacillus salivarius* LS159, and *Lactobacillus pentosus* in the composition is 1:1:1.

2. The composition according to claim 1, which is a pharmaceutical composition.

3. The composition according to claim 1, which is a dietary supplement.

4. A method of treating chronic kidney disease in a subject, the method comprising administering to the subject an effective amount of the composition according to claim 1 in the maintenance of renal functions of impaired kidneys.

5. A method of treating metabolic syndrome in a subject, the method comprising administering to the subject an effective amount of the composition according to claim 1 in the amelioration of metabolic syndrome.

6. A method of ameliorating hyperuricemia in a subject, the method comprising administering to the subject an effective amount of the composition according to claim 1 in the amelioration of hyperuricemia.

7. A method of ameliorating hypocalcemia in a subject, the method comprising administering to the subject an effective amount of the composition according to claim 1 in the amelioration of hypocalcemia.

* * * * *